US007241935B2

(12) United States Patent
Benning et al.

(10) Patent No.: US 7,241,935 B2
(45) Date of Patent: Jul. 10, 2007

(54) COMPOSITIONS AND METHODS FOR THE PRODUCTION OF BETAINE LIPIDS

(75) Inventors: Christoph Benning, East Lansing, MI (US); Wayne Riekhof, Morrice, MI (US)

(73) Assignee: The Board of Trustees Operating Michigan State University, Lansing, MI (US)

( * ) Notice: Subject to any disclaimer, the term of this patent is extended or adjusted under 35 U.S.C. 154(b) by 451 days.

(21) Appl. No.: 10/620,914

(22) Filed: Jul. 16, 2003

(65) Prior Publication Data

US 2004/0093639 A1    May 13, 2004

Related U.S. Application Data

(63) Continuation-in-part of application No. 10/118,495, filed on Apr. 8, 2002, now Pat. No. 7,169,597.

(60) Provisional application No. 60/283,812, filed on Apr. 13, 2001.

(51) Int. Cl.
*C12N 15/31* (2006.01)
*C12N 15/52* (2006.01)
*C12N 15/63* (2006.01)
*C12N 15/82* (2006.01)
*C12N 5/04* (2006.01)
*A01H 1/00* (2006.01)

(52) U.S. Cl. .................. 800/281; 435/69.1; 435/320.1; 435/419; 435/468; 536/23.2; 800/298

(58) Field of Classification Search ..................... None
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,965,188 A | 10/1990 | Mullis et al. | 435/6 |
| 5,584,807 A | 12/1996 | McCabe | 604/71 |

OTHER PUBLICATIONS

Doerks, et al (1998) Protein Annotation: Detective Work For Function Prediction TIG 14(6) 248-250.*
Smith et al, (1997) The Challenges Of Genome Sequence Annotation Or "The Devil Is In The Details." Nature Biotech. 15:1222-3.*
Arondel et al., "Isolation and Functional Expression in *Escherichia coli* of a Gene Encoding Phosphatidylethanolamine Methyltransferase (EC 2.1.1.17) from *Rhodobacter spaeroides*," *J. Biol. Chem.*, 268(21): 16002-16008, 1993.
Bäumlein et al., "A novel seed protein gene from *Vica faba* is developmentally regulated in transgenic tobacco and *Arabidopsis* plants," *Mol. Gen. Genet.*, 225: 459-467, 1991.
Becker, D., "Binary vectors which allow the exchange of plant selectable markers and reporter genes," *Nucleic Acids Res*, 18:203, 1990.
Benning et al., "Accumulation of a Novel Glycolipid and a Betaine Lipid in Cells of *Rhodobacter sphaeroides* Grown Under Phosphate-Limitation," *Arch. Biochem. Biophys.*, 317: 103-111, 1995.
Benning C. & Sommervill CR., "Isolation and Genetic Complementation of a Sulfolipid-Deficient Mutant of *Rhodobacter sphaeroides*," *J. Bacteriol.*, 174: 2352-2360, 1992.
Camelo, L. Guiffre de Lopez et al., "Heavy Metals Input with Phosphate Fertilizers used in Argentina" *Sci. Total Environ.*, 204(3):245-250, 1997.
Carter et al., "Improved oligonucleotide site-directed mutagenesis using M13 vectors" *Nucl. Acids. Res.*, 13: 4431-4443, 1985.
S. Clough and A. Brent, "Floral dip: a simplified method for Agrobacterium-mediated transformation of *Arabidopsis thaliana*," *Plant J.*, 16: 735-43, 1998.
Crea et al., "Chemical synthesis of genes for human insulin" *Proc Natl Acad Sci USA*, 75:5765, 1978.
Evans et al., "Identification of diacylglycerol-O(N,N,N,-trimethyl)-homoserine in the halotolerant alga, *dunaliella parva*," *Chem. Phsy. Lipids*, 31:331-338, 1982.
Fiedler et al., "A complex ensemble of cisregulatory elements controls the expression of a *Vicia faba* non-storage seed protein gene," *Plant Mol. Biol.*, 22: 669-679, 1993.
Fluhr et al., "Expression and dynamics of the pea *rbcS* multigene family and organ distribution of the transcripts," *EMBO J.*, 5: 2063-2071, 1986.
Gordon-Kamm et al., "Transformation of Maize Cells and Regeneration of Fertile Transgenic Plants," *Plant Cell*, 2: 603, 1990.
Messing et al., "A system for shotgun DNA sequencing," *Nucleic Acids Res.*, 9: 309, 1981.
Neumann et al., "Gene transfer into mouse lyoma cells by electroporation in high electric fields," *EMBO J.*, 1:841, 1982.
Ormerod et al., "Light-dependent utilization of organic compounds and photoreduction of molecular hydrogen by photosynthetic bacteria; relationships with nitrogen metabolism" *Arch. Biochem. Biopsy.*, 94:449-463, 1961.
Sambrook et al., "Molecular Biology: A Laboratory Manual," Cold Spring Harbor Press, Cold Spring Harbor, N.Y., 1989.
Sanger et al., "DNA sequencing with chain-terminating inhibitors," *Proc Natl. Acad. Sci. USA*, 74: 5463-5467, 1977.

(Continued)

*Primary Examiner*—Phuong Bui
*Assistant Examiner*—Brendan O. Baggot
(74) *Attorney, Agent, or Firm*—Medlen & Carroll, LLP

(57) ABSTRACT

The present invention relates to compositions and methods for the production of Betaine lipids. The methods of the present invention comprise the expression of recombinant enzymes (e.g. from *Rhodobacter sphaeroides*) in host cells (e.g. bacteria, yeast, and plants) to produce Betaine lipid compounds including, but not limited to, Diacylglyceryl-O-4'-(N,N,N,-trimethyl) homoserine (DGTS). The methods and compositions of the present invention may be utilized such that the amount of phosphate containing fertilizer required for the growth of a particular plant is decreased.

24 Claims, 34 Drawing Sheets

OTHER PUBLICATIONS

Sato, N and Furuya, M., "Isolation and Identification of Diacylglyceryl-*O*-4'-(*N,N,N*-trimerthyl)- homoserine from the Fern *Adiantum capillus-veneris* L" *Plant Cell Phusiol.*, 21: 1113-1120, 1983.

Short et al., "λ ZAP: a becteriophage λ expression vector with *in vivo* excision properties," *Nucleic Acids Res.*, 16: 7583-7599, 1988.

Sistrom W.R., "A requirement of sodium in the growth of *R. sphaeroides*" *J. Gen. Microbiol.* 22:778-785, 1960.

Sistrom W.R., "The kinetics of the synthesis of photopigments in *R. sphaeroides,*" *J. Gen. Microbiol.* 28:607-616, 1962.

Vogel, "A convenient growth medium for Neurospora," *Microbiol. Genetics Bull.*, 13:42-43, 1956.

Vogel et al., "1(3),2-Diacylglyceryl-3(1)-*O*-2'(hydroxymethyl)(*N,N,N*-trimthyl)-β-alanine (DGTA): A novel betaine lipid from *Ochromonas danica*(Chrysophyceae)," *Chem. Phys. Lipids*, 52: 99-109, 1990.

Von Schaeven, A., Ph.D. thesis, Freie Universität Berlin, 1989.

Zoller et al., "Oligonucleotide-directed mutagenesis using M13-derived vectors: an efficient and general procedure for the production of point mutations in any fragment of DNA," *Nucl. Acids Res.*, 10: 6487, 1987.

US 6,091,003, 07/2000, Nan et al. (withdrawn)

\* cited by examiner pQE-30, pQE-31, and pQE-32 Vectors

| Positions of elements in bases | pQE-30 | pQE-31 | pQE-32 |
|---|---|---|---|
| Vector size (bp) | 3461 | 3463 | 3462 |
| Start of numbering at XhoI (CTCGAG) | 1–6 | 1–6 | 1–6 |
| T5 promoter/lac operator element | 7–87 | 7–87 | 7–87 |
| T5 transcription start | 61 | 61 | 61 |
| 6xHis-tag coding sequence | 127–144 | 127–144 | 127–144 |
| Multiple cloning site | 145–192 | 147–194 | 146–193 |
| Lambda $t_0$ transcriptional termination region | 208–302 | 210–304 | 209–303 |
| rrnB T1 transcriptional termination region | 1064–1162 | 1066–1164 | 1065–1163 |
| ColE1 origin of replication | 1638 | 1640 | 1639 |
| β-lactamase coding sequence | 3256–2396 | 3258–2398 | 3257–2397 |

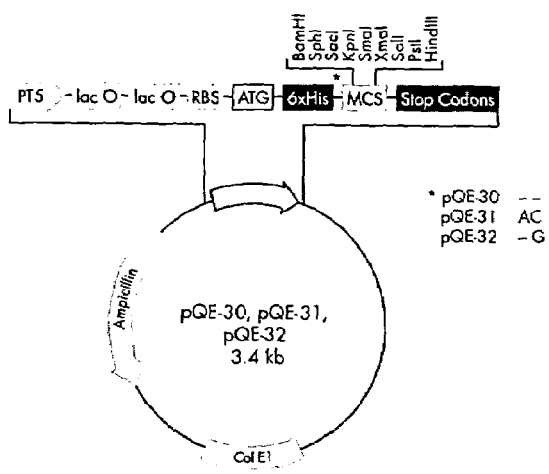

*btaA* gene cDNA Sequence

| | |
|---|---|
| 1-57 | gtgacgc agttcgccct cacccacctg cccgccccgc cggttgcccg ccagatcggc |
| 58-117 | gccgccgtgc accgcacgtc gcttctcagc gccgaaggac tgatggagcg gatgttctcg |
| 118-177 | cgcctcttcc acggcctcgt ctatccgcag atctgggagg atccggcggt ggacatggcg |
| 178-237 | gccctcgcca tccgccccgg ggaccggctg gtggccatcg cctcgggcgg ttgcaacgtg |
| 238-297 | cttcctatc tcacgcaggg gccgggctcg atcctcgccg tggatctctc gcccgcccat |
| 298-357 | gtggcgctgg ggcggctgaa gctcgccgcc gcgcggacgc tgcccgacca tgccgccttc |
| 358-417 | ttcgatctct tcggtcgcgc agacctgccc ggcaatgcgg ccctctacga ccgccacatc |
| 418-477 | gcgcccgcgc tcgacggccg gagccgccgc tactgggagg cgcgcagccc cttcggccgg |
| 478-537 | cgcatccagc tgttcgagcg cggcttctac cggcacggtg ccctcggccg cttcatcggc |
| 538-597 | gcggcccata cgctcgcgcg ggccgcgggc accgacctgc ggggctttct cgactgtccc |
| 598-657 | gacatcgagg cgcagcgcag cttcttctac gcccatatcg ggccgctctt cgaggcgccc |
| 658-717 | gtggtgcagg cgctcgcccg acggccggcc gcgctcttcg ggctggggat cccgcccgcg |
| 718-777 | caatatgcgc ttctggcggg agacggcgac ggcgacgtgc tgccggtgct gcgccagcgc |
| 778-837 | ctccaccggc tgctctgtga cttcccctg cgcgagaact acttcgcctt ccaggccatc |
| 838-897 | gcccgccgct atccgcggcc cggcgagggc gcgctgccgc cctatctcga acccaccgcc |
| 898-957 | ttcgagacgc tgcgcgagaa cgcgggccgg gtgcagatcg agaaccgcag cctgaccgag |
| 958-1017 | gcgctcgcgg ccgaacccga ggagagcatc cacggcttca ccctgctcga tgcgcaggac |
| 1018-1077 | tggatgacgg acgcgcagct gaccgcgctc tggcggcagg tgacgcgcac tgcagcgccg |
| 1078-1137 | ggcgcgcggg tgatcttccg caccggcggg gcggccgacc tgctgcccggccgagtgccc |
| 1138-1197 | gaggagatcc tcgggcactg gcgcgccgac cgggcggcgg gacaggcggg ccatgccgcc |
| 1198-1252 | gaccgttcgg cgatctacgg cggcttccac ctctaccggc ggagggacgc catga |

FIGURE 8

*btaB* gene cDNA Sequence

| | |
|---|---|
| 1-60 | atgaccgacg ccacccatgc ggcgctgatg gacgcgacct accgccacca gcgccggatc |
| 61-120 | tacgacgtca cgcggcggca cttcctgctc ggccgcgacc ggctgatcgc cgagctcgac |
| 121-180 | ccgcccccg cgcccgggt gctcgagatc gcctgcggca cggggcgcaa cctcgacctg |
| 181-240 | atcggccggc gctggcccgg ctgccggctc tggggctcg acatctgca ggagatgctg |
| 240-300 | gcctcggccc gcgcgcgtct gggccggcgc gcgacgctgg cgctcggcga tgccacccgg |
| 301-360 | ttcgaggccc tgcccctctt cggcaccgac cggttcgagc ggatcgtcct ctcctacgcg |
| 361-420 | ctctcgatga tccccgactg gcgcgaggcc ctgcgtgagg cggcgcttca tctcgtgccg |
| 421-480 | gggggggcggc tgcatgtcgt cgacttcggc gatcaggcgg gcctgcccgg ctgggcccgc |
| 481-540 | gccggcctgc gcggctggat cgggcgcttc cacgtcacgc cgcgcgacga tctgggcacg |
| 541-600 | gcactgggcg aaacggcgct cgggatcggg ggctatgccg aataccggtc cctcggcggg |
| 601-660 | ggatatgcga ttctcggcac gctcacgcgg tgagagatcc cctgccctgc gcgtgacgct |
| 661-720 | tgtctgcccg caggcgaccg gccgcgcgac ggccggcctg cgggcgatcc ggcgcactga |
| 721-780 | aggcccggcg cgtcgcgcgc ggggacgtag cccgcagcgg caagcggccg acagagcctg |
| 781-840 | acagaccgtt cacggtgcgc gctccggatc gggtgtggag ccggtgttgc agaggtcagg |
| 841-900 | cctcgaggga aagccctctg gcccgacggg caaattgtcc gggatctcta atcgggaaat |
| 901-960 | tggtcggagc gagaggattc gaacctccga cccctgctc ccgaagcagg tgcgctacca |
| 961-1020 | ggctgcgcta cgctccgacc ttggcgtgcg gattataggg tcgcgcatcc gaatgcaagg |
| 1021-1080 | gggtccgaac gcaattcgct acggagtgtc tcgcgtctcg cggcggcgca gaaggcgcgg |
| 1081-1140 | catgaggccc acctcgggcc gcaggcgcgt ctggctcgcc gggcggttct ccgacacgtt |
| 1141-1200 | gcggcgcgat tcgcggccga cgatatagag gccgctcgcg atgatgaccc ccgccccgac |
| 1201-1255 | ccaggtccag acgtcggacc gctcgccgaa gatgagccag ccgaagatcc ctgac |

FIGURE 9

*btaA* gene Amino Acid Sequence 1-50     MTQFALTHLP APPVARQIGA AVHRTSLLSA EGLMERMFSR LFHGLVYPQI 51-100   WEDPAVDMAA LAIRPGDRLV AIASGGCNVL SYLTQGPGSI LAVDLSPAHVAL 101-150  GRLKLAAART LPDHAAFFDL FGRADLPGNA ALYDRHIAPA LDGRSRRYWE 151-200  ARSPFGRRIQ LFERGFYRHG ALGRFIGAAH TLARAAGTDL RGFLDCPDIE 201-250  AQRSFFYAHI GPLFEAPVVQ ALARRPAALF GLGIPPAQYA LLAGDGDGDV 251-300  LPVLRQRLHR LLCDFPLREN YFAFQAIARR YPRPGEGALP PYLEPTAFET 301-350  LRENAGRVQI ENRSLTEALAA EPEESIHGFT LLDAQDWMTD AQLTALWRQV 351-400  TRTAAPGARV IFRTGGAADL LPGRVPEEIL GHWRADRAAG QAGHAADRSA 401-413  IYGGFHLYRR RDA

FIGURE 10

*btaB* gene Amino Acid Sequence 1-50  MTDATHAALM DATYRHQRRI YDVTRRHFLL GRDRLIAELD PPPGARVLEI 51-100  ACGTGRNLDL IGRRWPGCRL SGLDISQEML ASARARLGRR ATLALGDATR 101-150 FEALPLFGTD RFERIVLSYA LSMIPDWREA LREAALHLVP GGRLHVVDFG 151-200 DQAGLPGWAR AGLRGWIGRF HVTPRDDLGT ALGETALGIG GYAEYRSLGG 201-210 GYAILGTLTR Comments for pYES2:
5857 nucleotides GAL1 promoter: bases 1-452
T7 promoter/priming site: bases 476-495
Multiple cloning site: bases 502-601
CYC1 transcription terminator: bases 608-857
pMB1 (pUC-derived) origin: bases 1039-1712
Ampicillin resistance gene: bases 1857-2717
URA3 gene: bases 2735-3842
2 micron origin: bases 3840-5317
f1 origin: bases 5985-5840

FIGURE 14

Mutagenesis Oligonucleotide btaA-L9I

5'-CGC CCT CAC CCA C<u>AT T</u>CC CGC CCC GC-3' and its reverse complement:

5'-GCG GGG CGG G<u>AA T</u>GT GGG TGA GGG CG-3'

FIGURE 15

Mutagenesis Oligonucleotide btaA-A201G

5'-GAC TGT CCC GAG ATC GAG GGC CAG CGC CAG C-3' and its reverse complement:

5'-GCT GGC GCT GGC CCT CGA TCT CGG GAC AGT C-3'

FIGURE 16

Mutagenesis Oligonucleotide btaA-S399T

5'-GCC GCC GAC CGT ACG GCG ATC TAC GG-3' and its reverse complement:

5'-CCG TAG ATC GCC GTA CGG TCG GCG GC-3'

FIGURE 17

Mutagenesis Oligonucleotide btaB-T13S

5'-GCT GAT GGA CGC GTC CTA CCG CCA CCA G-3' and its reverse complement:

5'-CTG GTG GCG GTA GGA CGC GTC CAT CAG C-3'

FIGURE 18

Mutagenesis Oligonucleotide btaB-I115L

5'-CGG TTC GAG CGG <u>CTC</u> GTC CTC TCC TAC GC-3' and its reverse complement:

5'-GCG TAG GAG AGG AC<u>G AG</u>C CGC TCG AAC CG-3'

FIGURE 19

Mutagenesis Oligonucleotide btaB-G206A

5'-GGA TAT GCG ATT CTC <u>GCC</u> ACG CTC ACG CG-3' and its reverse complement:

5'-CGC GTG AGC GT<u>G GCG</u> AGA ATC GCA TAT CC-3'

```
RsBtaA      1   MTQFALTHLPAPPVARQIGAAVHRTSLLSAEGLMERVFSRLFHGLVYPQIWEDPAVDMAA
MlBtaA      1   MT--DVSSDLVFRRGKEVGKAVYQNRALSKAGISERLFAFLFSGLVYPQIWEDPDVDMEA
consensus   1   mt    lt       ar iG AV   LS  Gl ERmF  LF GLVYPQIWEDP VDM A RsBtaA     61   EAIRPGDRLVAIASGGCNVLSYLTQGPGSILAVDLSPAHVALGRLKLAAARTLPDHAAFE
MlBtaA     59   VQLGQCHRLVTIASGGCNLLAYLTRSPARLDAVDLNAAHLALNRMKLEAVRRLPSQGDLF
consensus  61   l  i    G RlV IASGGCNvL YLT  Pg I AVDL AHvAL RlKL A R LP  a  F RsBtaA    121   DLFGRADLPGNAALYDRHIAPALDGRSRRYWEARSPFG-RRIQLFERGFYRHGALGRFIE
MlBtaA    119   RFFGAADTSHNSQAYDRFIAPHLDPVSRHYWERRNWRGRRRIAVFDRNFYQTGLLGLFIA
consensus 121       FG AD   N   YDR IAP LD  SRrYWE R    G RRI lFeR FY   G LG FIg RsBtaA    180   AHHTLARAAGTDLRGFIGDCPDIEAQRSFFYAHIGPLFEAPWQALARRPAALFGLGIPPA
MlBtaA    179   MGHRTAKFFGVNPAHMVEARNIGEQRRFFNEELAPVFDKKLLKWATSRKASLFGLGIPPA
consensus 181    aH   Ar   G        ld    I  QR FF    igPlFe  vv    R A LFGLGIPPA RsBtaA    240   QYALLAGDGDGDVLPVLRQRLHRLLCDFPLRENYFAFQAIARRYPRPGEGALPPYLEPTA
MlBtaA    239   QYDSLITSGDGTVASVLKARLEKLACDFPLENNYFAVQAFARRYPNPGEAALPAYLEKQN
consensus 241   QY  L   GDG v   VLr RL  rL CDFPL  NYFAfQA ARRYP PGEgALP YLE RsBtaA    300   FETLRENAGRVQIENRSLTEALAAEPEESIHGFTLLDAQDWMTDAQLTALWRQVIRTAAP
MlBtaA    299   YETIRGNIDRVAIHHANLIEFLAGKDAGIVDRFILLDAQDWMTDDQLNALWSEISRTASA
consensus 301   fETlR N   RV I      L E LAa         si  F LLDAQDWMTD QL ALW    vtRTA RsBtaA    360   GARVIFRTGGAADLLPGRVPEEILGHWRADRAAGQAGHAADRSAIYGGFHLYRRRDA
MlBtaA    359   GARVIFRTAAEPSLLPGRVSTSLLDQMDYQDEASREFSARDRSAIYGGFHLYVKRTA
consensus 361   GARVIFRTgg    LLPGRV    iL  W       A       A DRSAIYGGFHLY rR A
```

FIGURE 20

```
RsBtaB     1  -------MTD THAALMD TYR QR IYD TRR H LLGRDRLI E D P GAR VLE  C
MlBtaB     1  MTELPASPEFK NH E MD VY WQR IYD TRK Y LLGRDRLI DG E P GET VLE GC
consensus  1             A HA LMDa Yr QRrIYDvTRr fLLGRDRLI   Ld P  Ga VLEiaC RsBtaB     53  GTGRN DL GRR PG R S GLDIS EM A ARAR GR -----AT AL GDAT RF AL PL
MlBtaB     61  GTGRN I AA RR DAR F GLDIS A ML  AGKA D REGLSGHV L TR GDAT D  AAAL
consensus  61  GTGRNl  L gRRwP  R  GLDIS EML sA     l R        TL  GDAT FeA   Lf RsBtaB    108  GT RF R V SY LSMIP D REA RE A LH VP GGRL H VDFG D AGLPGW RA GLRGW
MlBtaB    121  G ERF R F S S LSMIP GW EKT SA LAA SP GSLH  VDFG Q EGLPGW FRT LRGW
consensus 121  G dRFeRi  lSY LSMIP W     l  A   L P G LHvVDFG Q  GLPGW  R   LRGWi RsBtaB    168  G FHVTPR D  GTA GETALGI  YAE R L GG GYA I  T TR--
MlBtaB    181  K FHVTPR S  REV ESESRRT  TFR R L YRGYA W  M KIAS
consensus 181    rFHVTPRd L  L          Gg    yRsL  GYA Lg  l
```

FIGURE 21

MI-*btaA* gene sequence 269421 atgacggacgtctcctcggatctggtttttcgccgcggcaa
269461 ggaagttggaaaggccgtctaccagaaccgcgcgctttccaaagccggcatctccgagcg
269521 gctgttcgccttcctgttttccggcctcgtctatccgcagatctgggaagaccccgatgt
269581 cgacatggaggccatgcagcttggtcagggccatcgcatcgtcacaatcgcttccggcgg
269641 ctgcaacatcctcgcctacctcacccgttcgccggcacggatcgacgccgtcgacctcaa
269701 cgccgcccacatcgcgctgaaccgcatgaagctggaggcggtgcgccgtctgccctcgca
269761 gggcgatctgttccgctttttcggcgccgccgacaccagccacaattcgcaagcctatga
269821 ccgctttattgcgccgcatctcgatccggtcagccgccactattgggagcgccgcaactg
269881 gcgtggtcgccggcgcatcgccgtcttcgaccgcaatttctaccagaccggcctgctcgg
269941 cctgttcatcgccatgggccatcgcacggcgaaattcttcggcgtcaacccggcccacat
270001 gatggaagccaggaatatcggcgagcagcgccgcttcttcaacgaggagctggcgccggt
270061 cttcgacaagaagcttttgaaatgggcgacctcgcgtaaggcctcgctgttcggcctcgg
270121 cattccgccggcgcagtacgattccctgatcacctcaggcgacggcaccatggccagcgt
270181 tctgaaggcccggctggaaaagctcgcctgcgatttcccctggaaaacaattatttcgc
270241 ctggcaggcttttgcccgccgctatccaaatcccggtgaggccgccctgcccgcctatct
270301 ggaaaagcagaactacgaaaccatccgcggcaatatcgaccgcgtcgccatccaccatgc
270361 caatctgatcgaattcctcgccggcaaggacgcgggcaccgtcgatcgcttcatcctgct
270421 cgatgcgcaggactggatgaccgatgaccagctcaacgcgctgtggtcggaaatcagccg
270481 caccgcctccgcaggcgcccgcgtcatcttccgcaccgccgccgagcccagcctgctgcc
270541 aggccgcgtctcgacctcgctgctcgaccagtgggactatcaggacgaggcgtcgcgcga
270601 attctcggcacgcgaccgttcggccatctatggcggcttccacctctatgtgaagcgcac
270661 ggcatga

FIGURE 22

Ml-*btaB* gene sequence 270670 atgaccgagctgccggccagccccgaattcaaggccaatcatgccgaactg
270721 atggacggcgtctaccactggcagcgccacatctatgacctgactcgcaaatactatctg
270781 ctcggccgcgaccggctgatcgatgggcttgaggtgccgcaaggcggcaccgtgctggaa
270841 ctcggctgcggcaccggccgcaacatcatcctggccgcccgccgctaccctgatgcccgc
270901 ttcttcggcctggatatctcggccgagatgctggagacggccggcaaggcgatcgaccgc
270961 gaaggcctgtccggccacgtaacgctgacacgaggcgacgccaccgatttcgacgccgcg
271021 gcactttacggcatcgagcgcttcgaccgcgtcttcgtctcctattcgctgtcgatgatc
271081 ccaggctgggaaaagacggtgtcggcggcactcgccgcactatcccccaacggctcgctg
271141 cacatcgtcgatttcggccagcaggaaggcctaccgggctggttccgtaccttgctgcgc
271201 ggttggctgaaaaaattccacgtaacgccgcgtgaatcgctgcgcgaagttctggaatcg
271261 gaatctcggcgaaccggcgcaaccttccgtttccgcacgctttatcgcggttacgcctgg
271321 ctggcgatgatcaagatcgccagc<u>taa</u>

Agrobacterium tumefaciens BtaA DNA

```
   1 atg acg agt gcg gca ccc aag acc ggc ttc agc aaa aac acg aaa ctg ttt aag tcc gca ttg
  61 ctc cag cac aag gca gca ctc tcc aaa agc ctg gac agc tcc gaa ggc ttt ggc gtc ctc ttt
 121 tcc ggc gtc tat cgc cag atc gtc atc gtc gag atg aac gcg atg gaa atg gcg atg gcc gag
 181 ctt ggc gaa ggc aac cac ccg acc agc gct ctg gac gtg ttt tgc atg cac cgc ctg gcc tat
 241 ctc tcg cgc aac aag ctc cgg gcc gct gct ttc gcc cat gtg gat ttc atc gtg gcg atc ctg
 301 aac aag cgc cgc ggc acc agc gcc aac cgc cat ccc cgg ttc ttc atc gtg gcg cgc cac cac
 361 ttc ggc cgc gcc acc aag gca tac aag cgc acc agc ggt cgc acc atc gcc gag cgc cat
 421 ctg gat gcc acg ttt aac atc ctg ttt aac cgc tat acc ctt tcc cgc cgc atc gcg att
 481 tcg gtg ttc gac gcc gcc agg cgc ctg cac cgg acc ctc ggc ttc ggc atc ggc gcc ggc ctg
 541 cac atc atg cag cgc cag cag ttt gtg aaa aag atg cgt ttc aag ggc acg gtg gtg gtg tat
 601 gac gaa gaa cag cgc acg aag cgc aag aag cag ccg cag acc aag ccg gaa ccg cgc cag ctg
 661 cgc ctg tgg acg cta agc agc tcg ctt ggc ctt gcc att tat tcc ttc gcc gcg gag cgg ctg
 721 gac gag ctg gca cgc gac acg agc gac acg gtt aat ccc gtc gcc tgg cag gcc ttt gcg ccg
 781 gaa aag ctt tat gcc ccc gag cat ggt gcg cat gct cat cat acc acc gaa cca tat acc tac
 841 cgc cgt ccc gag aac ccg aac acc acg gcg cgc gtg cag gcg cgc ccg gaa ccg cgc gag ctg
 901 gaa aag cgc aag cgc cgc aac gca ctc aac ggc atc gtt atc gcg gcc tat acc gca tcc ggg
 961 ctt tcc cgc atc cgc tcc ttc cag gag tta tgg cag cgc gcg gat cgc act ggc cag gac tgg
1021 atg acg gat gtg atc gcg agc gag gcg aag tcg cag atc agc gcc tcc gca tcc ggg
1081 gca cgc gtc atc cgc ttc cgc acc gcg atc gtt tcc cgg ctt tcg ggg
1141 gac atc cgc aat cag tat ttc gtc atg gaa gcg cgc aac ctc atg atg
1201 cgc tcg gcc att tat ggc cag cag gct gca tga
```

FIGURE 25

Agrobacterium tumefaciens BtaA protein

```
MTSAAPKTGFSKNTKLKSALLQHKALSKSGLSERFFGVLFSGLVYPQIWEDPEIDMEA
MELGEGHRIVTIGSGGCNMLAYLSRNPASIDVVDLNPHHIALNKLKLAAFRHLPAHQD
VVRHFGRAGTRSNSVGYDRFIAEHLDATTKAYWSKRTLSGRRRISVFDRNIYRTGLLG
RFIGAGHIMARLHGVKLTEMAKTRTLDEQRQFFDSKVAPLFDKPVVRWLTKRKSSLFG
LGIPPRQYDELASLSSDGTVASVLKERLEKLACNFPLSDNYFAWQAFARRYPEPHEGA
LPAYLKPEYYEKIRNNTARVAVHHATYTELLSRKPANGVDRYILLDAQDWMTDVQLNE
LWSQISRTAASGARVIFRTAAEKSVIEGRLSPDIRNQWVYLEERSNELNAMDRSAIYG
GFHIYQRAMA
```

FIGURE 26

Agrobacterium tumefaciens BtaB DNA

```
  1 atgaaaacca tcggcgagaa tgtcggcctt gcagacagcg cgcatgcggg cttgatggac
 61 cgcatgtatc gccaccagcg ccatatctac gatatcaccc gcaaatatta tcttctgggc
121 cgtgaccgga ccatttccgg cctcgacgtg ccaaagggcg gcacgctgct ggaaatcggc
181 tgcggcaccg gccgcaacct gctgctggcc agccgccggt ttcccgacgc caaactcttc
241 ggcctcgata tatcagccga aatgctgctg accgcctccg agaattttgc cggcaaagcg
301 gagcgaccca ttctgcgtgt cgccgatgcc accgctttcc ggtcttcgga attcggccag
361 cccgatggct tcgaccgcgt catgatccct tatgcgctgt cgatgatacc ggactgggaa
421 aaagcgatcg aacaggcgct cgcggcgctg aaacccggcg gttcgctgca tatcgtcgat
481 ttcggccagc aggaacagtt gccgaagtgg ttccgcacgc ttcttcaagc ctggctcacc
541 cgctttcacg ttacgcccg cgcaaatctc cgttacgttc tcgccaatat ggccggccgt
601 ttcgacggga atctcgtctt cgaggaaatc gcgaggggat acgcatggcg ggctgtcatc
661 acgcttccgg ttgccgaagc cccgcagccg aagatccacc gcttattggc tgacgcctga
```

FIGURE 27

Agrobacterium tumefaciens BtaB protein

MTDATHAALMDATYRHQRRIYDVTRRHFLLGRDRLIAELDPPPG
ARVLEIACGTGRNLDLIGRRWPGCRLSGLDISQEMLASARARLG
RRATLALGDATRFEALPLFGTDRFERIVLSYALSMIPDWREALR
EAALHLVPGGRLHVVDFGDQAGLPGWARAGLRGWIGRFHVTPRD
DLGTALGETALGIGGYAEYRSLGGGYAILGTLTR

FIGURE 28

Sinorhizobium meliloti BtaA DNA

```
   1 atg acc gac ttc gcc ccg gat gcc ggc ttc aag aat ccg aaa ctg aaa agc gca
  61 ctc ctg cag cac ctt ccc gct ctt ccc gcc tcc cag atc gtg ctt gaa ctg ctc
 121 ttt tcc gga gtc gga cat ccg tgg acg tgg gac ccg gac atg gaa gcg ctg atg
 181 cag atc ctc cgt ccc gag cct ctg atc gtg ata gac cgg tcc aac cat cac tac acc
 241 tat ctc gcc gcc gag aag ctg tct gcc ttt cgc ctg ctg gat ccg cca aag gtg gcg
 301 ctc aac cgg gcc gtc gaa ggt acg cgc aat tgg acg agc cac gac ttc ctc gcg cgg
 361 ttt ctc gcc gtc gaa gga gca acc cgc cgc aac tgg cgt atc gcc gtt gac ttc cgg ccg
 421 aag ctc gat ctc ccg ttc cgc cgg cag ctg cac atc ctg gaa cgt gaa tcc cgc gcc
 481 atc ggc cat gtc gct ctc cag cag ttc tac ttt gat gat ctt ccg gcc cgt att gcg tcc
 541 agc cat gcg gag cag agc atc agc cgc agc ttc gac tcc gct cgc gaa gat cgc ttt
 601 atg cgc cag cgg cag agc agc ctg cat cgg ccg gag ttc ttc ggc acg ctg tgg cag cag
 661 atc cgt gaa tgg att acc gcg acc tgt cgg gac aat gcc aag tcc aac cca gac acc gat
 721 ttc gac aag agc gac ctg tac cgg ccg gac ctg cat gtg att cgt atc cac cag agc gac
 781 ctg gaa agg cgc tac att cgg cgg gac ttg ggc gag gtc cca gtc gtc cct cac gtg acg
 841 gca gaa cgg cgc tac att gcg aat cca aat gcg gag gtc gag gtc tat cat gca ttc gag
 901 tac gaa gcc gcg gcc att gcc ccc aag gcg gcg cgc gtc gac ctc cac gtg ttc aca cag gat
 961 ctt ctc ggc gcc agg gac cag atc ctg cgt ctg aac gcg ctg acc gcg cgc gag acc acg ccc
1021 tgg atg acc gtc ctc ttc atc gat ttc tgc ccg ctg acg gag acg ggg ctc ttc tcc gaa
1081 ggc gcg gtg ctc gac cag cag gtt cag acg atg atc agc acg gag act atg acc gag atc aaa
1141 acc acc ctc gat cag agg tac tgg cac tgc ctg cgt ccg ctg ctg ctg cat gcg cgc acc ctc gtc gga
1201 gac cgg tcg gcg atc ggc tat ggc atc aaa gca tga
```

FIGURE 29

Sinorhizobium meliloti BtaA protein

MTDFAPDAGFGKKNPKLKSALLQHKALSPAGLSERLFGLLFSGLVYPQIWEDPIVDME
AMQIRPGHRIVTIGSGGCNMLTYLSAEPARIDVVDLNPHHIALNRLKLSAFRHLPSHK
DVVRFLAVEGTRTNGQAYDVFLAPKLDPATRAYWNGRDLTGRRRIGVFGRNVYRTGLL
GRFISASHALARLHGINPEDFVKARSMREQRQFFDDKLAPLFERPVIRWITSRKSSLF
GLGIPPQQFDELASLSREKSVAAVLRNRLEKLTCHFPLRDNYFAWQAFARRYPRPDEG
ELPPYLQASRYEAIRDNAERVEVHHASFTELLAGKPAASVDRYVLLDAQDWMTDQQLN
DLWTEITRTADAGAVVIFRTAAEASILPGRLSTTLLDQWYYDAETSMRLGAEDRSAIY
GGFHIYRKKA

FIGURE 30

Sinorhizobium meliloti BtaB DNA

```
  1 atgagcgccg tgcagaccgc gaatgaaagc cacgctcatc tgatggaccg catgtatcgc
 61 taccagcggt acatctatga tttcactcgc aaatactatc tcttcggccg tgacacgctg
121 atccgtgaac tgaacccgcc gccaggcgca tcggtgctgg aagtcggctg cggcacgggc
181 cgcaatctcg ccgtgatcgg ggatctctac cccggtgcgc gcctcttcgg cctcgatatc
241 tcggccgaaa tgctggcgac cgccaaagcc aagctccggc gccaaaatcg gccggacgca
301 gtgttgcggg tcgccgacgc gacgaatttc accgccgcct cattcgatca ggaaggcttc
361 gaccggatcg tcatttccta cgccctttcc atggttcccg aatgggaaaa ggcggtcgat
421 gccgcgattg ccgcgctcaa gccgggcggc tcgctgcata tcgccgactt cggccagcag
481 gaaggttggc cggccggctt ccgccgcttc ctccaggcct ggctcagacg cttccacgtc
541 acgccgcgcg aaacgctttt cgatgtgatg cgcaaaagag ccgagagaaa cggagcggcg
601 ctcgaggtca gatcgctgag acgaggttat gcctggcttg tcgtctatcg ccgcgcggca
661 ccgtag
```

FIGURE 31

Sinorhizobium meliloti BtaB protein

MSAVQTANESHAHLMDRMYRYQRYIYDFTRKYYLFGRDTLIREL
NPPPGASVLEVGCGTGRNLAVIGDLYPGARLFGLDISAEMLATA
KAKLRRQNRPDAVLRVADATNFTAASFDQEGFDRIVISYALSMV
PEWEKAVDAAIAALKPGGSLHIADFGQQEGWPAGFRRFLQAWLR
RFHVTPRETLFDVMRKRAERNGAALEVRSLRRGYAWLVVYRRAA
P

Figure 34
A. Vogels (20 mM P$_i$)
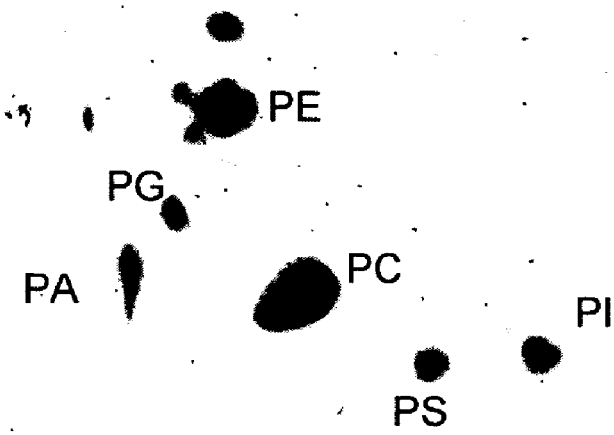
B. Vogels -P +MES (0.01 mM P$_i$)
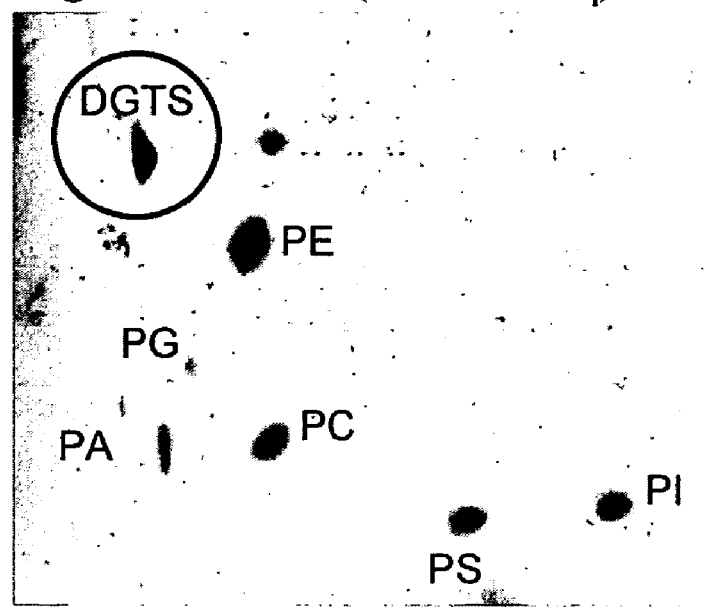

COMPOSITIONS AND METHODS FOR THE PRODUCTION OF BETAINE LIPIDS

This application is a Continuation-In-Part of U.S. patent application Ser. No. 10/118,495, filed Apr. 8, 2002 now U.S. Pat. No. 7,169,597, which claims priority to U.S. patent application Ser. No. 60/283,812, filed Apr. 13, 2001.

This invention was made in part with government support under grant MCB-0109912, from the National Science Foundation. As such, the United States Government has certain rights in the invention.

FIELD OF THE INVENTION

The present invention relates to compositions and methods for the production of betaine lipids. The methods of the present invention comprise the expression of recombinant enzymes (e.g. from *Rhodobacter sphaeroides*) in host cells (e.g. bacteria, yeast and plants) to produce betaine lipid compounds including, but not limited to, Diacylglyceryl-O-4'-(N,N,N,-trimethyl) homoserine (DGTS).

BACKGROUND

The ability to sustain conventional agriculture is based upon a high input of agrochemicals, such as phosphate-containing fertilizers. Conventional inorganic phosphorous fertilizers may cause an inadvertent addition of heavy metals, which are contained as impurities.

For example, an analysis of phosphate fertilizers commonly used in Argentina was performed to determine the concentrations of heavy metals (such as chromium, cadmium, copper, zinc, nickel, and lead) found therein. L. Guiffre de Lopez Camelo et al., "Heavy Metals Input with Phosphate Fertilizers used in Argentina," *Sci. Total Environ.*, 204(3): 245–250 (1997). The analysis revealed that: rock phosphate fertilizers contain the highest levels of cadmium and zinc; diammonium phosphate fertilizers contain enhanced levels of chromium; while superphosphate fertilizers contain the highest levels of copper and lead. Id. Thus, the continuous fertilization of soils could increase the heavy metal contents exceeding natural abundances in soils, and result in the transfer of these metals to the human food chain. Id.

Moreover, agricultural phosphate overfertilization creates environmental problems (e.g. contamination of water) and will lead to a depletion of naturally occurring phosphate fertilizer resources in the near future. Therefore, it is highly desirable to develop new strategies to reduce the amount of phosphate fertilizer needed for the optimal growth of crop plants.

SUMMARY OF THE INVENTION

The present invention relates to compositions and methods for the production of betaine lipids. In one embodiment, the compositions of the present invention comprise the nucleic acids defined by SEQ ID NO: 1, SEQ ID NO: 2, or portions thereof. In one embodiment, the methods of the present invention comprise the expression of recombinant enzymes from *Rhodobacter sphaeroides* in host cells such as bacteria and plants to produce betaine lipid compounds including, but not limited to, Diacylglyceryl-O-4'-(N,N,N,-trimethyl) homoserine (DGTS).

In one embodiment, the present invention contemplates a composition comprising isolated and purified DNA having an oligonucleotide sequence selected from the group consisting of SEQ ID NO: 1 and SEQ ID NO: 2, and portions thereof. In another embodiment, a composition comprising isolated and purified DNA having an oligonucleotide sequence selected from the group consisting of SEQ ID NO: 22 and SEQ ID NO: 23, and portions thereof, is contemplated.

It is not intended that the present invention be limited to deoxyribonucleic acids defined by SEQ ID NO: 1 and SEQ ID NO: 2, and portions thereof. In another embodiment, the present invention contemplates a composition comprising ribonucleic acid (RNA) transcribed from the DNA defined by SEQ ID NO: 1 and SEQ ID NO: 2, and portions thereof.

The present invention also contemplates a composition comprising protein translated from the ribonucleic acid (RNA) that was transcribed from the DNA defined by SEQ ID NO: 1 and SEQ ID NO: 2, and portions thereof. In an alternative embodiment, the present invention contemplates a composition comprising antibodies produced from the protein translated from the ribonucleic acid (RNA) that was transcribed from the DNA defined by SEQ ID NO: 1 and SEQ ID NO: 2, and portions thereof.

The present invention also contemplates vectors comprising SEQ ID NO: 1 and SEQ ID NO: 2, and portions thereof. In one embodiment, said vector is selected from the group consisting of pQE-31, pACYC-31, pBlueScript II SK+, pPCR-Script Amp, and pYES2.

The present invention also contemplates host cells comprising vectors comprising the DNA defined by SEQ ID NO: 1 and SEQ ID NO: 2, and portions thereof. In one embodiment, the present invention contemplates a variety of host cells selected from the group consisting of *E. coli, R. sphaeroides, M. loti* and *A. thaliana*. In another embodiment, the present invention comprises transgenic plants comprising vectors comprising the DNA defined by SEQ ID NO: 1 and SEQ ID NO: 2, and portions thereof.

The present invention also contemplates a composition comprising isolated and purified DNA encoding a protein having the amino acid sequence selected from the group consisting of SEQ ID NO: 3 and SEQ ID NO: 4, and portions thereof.

It is not intended that the present invention be limited to isolated and purified deoxyribonucleic acids (DNA) encoding a protein having the amino acid sequence selected from the group consisting of SEQ ID NO: 3 and SEQ ID NO: 4, and portions thereof. In another embodiment, the present invention contemplates a composition comprising ribonucleic acid (RNA) transcribed from DNA encoding a protein having the amino acid sequence selected from the group consisting of SEQ ID NO: 3 and SEQ ID NO: 4, and portions thereof.

In an alternative embodiment, the present invention contemplates a composition comprising antibodies produced from the protein translated from the ribonucleic acid (RNA) that was transcribed from DNA encoding a protein having the amino acid sequence selected from the group consisting of SEQ ID NO: 3 and SEQ ID NO: 4, and portions thereof.

The present invention also contemplates vectors comprising the DNA encoding a protein having the amino acid sequence selected from the group consisting of SEQ ID NO: 3 and SEQ ID NO: 4, or portions thereof. In one embodiment, the present invention contemplates a composition comprising a vector selected from the group consisting of pQE-31, pACYC-31, pBlueScript II SK+, pPCR-Script Amp, and pYES2.

The present invention also contemplates a variety of host cells comprising vectors comprising the DNA encoding a protein having the amino acid sequence selected from the group consisting of SEQ ID NO: 3 and SEQ ID NO: 4, and portions thereof. In one embodiment, the present invention contemplates a host cell selected from the group consisting of *E. coli*, *R. sphaeroides*, *M. loti*, and *A. thaliana*. In another embodiment, the present invention comprises transgenic plants comprising vectors comprising DNA encoding a protein having the amino acid sequence selected from the group consisting of SEQ ID NO: 3 and SEQ ID NO: 4, and portions thereof.

The present invention also contemplates variants of the amino acid sequences selected from the group consisting of SEQ ID NO: 3 and SEQ ID NO: 4, and portions thereof. In one embodiment, the present invention contemplates variants of the *R. sphaeroides* BtaA peptide defined by the amino acid sequence of SEQ ID NO: 3, wherein said variant comprises an amino acid substitution selected from the group consisting of:

T2S; A5G; L6I; T7S; L9I; A11G; A15G; I18L; A20G; A21G; T25S; S26T; L27I; L28I; S29T; A30G; T181S; L182I; A183G; A185G; A186G; G187A; T188S; L190I; G192A; L194I; I199L; A201G; S204T; A208G; I210L; A385G; A388G; A389G; G390A; A392G; G393A; A395G; A396G; S399T; A400G; I401L; G403A; G404A; L407I; and A413G.

In a further embodiment, the present invention contemplates variants of the *R. sphaeroides* BtaA peptide defined by the amino acid sequence of SEQ ID NO: 3, wherein said variant comprises an amino acid substitution selected from the group consisting of:

H8K; H8R; R16H; R16K; H23K; H23R; R24H; R24K; R184H; R184K; R191H; R191K; R203H; R203K; H209K; H209R; R384H; R384K; R387H; R387K; H394K; H394R; R398H; R398K; H406K; H406R; R409H; R409K; R410H; R410K; R411H; and R411K.

In another embodiment, the present invention contemplates variants of the *R. sphaeroides* BtaB peptide defined by the amino acid sequence of SEQ ID NO: 4, wherein said variant comprises an amino acid substitution selected from the group consisting of:

T2S; A4G; T5S; A7G; A8G; L9I; A12G; T13S; I20L; A103G; L104I; L106I; G107A; T108S; I115L; L117I; S118T; A120G; L121I; S122T; G191A; A193G; S197T; L198I; G199A; G200A; G201A; A203G; I204L; L205I; G206A; T207S; L208I; and T209S.

In a further embodiment, the present invention contemplates variants of the *R. sphaeroides* BtaB peptide defined by the amino acid sequence of SEQ ID NO: 4, wherein said variant comprises an amino acid substitution selected from the group consisting of:

H6K; H6R; R15H; R15K; H16K; H16R; R18H; R18K; R19H; R19K; R111H; R111K; R114H; R114K; R196H; R196K; R210H; and R210K.

In one embodiment, the present invention contemplates a method for producing betaine lipids comprising: a) providing: i) a vector comprising DNA having an oligonucleotide sequence selected from the group consisting of SEQ ID NO: 1 and SEQ ID NO: 2, and portions thereof; ii) a host cell; and b) transfecting said host cell with said vector. In a preferred embodiment, said host cell is a plant cell and said transfecting is performed under conditions such that the amount of phosphate fertilizer needed for the growth of crop plants is reduced.

It is not intended that the methods of the present invention be limited to any specific host cell capable of expressing the gene products encoded by isolated and purified DNA having an oligonucleotide sequence selected from the group consisting of SEQ ID NO: 1 and SEQ ID NO: 2, and portions thereof. In one embodiment, said host cell is prokaryotic (e.g. *E. coli*). In another embodiment, said host cell is a eukaryotic (e.g. yeast). In another embodiment, said host cell is a plant cell (e.g. *Arabidopsis*, Maize, Soybean, Sorghum, *Brassica, Medicago, Capsicum, Nicotiana, Zea*, Triticum, and *Datura*).

It is not intended that the methods of the present invention be limited to any specific vector. In one embodiment, said vector is selected from the group comprising pQE-31, pACYC-31, pBlueScript II SK+, pPCR-Script Amp, and pYES2.

In one embodiment, the present invention contemplates a method for producing betaine lipids in vitro comprising: a) providing: i) a first vector comprising DNA having the oligonucleotide sequence of SEQ ID NO: 1, and portions thereof; ii) a second vector comprising DNA having the oligonucleotide sequence of SEQ ID NO: 2; iii) host cells; iv) S-adenosylmethionine; and v) diacylglycerol; b) transfecting said host cells with said first and second vectors such that the gene products of said vectors are produced; and c) combining said gene products with said S-adenosylmethionine and said diacylglycerol in vitro under conditions such that betaine lipids are produced. In one embodiment, said host cells are selected from the group consisting of *E. coli, R. sphaeroides, M. loti*, and yeast. In a preferred embodiment, said host cells are plant cells.

It is not intended that the present invention be limited by the use of any specific method to express or produce betaine lipids including, but not limited to, DGTS. In one embodiment, the present invention contemplates the cloning of the btaA gene (SEQ ID NO: 1) into a protein expression vector selected from the group comprising pQE-9, pQE-16, pQE-30, pQE-31, pQE-32, pQE-40, pQE-60, pQE-70, pQE-80, pQE-81, pQE-82, pQE-100, pACYC-31, pBlueScript II SK+, pPCR-Script Amp, and pYES2. In another embodiment, the present invention contemplates the cloning of the btaB gene (SEQ ID NO: 2) into said protein expression vectors.

In an alternative embodiment, the invention contemplates the transformation of plant cells or tissues such that the gene product encoded by the oligonucleotide sequence selected from the group consisting of SEQ ID NO: 1 and SEQ ID NO: 2, and portions thereof, is expressed. In one embodiment, the present invention contemplates the cloning of the btaA gene (SEQ ID NO: 1) into a binary vector for introduction into *Agrobacterium tumefaciens*, and the subsequent generation of transgenic plant cells via Agrobacterial transformation. In another embodiment, the present invention contemplates the cloning of the btaB gene (SEQ ID NO: 2) into a binary vector for introduction into *Agrobacterium tumefaciens*, and the subsequent generation of transgenic plant cells via Agrobacterial transformation.

It is not intended that the invention be limited to the independent expression of the gene product encoded by the oligonucleotide sequence of SEQ ID NO:1, and portions thereof, in a single host cell, organism, or plant. Moreover, it is also not intended that the invention be limited to the independent expression of the gene product encoded by the oligonucleotide sequence of SEQ ID NO:2, and portions thereof, in a single host cell, organism, or plant. In one embodiment, the invention contemplates the co-expression of both of said gene products in a single host organism. In an alternative embodiment, the invention contemplates the transformation of plant cells or tissues such that both of said gene products are co-expressed.

It is not intended that the present invention be limited by the use of any specific method for the detection of betaine lipid production. The present invention contemplates a variety of assay formats. In one embodiment, a quantitative lipid assay utilizing thin layer chromatography (TLC) to detect the production of betaine lipids is contemplated. In another embodiment, an assay utilizing fast atom bombardment mass spectroscopy (FAB-MS) and proton-nuclear magnetic resonance ($^1$H-NMR) spectroscopy to measure the production of betaine lipids is contemplated.

In one embodiment, the production of the betaine lipid, DGTS, is visualized with iodine vapor and identified by co-chromatography with an *Arabidopsis thaliana* leaf lipid extract known to contain DGTS. In another embodiment, the production of DGTS is verified by quantitative analysis wherein reaction products are isolated from the TLC plates and used to prepare fatty acid methyl esters. The methyl esters are quantified by gas chromatography using myristic acid as the internal standard.

The methods of the present invention are conveniently carried out in a reaction vessel or container. It is not intended that the present invention be limited to any particular reaction vessel. A variety of containers can be used, including but not limited to, culture dishes, microwells, tubes, flasks and other glassware.

In addition, the present invention provides compositions comprising purified DNA having an oligonucleotide sequence selected from the group consisting of SEQ ID NO: 44, and SEQ ID NO: 49. In some embodiments, RNA transcribed from the DNA is provided, while in other embodiments, protein translated from the RNA is provided. In further embodiments, antibodies produced from the protein are provided.

The present invention also provides vectors comprising DNA having an oligonucleotide sequence selected from the group consisting of SEQ ID NO: 44, and SEQ ID NO: 49. In some embodiments, a host cell comprising the vector is provided. In some preferred embodiments, the host cell is selected from the group including but not limited to *E. coli, R. sphaeroides*, and *A. thaliana*. In further embodiments, transgenic plants comprising the vector are provided.

Moreover, the present invention provides compositions comprising isolated and purified DNA encoding a protein having an amino acid sequence selected from the group consisting of SEQ ID NO: 45, and SEQ ID NO: 50. In some embodiments, RNA transcribed from the DNA is provided, while in other embodiments, protein translated from the RNA is provided. In further embodiments, antibodies produced from the protein are provided.

The present invention also provides vectors comprising DNA encoding a protein having an amino acid sequence selected from the group consisting of SEQ ID NO: 45, and SEQ ID NO: 50. In some embodiments, a host cell comprising the vector is provided. In some preferred embodiments, the host cell is selected from the group including but not limited to *E. coli, R. sphaeroides*, and *A. thaliana*. In further embodiments, transgenic plants comprising the vector are provided.

Also provided by the present invention are purified nucleic acids that specifically hybridize to the complement of a sequence selected from the group consisting of SEQ ID NO:44, and SEQ ID NO:49, under highly stringent conditions in 5×SSPE, 1% SDS, 5× Denhardt's reagent and 100 μg/ml denatured salmon sperm DNA at 68° C. overnight, followed by washing in a solution comprising 0.1×SSPE and 0.1% SDS at 68° C., wherein the nucleic acid encodes a protein with DGTS synthetic activity. In some embodiments, vectors comprising the nucleic acid, host cells comprising the vector or transgenic plants comprising the vector are provided. In some preferred embodiments, protein encoded by the nucleic acid is provided.

Additionally, the present invention provides purified nucleic acids comprising a sequence that is at least 95% identical to SEQ ID NO:44, or a sequence that is at least 95% identical to SEQ ID NO:49, wherein the sequence encodes a protein with DGTS synthetic activity. In some embodiments, vectors comprising the nucleic acid, host cells comprising the vector or transgenic plants comprising the vector are provided. In some preferred embodiments, protein encoded by the nucleic acid is provided.

Moreover, the present invention provides peptides comprising the SAM binding domain of *C. reinhardtii* Bta1, defined herein from residue 75 to 179 of SEQ ID NO:45. In further embodiments, the present invention provides peptides comprising the Bta domain, defined herein from residue 250 to 642 of SEQ ID NO:45. For instance, some embodiments comprise heterologous peptides attached to either the *C. reinhardtii* SAM binding domain or to the Bta domain (e.g., fusion proteins). Suitable heterologous peptides include but are not limited to reporter sequences such as β-galactosidae, firefly luciferase and green fluorescent protein, and affinity tags such as polyhistidine, maltose binding protein and c-myc epitope.

Also provided are variant peptides, wherein the variant comprises an amino acid substitution including but not limited to: L77V; V85I; D86E; Y91F; I92V; D93N; L94V; A95S; K96E or S99T. In particularly preferred embodiments, the peptides are suitable for induction of DGTS synthesis upon expression in *E. coli*.

The present invention further provides peptides comprising the SAM binding domain of *N. crassa* Bta1, defined herein from residue 184 to 254 of SEQ ID NO:50. In further embodiments, the present invention provides peptides comprising the Bta domain, defined herein from residue 495 to 812 of SEQ ID NO:50. For instance, some embodiments comprise heterologous peptides attached to either the *N. crassa* SAM binding domain or to the Bta domain (e.g., fusion proteins). Suitable heterologous peptides include but are not limited to reporter sequences such as β-galactosidae, firefly luciferase and green fluorescent protein, and affinity tags such as polyhistidine, maltose binding protein and c-myc epitope.

Also provided are variant peptides, wherein the variant comprises an amino acid substitution including but not limited to: Y497F; I498L; A500T; T502S; L512V; L513M; N514E; L515I; A523T or I524L. In particularly preferred embodiments, the peptides are suitable for induction of DGTS synthesis upon expression in *E. coli*.

DESCRIPTION OF THE DRAWINGS

FIG. 1 schematically shows the vector maps, including restriction endonuclease recognition sites, of the protein expression vectors pQE-30 (SEQ ID NO: 38), pQE-31 (SEQ ID NO: 39), and pQE-32 (SEQ ID NO: 40).

FIG. 7 shows the nucleic acid sequence of the *Rhodobacter sphaeroides* btaA gene (SEQ ID NO: 1) (submitted to GenBank data base and assigned accession number AF329857, nucleotide numbers 544–1790). The start and stop codons are highlighted and underlined, respectively, for emphasis.

FIG. 8 shows the nucleic acid sequence of the *Rhodobacter sphaeroides* btaB gene (SEQ ID NO: 2) (submitted to GenBank data base and assigned accession number AF329857, nucleotide numbers 1791–2423). The start and stop codons are highlighted and underlined, respectively, for emphasis.

FIG. 9 shows the amino acid sequence of the *Rhodobacter sphaeroides* btaA gene product (SEQ ID NO: 3) (submitted to GenBank data base and assigned accession number AF329857).

FIG. 10 shows the amino acid sequence of the *Rhodobacter sphaeroides* btaB gene product (SEQ ID NO: 4) (submitted to GenBank data base and assigned accession number AF329857).

FIG. 14 shows the nucleotide sequence of the mutagenesis oligonucleotide btaA-L9I (SEQ ID NO: 5). Said oligonucleotide correlates with base numbers 12–37 of SEQ ID NO: 1. The portion of the oligonucleotide wherein the mutation is encoded is indicated by a double-underline.

FIG. 15 shows the nucleotide sequence of the mutagenesis oligonucleotide btaA-A201G (SEQ ID NO: 6). Said oligonucleotide correlates with base numbers 589–618 of SEQ ID NO: 1. The portion of the oligonucleotide wherein the mutation is encoded is indicated by a double-underline.

FIG. 16 shows the nucleotide sequence of the mutagenesis oligonucleotide btaA-S399T (SEQ ID NO: 7). Said oligonucleotide correlates with base numbers 1192–1217 of SEQ ID NO: 1. The portion of the oligonucleotide wherein the mutation is encoded is indicated by a double-underline.

FIG. 17 shows the nucleotide sequence of the mutagenesis oligonucleotide btaB-T13S (SEQ ID NO: 8). Said oligonucleotide correlates with base numbers 24–51 of SEQ ID NO: 2. The portion of the oligonucleotide wherein the mutation is encoded is indicated by a double-underline.

FIG. 18 shows the nucleotide sequence of the mutagenesis oligonucleotide btaB-I115L (SEQ ID NO: 9). Said oligonucleotide correlates with base numbers 331–359 of SEQ ID NO: 2. The portion of the oligonucleotide wherein the mutation is encoded is indicated by a double-underline.

FIG. 19 shows the nucleotide sequence of the mutagenesis oligonucleotide btaB-G206A (SEQ ID NO: 10). Said oligonucleotide correlates with base numbers 601–629 of SEQ ID NO: 2. The portion of the oligonucleotide wherein the mutation is encoded is indicated by a double-underline.

FIG. 20 shows the results of an amino acid alignment and comparison of the *R. sphaeroides* btaA gene (SEQ ID NO: 3) and its *Mesorhizobium loti* gene homolog, Ml-btaA (SEQ ID NO: 41). Amino acid residues conserved between the two organisms are indicated by a black background. Amino acid residues which differ between the two organisms, but reflect a conservative amino acid change (e.g. leucine v. isoleucine) are indicated by a gray background.

FIG. 21 shows the results of an amino acid alignment and comparison of the *R. sphaeroides* btaB gene (SEQ ID NO: 4) and its *Mesorhizobium loti* gene homolog, Ml-btaB (SEQ ID NO: 42). Amino acid residues conserved between the two organisms are indicated by a black background. Amino acid residues which differ between the two organisms, but reflect a conservative amino acid change (e.g. leucine v. isoleucine) are indicated by a gray background.

FIG. 22 shows the nucleic acid sequence of the *R. sphaeroides* btaA gene homolog from *Mesorhizobium loti*, Ml-btaA (SEQ ID NO: 22) (GenBank accession number AP002997, nucleotide numbers 269,421 to 270,667) as identified by BLAST search. The start and stop codons are highlighted and underlined, respectively, for emphasis.

FIG. 23 shows the nucleic acid sequence of the *R. sphaeroides* btaB gene homolog from *Mesorhizobium loti*, Ml-btaB (SEQ ID NO: 23) (submitted to GenBank data base and assigned accession number AP002997, nucleotide numbers 270,670 to 271,347) as identified by BLAST search. The start and stop codons are highlighted and underlined, respectively, for emphasis.

FIG. 24 shows the nucleic acid sequence of the *R. sphaeroides* btaA gene homolog from *Agrobacterium tumefaciens*, btaA (SEQ ID NO: 28).

FIG. 25 shows the amino acid sequence of the *R. sphaeroides* btaA gene homolog from *Agrobacterium tumefaciens*, btaA (SEQ ID NO: 29).

FIG. 26 shows the nucleic acid sequence of the *R. sphaeroides* btaB gene homolog from *Agrobacterium tumefaciens*, btaB (SEQ ID NO: 30).

FIG. 27 shows the amino acid sequence of the *R. sphaeroides* btaB gene homolog from *Agrobacterium tumefaciens*, btaB (SEQ ID NO: 31).

FIG. 28 shows the nucleic acid sequence of the *R. sphaeroides* btaA gene homolog from *Sinorhizobium meliloti*, btaA (SEQ ID NO: 32).

FIG. 29 shows the amino acid sequence of the *R. sphaeroides* btaA gene homolog from *Sinorhizobium meliloti*, btaA (SEQ ID NO: 33).

FIG. 30 shows the nucleic acid sequence of the *R. sphaeroides* btaB gene homolog from *Sinorhizobium meliloti*, btaB (SEQ ID NO: 34).

FIG. 31 shows the amino acid sequence of the *R. sphaeroides* btaB gene homolog from *Sinorhizobium meliloti*, btaB (SEQ ID NO: 35).

FIG. 34 provides two-dimensional thin layer chromatograms of lipids extracted from *N. crassa* under (A) high phosphate, and (B) phosphate-limited conditions, respectively.

Figure 2:
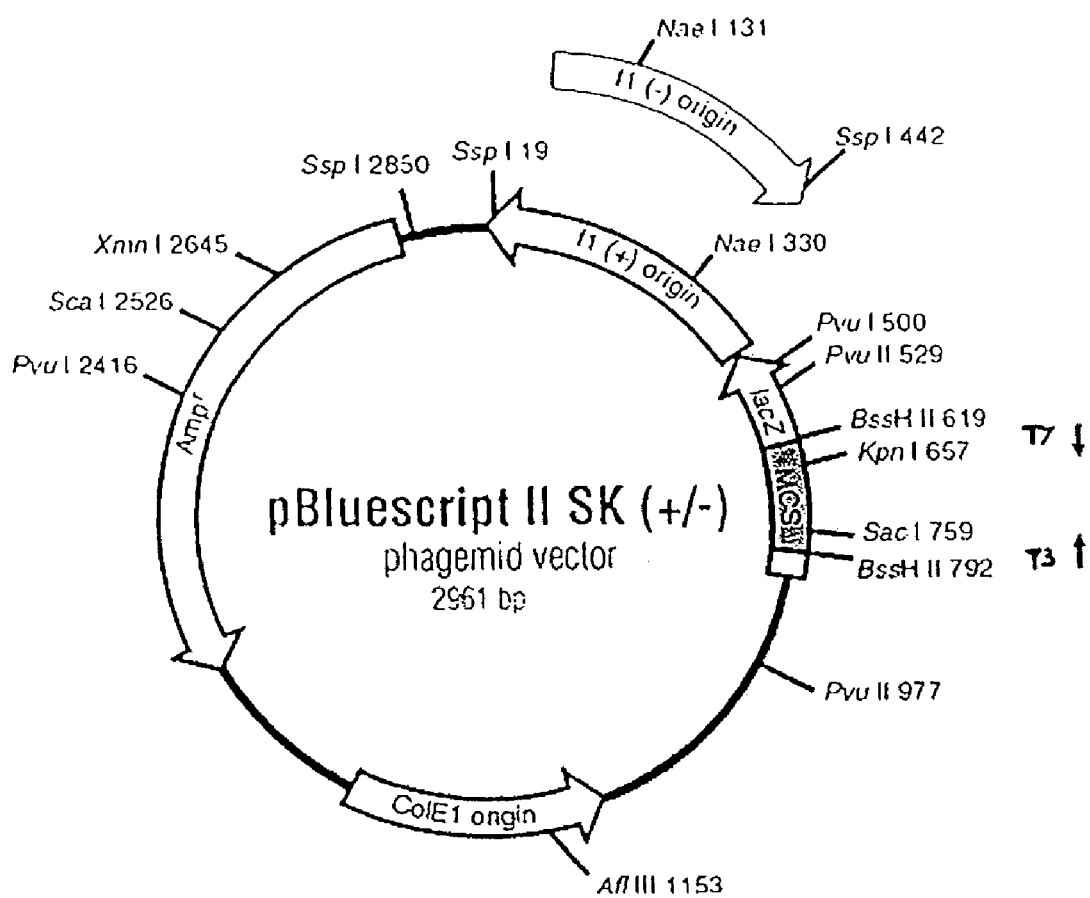
FIG. 2 schematically shows the vector map, including restriction endonuclease recognition sites, of the phagemid vector pBlueScript II-SK(+).
Figure 3:
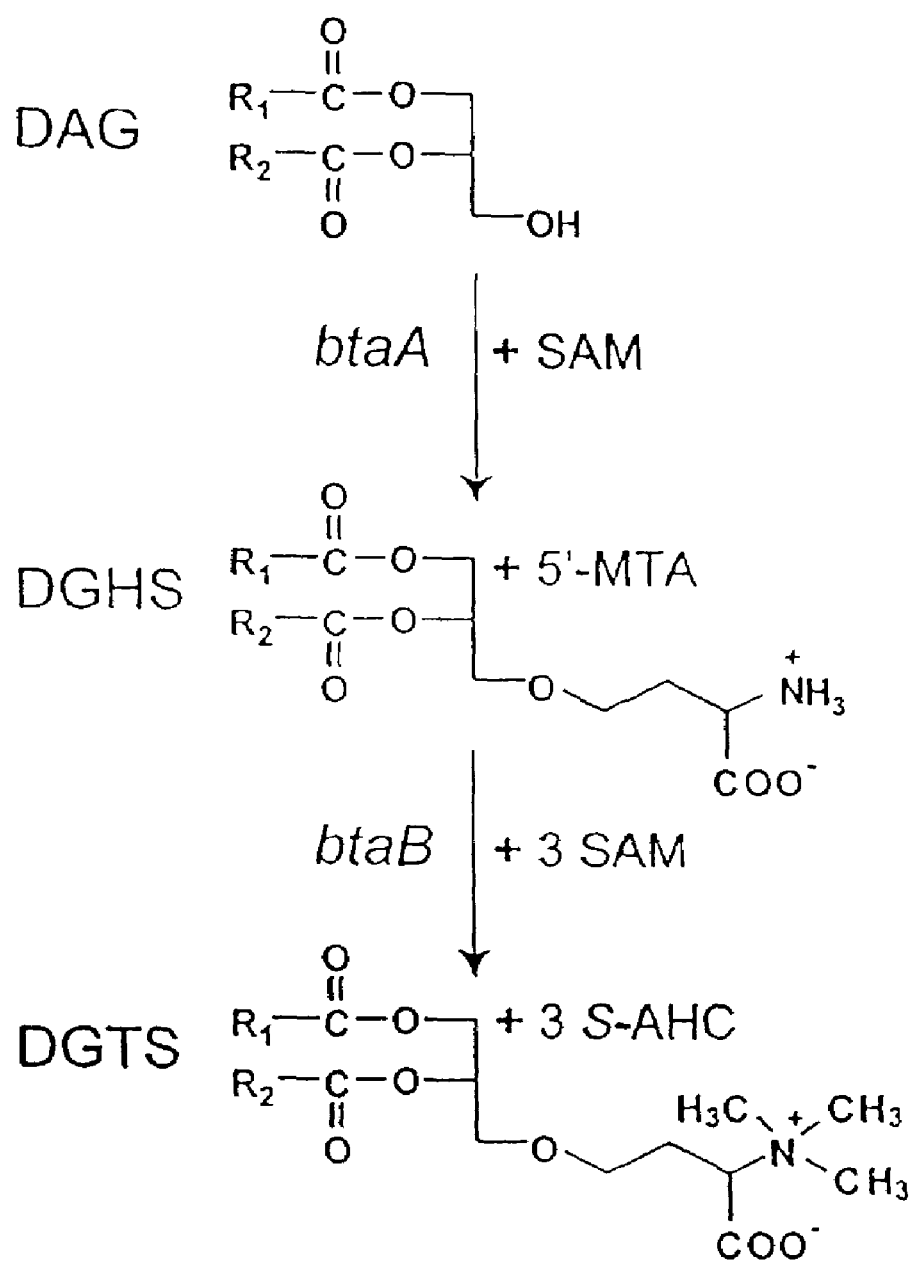
FIG. 3 schematically shows the proposed function of btaA and btaB in the biochemical pathway of DGTS biosynthesis in *R. sphaeroides*. DAG, diacylglyceryl; DGHS, diacylglycerylhomoserine; DGTS, diacylglyceryl-N,N,N-trimethylhomoserine; 5'-MTA, 5'-methylthioadenosine; SAM, S-adenosylmethionine; S-AHC, S-adenosyl homocysteine.
Figure 4:
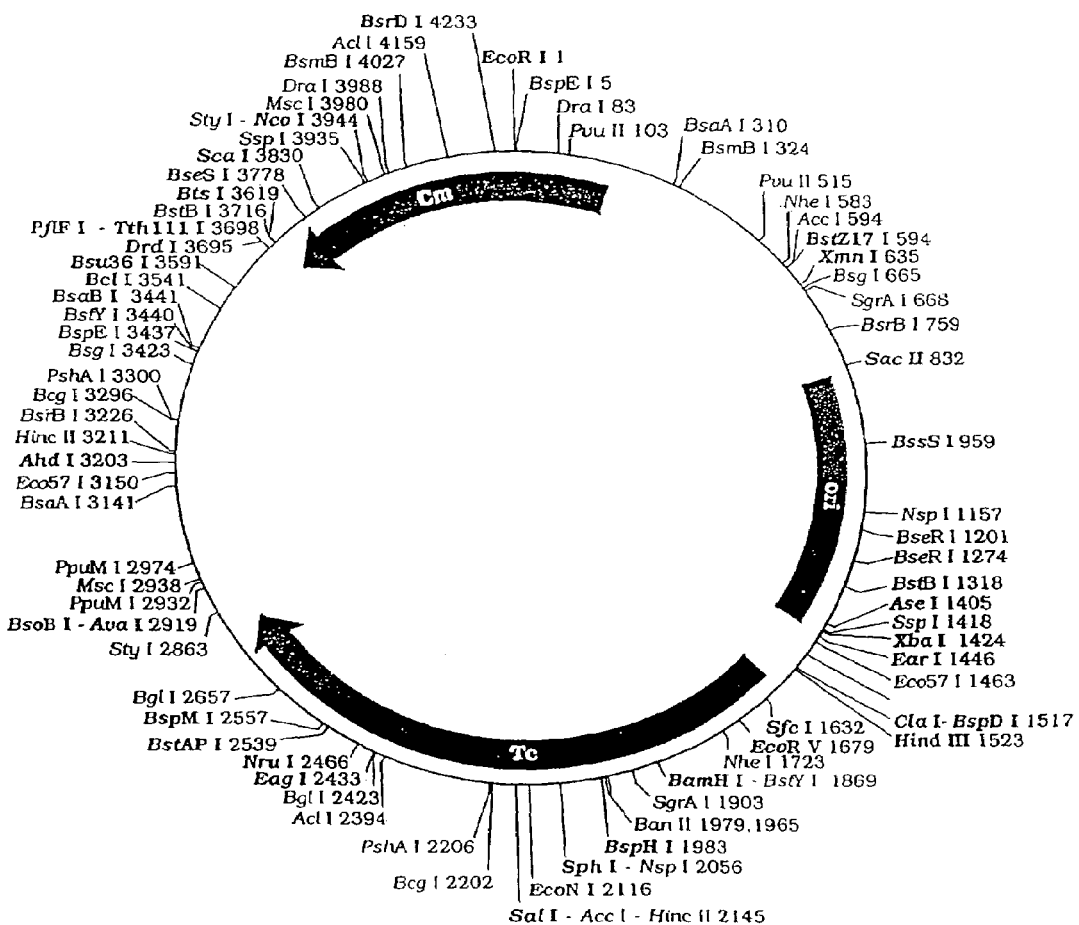
FIG. 4 schematically shows the vector map, including restriction endonuclease recognition sites, of the protein expression vector pACYC184. This plasmid is a small, low copy-number *E. coli* cloning vector that is 4,244 base pairs in length and carries tetracycline (base numbers 1580–2770) and chloramphenicol-resistance (base numbers 219–3804) genes. The map shows the location of sites for restriction enzymes that cleave the molecule once or twice; unique sites are shown in bold type. The coordinates refer to the position 5' base in each recognition sequence. Nucleotide number 1 of the vector is the first "G" of the unique EcoR1 site, "GAATTC." The map also shows the relative positions of the antibiotic resistance genes and the origin of DNA replication (ORI) at base numbers 845–847. In order to generate the vector pACYC-31, a 459-bp Xho I-Pvu II fragment including the expression cassette from pQE-31 was isolated (See FIG. 1) and ligated into the Sal I and Eco RV sites of pACYC184.

Abbreviations are as follows: DGTS, diacylglycerol-N,N,N-trimethylhomoserine; PA, phosphatidic acid; PC, phosphatidyl choline; PE, phosphatidylethanolamine; PG, phosphatidylglycerol; PI, phosphatidylinositol; and PS, phosphatidyl serine.

TABLE 1

Description of Strains and Plasmids

| Strain or Plasmid | Description or Construction |
| --- | --- |
| R. sp. 2.4.1. | wild type (ATCC #17023) |
| R. sp. RKL3 | DGTS-deficient btaA MNNG induced mutant |
| R. sp. btaB-dis | DGTS-deficient btaB disruption mutant |
| E. coli HB101 | F' Δ(mcrC-mrr) leu supE44 ara14 galK2 lacY proA2 rpsL20 (Str$^r$) xyl-5 mtl-1 recA13 |
| E. coli XL-10 Gold | Tet$^r$Δ(mcrA)183 Δ(mcrCB-hsdSMR-mrr) 173 endA1 supE44 thi-1 recA1 gyrA96 relA1 lac Hte[F' proAB lacIq ZDM15 Tn10 (Tet$^r$) Amy Cam$^r$] (Stratagene) |
| E. coli DH10B | F' mcrA Δ(mrr-hsdRMS-mcrBC) φ80dlacZDM15 ΔlacX74 deoR recA1 endA1 araD139 Δ(ara, leu)7697 galU galKl- rpsL nupG (Gibco BRL) |
| E. coli MM294 | F' endA1 hsdR17 (r$_k^-$m$_k^-$) supE44 thi-1 relA1 |
| pBluescript II SK(+) | Amp$^r$ (Stratagene) |
| pRK2013 | Kan$^r$ Tra$^+$ RK2-ColE1$_{rep}$ |
| pCHB500 | Tc$^r$; expression vector for *R. sphaerodies* |
| pUC4K | Kan$^r$ Nm$^r$; contains neomycin phosphotransferase gene of Tn903 (Pharmacia) |
| pSUP202 | Amp$^r$ Cm$^r$ Tc$^r$ pBR325$_{rep}$ |
| pRKL301 | cosmid clone complementing RKL3 |
| pRKL323 | smallest subclone of pRKL301 complementing RKL3 |
| pbtaA | nucleotides 436–1834 of pRKL323 in pCHB500 |
| pbtANT | nucleotides 633–1834 of pRKL323 in pCHB500 |
| pbtaB | nucleotides 1814–2625 of pRKL323 in pBS II SK(+) |
| pbtaB-dis | btaB inactivation cassett in pSUP202 |

Definitions

To facilitate understanding of the invention, a number of terms are defined below.

"Analog" or "Analogs," as used herein, refers to polypeptides which are comprised of a segment of at least 25 amino acids that has partial identity (i.e. comprises an amino acid sequence of greater than 50%, and more preferably 70%, homology) to a portion of the deduced amino acid sequence of SEQ ID NO: 3 or SEQ ID NO: 4, and which has (ideally) one or more properties of a transferase. The present invention contemplates utilizing the polypeptide transferases S-adenosyl methionine:diacylglycerol-3-amino-3-carboxyl transferase and S-adenosylmethionine:diacylglycerol homoserine-N-methyltransferase, to catalyze the formation of a detectable betaine lipid. The present invention also contemplates utilizing amino acid analogs (e.g. from *Mesorhizobium loti*, *Agrobacterium tumefaciens*, *Sinorhizobium meliloti*) of the polypetides encoded by SEQ ID NO: 1 and SEQ ID NO: 2.

"Associated peptide" as used herein refers to peptides that are bound directly or indirectly to other peptides. Associated peptides that are bound indirectly may have one or more peptides, or other molecules, bound between the two associated peptides. Peptides may be bound via peptide bonds, covalent bonds and non-covalent bonds. Peptides which co-precipitate are considered to be "associated peptides." For example, the present invention contemplates the co-precipitation of a polypeptide encoded by an amino acid sequence selected form the group consisting of SEQ ID NO: 3 and SEQ ID NO: 4, and peptides associated thereto.

"Expression construct," "expression vector" and "plasmid" as used herein, refer to one or more recombinant DNA or RNA sequences containing a desired coding sequence operably linked to sequences necessary for the expression of the coding sequence in a cell or host organism (e.g., mammal or plant). The sequence may be single or double stranded. The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention contemplates expression vectors comprising an oligonucleotide sequence selected from the group consisting of SEQ ID NO: 1, SEQ ID NO: 2, SEQ ID NO: 22, and SEQ ID NO: 23 (as well as homolog sequences described above).

"Reporter construct," "reporter gene" and "reporter protein" as used herein, refer to DNA or amino acid sequences, as appropriate, that, when expressed in a host cell or organism, may be detected, measured or quantitated. The present invention contemplates vectors further comprising reporter genes for easier detection of expression.

As used herein, the term "purified" or "to purify" refers to the removal of one or more (undesired) components from a sample. For example, where recombinant polypeptides are expressed in bacterial host cells, the polypeptides are purified by the removal of one or more host cell proteins, thereby increasing the percent of recombinant polypeptides in the sample. The present invention contemplates the purification of the polypeptides defined by SEQ ID NO: 3 and SEQ ID NO: 4 (and analogs thereof) by Ni-NTA/6×His affinity column purification. The term purified encompasses a large range of purities such as "partially purified," "substantially purified," and to near homogeneity.

As used herein, the term "partially purified" refers to the removal of contaminants of a sample to the extent that the substance of interest is recognizable by techniques known to those skilled in the art (e.g., by staining, blotting, etc.) as accounting for a measurable amount (e.g., picograms, nanograms, micrograms, etc.) in the mixture. The present invention is not limited to compositions that are completely purified; in some embodiments, partially purified peptides are sufficient.

As used herein, the term "substantially purified" refers to molecules, (e.g., nucleic or amino acid sequences) that are removed from their natural environment, isolated or separated, and are at least 60% free, preferably 75% free and more preferably 90% free from other components with which they are naturally associated. The present invention is not limited to compositions that are substantially purified.

As used herein, when a solution passes through the solid support matrix, it comprises the "flow through." Material that does not bind, if present, passes with the solution through the matrix into the flow through. To eliminate all non-specific binding, the matrix is "washed" with one or more wash solutions which, after passing through the matrix, comprise one or more "effluents." "Eluent" is a chemical solution capable of dissociating material bound to the matrix (if any); this dissociated material passes through the matrix and comprises an "eluate." The present invention contemplates the purification of antibodies by immobilizing peptides having the amino acid sequence of SEQ ID NO: 3 and SEQ ID NO: 4 (and/or analogs thereof) on a support matrix.

"Antibody" as used herein, refers to a glycoprotein produced by B cells and plasma cells that binds with high specificity to an antigen (usually, but not always, a peptide) or a structurally similar antigen, that generated its production. Antibodies may be produced by any of the known methodologies and may be either polyclonal or monoclonal. An antibody demonstrates specificity to the immunogen, or, more specifically, to one or more epitopes contained in the immunogen.

"Staining," as used herein, refers to any number of processes known to those in the field (typically utilizing dyes) that are used to visualize a specific component(s) and/or feature(s) of a cell or cells. For example, the present invention contemplates quantitative lipid analysis wherein lipids are stained and visualized by exposure to iodine vapor and charring.

"Nucleic acid sequence," "nucleotide sequence," and "polynucleotide sequence" as used herein refer to an oligonucleotide or polynucleotide, and fragments or portions thereof, and to DNA or RNA of genomic or synthetic origin which may be single-, or double-stranded, and represent the sense or antisense strand.

As used herein, the terms "oligonucleotides" and "oligomers" refer to a nucleic acid sequence of at least about 10 nucleotides and as many as about 200 nucleotides, preferably about 15 to 30 nucleotides, and more preferably about 20–25 nucleotides, which can be used as a primer, probe, or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., enzyme-encoding genes, transferase-encoding genes, reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

"Amino acid sequence," "polypeptide sequence," "peptide sequence," and "peptide" are used interchangeably herein to refer to a sequence of amino acids.

The term "portion" when used in reference to a nucleotide sequence refers to fragments of that nucleotide sequence. The fragments may range in size from 5 nucleotide residues to the entire nucleotide sequence minus one nucleic acid residue. The term "portion" when used in reference to an amino acid sequence refers to fragments of the amino acid sequence. The fragments may range in size from 3 amino acids to the entire amino acid sequence minus one amino acid residue. The present invention contemplates compositions comprising portions of the oligonucleotide sequence of SEQ ID NO: 1 and SEQ ID NO: 2 (or homologs thereof). In some embodiments, the portions comprise at least 50%, preferably at least 75%, more preferably at least 90%, and most preferably at least 95% of a DNA sequence selected from the group including but not limited to SEQ ID NO: 1, SEQ ID NO: 2, SEQ ID NO: 22, SEQ ID NO: 23, SEQ ID NO: 28, SEQ ID NO: 30, SEQ ID NO 32, SEQ ID NO: 34, SEQ ID NO: 44, and SEQ ID NO: 50. In other embodiments, the portions comprise at least 50%, preferably at least 75%, more preferably at least 90%, and most preferably at least 95% of an amino acid sequence selected from the group including but not limited to SEQ ID NO: 3, SEQ ID NO: 4, SEQ ID NO: 41, SEQ ID NO: 42, SEQ ID NO: 29, SEQ ID NO: 31, SEQ ID NO 33, SEQ ID NO: 35, SEQ ID NO: 45, and SEQ ID NO: 50. Particularly preferred embodiments, comprise portions of a BtaA, BtaB or Bta1 amino acid sequence (or DNA encoding said amino acid sequence) which are "biologically active."

As used herein the term "SAM binding domain" refers to an amino acid sequence which comprises a SAM binding motif (sequences shared by proteins which bind S-adenosyl-L-methionine).

The term "Bta domain" as used herein, refers to an amino acid sequence which comprises a Bta (e.g., BtaA, BtaB, Bta1, etc.) motif (sequences shared by proteins which function as S-adenosylmethionine:diacylglycerol 3-amino-3-carboxypropyl transferases.

An oligonucleotide sequence which is a "homolog" or a "variant" of a first nucleotide sequence is defined herein as an oligonucleotide sequence which exhibits greater than or equal to 50% identity, and more preferably greater than or equal to 70% identity, to the first nucleotide sequence when sequences having a length of 100 bp or larger are compared. The present invention contemplates compositions comprising homologs of the oligonucleotide sequence of SEQ ID NO:1 and SEQ ID NO: 2, and portions thereof. In some embodiments, the variants comprise at least 50%, preferably at least 75%, more preferably at least 90%, and most preferably at least 95% identity to a DNA sequence selected from the group including but not limited to SEQ ID NO: 1, SEQ ID NO: 2, SEQ ID NO: 22, SEQ ID NO: 23, SEQ ID NO: 28, SEQ ID NO: 30, SEQ ID NO 32, SEQ ID NO: 34, SEQ ID NO: 44, and SEQ ID NO: 49. In other embodiments, the variants comprise at least 50%, preferably at least 75%, more preferably at least 90%, and most preferably at least 95% identity to an amino acid sequence selected from the group including but not limited to SEQ ID NO: 3, SEQ ID NO: 4, SEQ ID NO: 41, SEQ ID NO: 42, SEQ ID NO: 29, SEQ ID NO: 31, SEQ ID NO 33, SEQ ID NO: 35, SEQ ID NO: 45, and SEQ ID NO:50. Particularly preferred embodiments, comprise variants of a BtaA, BtaB or Bta1 amino acid sequence (or DNA encoding said amino acid sequence) which are "biologically active."

As used herein, the term "biologically active" refers to a molecule having structural, regulatory and or biochemical functions of a wild type BtaA, BtaB or Bta1 molecule. In some instances, the biologically active molecule is a variant of a BtaA, BtaB or Bta1 molecule, while in other instance the biologically active molecule is a portion of a BtaA, BtaB or Bta1 molecule. Other biologically active molecules which find use in the compositions and methods of the present invention include but are not limited to mutant (e.g., variants with at least one deletion, insertion or substitution) BtaA, BtaB or Bta1 molecules. Biological activity is determined for example, by restoration or introduction of Bta (e.g., BtaA, BtaB or Bta1) activity in cells which lack Bta activity, through transfection of the cells with a bta expression vector containing a bta gene, derivative thereof, or portion thereof. Methods useful for assessing bta activity include but are not limited to reconstitution of the betaine lipid biosynthetic pathway as described in detail below in Example 2 (e.g., restoration of DGTS synthesis).

The term "DGTS synthetic activity" as used herein, refers to the enzymatic activity or activities required for the production of DGTS (diacylglycerol-N,N,N-trimethylhomoserine) from SAM (S-adenosylmethionine) and DAG (diacylglycerol). The term DGTS synthetic activity includes either or both of 1) the production of DGHS from SAM and DAG, and 2) the production of DGTS from SAM and DGHS. In some embodiments, DGTS synthetic activity is assessed by transfection of a BtaA, BtaB or Bta1 expression vector into a host cell of interest, which is cultured under phosphate limited conditions. The transfected host cells are then harvested, and lipids are extracted and resolved by thin layer chromatography.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "cloning" as used herein, refers to the process of isolating a nucleotide sequence from a nucleotide library, cell or organism for replication by recombinant techniques.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids. The present invention contemplates the hybridization of nucleic acids to the oligonucleotide sequences of SEQ ID NO: 1 and SEQ ID NO: 2, under high stringency conditions.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target. The present invention contemplates the hybridization of nucleic acids homologous to the oligonucleotide sequences of SEQ ID NO: 1 and SEQ ID NO: 2, to said sequences, under high stringency conditions.

As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence of SEQ ID NO:1 and SEQ ID NO:2, or portions thereof, will hybridize to its exact complement and closely related sequences.

Low stringency conditions comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. overnight, in a solution consisting of 5×SSPE, 1% SDS, 5× Denhardt's reagent and 100 µg/ml denatured salmon sperm DNA followed by washing in a solution comprising 0.1×SSPE and 0.1% SDS at 68° C., when a probe of about 100 to about 1000 nucleotides in length is employed. Other suitable highly stringent conditions include but are not limited to hybridization in 0.5 M NaHPO$_4$, pH 7.2, containing 1% BSA, 5% SDS at 65° C. overnight, followed by washing twice with 40 mM NaHPO$_4$, pH 7.2, containing 1% SDS, at 65° C.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize to the single-stranded nucleic acid sequence under conditions of low stringency as described above.

As used herein, the term "variant" or "variants" refers to analogs of the naturally occurring R. sphaeroides proteins S-adenosylmethionine:diacylglycerol 3-amino-3-carboxyl transferase and S-adenosylmethionine:diacylglycerolhomoserine-N-methyltransferase that differ in amino acid sequence or in ways that do not involve sequence, or both. Non-sequence modifications include in vivo or in vitro chemical derivatization of S-adenosyl methionine:diacylglycerol 3-amino-3-carboxyl transferase and S-adenosylmethionine:diacylglycerol homoserine-N-methyltransferase. Non-sequence modifications also include changes in acetylation, methylation, phosphorylation, carboxylation, or glycosylation. Preferred variants include S-adenosyl methionine:diacylglycerol 3-amino-3-carboxyl transferase and S-adenosylmethionine:diacylglycerolhomoserine-N-methyltransferase (or biologically active fragments thereof) whose sequences differ from the wild-type sequence by one or more conservative amino acid substitutions, or by one or more non-conservative amino acid substitutions, deletions, or insertions which do not abolish the biological activity of S-adenosylmethionine:diacylglycerol 3-amino-3-carboxyl transferase and S-adenosylmethionine:diacylglycerolhomoserine-N-methyltransferase.

Conservative substitutions typically include the substitution of one amino acid for another with similar characteristics, e.g., substitutions within the following groups: (Group I) acidic ((D) aspartate, (E) glutamate); (Group II) basic ((K) lysine, (R) arginine, (H) histidine); (Group III) nonpolar ((A) alanine, (V) valine, (L) leucine, (I) isoleucine, (P) proline, (F) phenylalanine, (M) methionine, (W) tryptophan); and (Group IV) uncharged polar ((G) glycine, (N) asparagine, (O) glutamine, (C) cysteine, (S) serine, (T) threonine, (Y) tyrosine). Phenylalanine, tryptophan, and tyrosine are sometimes classified jointly as aromatic amino acids. Conservative amino acid substitutions as contemplated by the present invention are presented in the following formula well-known in the field of art: "X$_1$ZX$_2$, " wherein X$_1$ is the single-letter code for the amino acid residue present in the wild-type amino acid sequence (as indicated in SEQ ID NOS: 3 & 4), Z is the number of the amino acid residue being changed as a reflection of the amino acid sequence of SEQ ID NO: 3 or SEQ ID NO: 4, and X$_2$ is the single-letter code of the amino acid residue to which X$_1$ is being changed (e.g. I141L would indicate the changing of the isoleucine residue, at amino acid position 141, to a leucine residue). The present invention contemplates variants of the peptides encoded by SEQ ID NO: 3 and SEQ ID NO: 4 comprising a conservative amino acid substitution.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the T$_m$ of the formed hybrid, and the G:C ratio within the nucleic acids. The present invention contemplates the hybridization of nucleic acids and proteins to the oligonucleotide sequences of SEQ ID NO: 1 and SEQ ID NO: 2, and portions thereof.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., C$_0$t or R$_0$t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "T$_m$" is used in reference to the "melting temperature." The melting temperature is the temperature at which a population of double-stranded nucleic acid molecules becomes half dissociated into single strands. The equation for calculating the T$_m$ of nucleic acids is well known in the art. As indicated by standard references, a simple estimate of the T$_m$ value may be calculated by the equation: T$_m$=81.5+0.41(% G+C), when a nucleic acid is in aqueous solution at 1 M NaCl (see e.g., Anderson and Young, Quantitative Filter Hybridization, in *Nucleic Acid Hybridization* [1985]). Other references include more sophisticated computations which take structural as well as sequence characteristics into account for the calculation of T$_m$. The present invention contemplates the hybridization of nucleic acids comprising the oligonucleotide sequences of SEQ ID NO: 1 and SEQ ID NO: 2, and portions thereof, at the T$_m$ and above.

"Amplification" is defined herein as the production of additional copies of a nucleic acid sequence and is generally carried out using polymerase chain reaction technologies well known in the art (see, e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence (e.g. in a mixture of genomic DNA) without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. The present invention contemplates the amplification of nucleic acid comprising SEQ ID NO: 1 and SEQ ID NO: 2, and portions thereof. The present invention contemplates the amplification of nucleic acids which are homologous to SEQ ID NO: 1 and SEQ ID NO: 2, and portions thereof.

The terms "reverse transcription polymerase chain reaction" and "RT-PCR" refer to a method for reverse transcription of a RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. The present invention contemplates portions of the oligonucleotide sequences of SEQ ID NO: 1 and SEQ ID NO: 2 as useful for primers in DNA sequencing and PCR.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label. The present invention contemplates portions of the oligonucleotide sequences of SEQ ID NO: 1 and SEQ ID NO: 2 as useful for probes in hybridization analysis (e.g. colony hybridization screening, Northern Blot, etc.) and PCR.

As used herein, the terms "restriction endonucleases" and "restriction enzymes" refer to bacterial enzymes, each of which cut double- or single-stranded DNA at or near a specific nucleotide sequence. Restriction maps for the various vectors contemplated by the present invention are found in FIGS. 1, 2, 4, 12, and 13.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity (i.e. operably linked) to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

The term "promoter," "promoter element," or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "host cell" or "cell," as used herein, refers to any cell which is used to express a "gene of interest," e.g. btaA and btaB. "Host cell" or "cell" also refers to any cell which is used in any of the screening assays for detection of the production of betaine lipids. The present invention contemplates host cells (e.g. bacteria, yeast, and plants) comprising the oligonucleotide sequence of SEQ ID NO: 1 and SEQ ID NO: 2, and portions thereof.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and antisense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" (or "GTG" in some organisms) which encodes the initiator methionine and on the 3' side by one of the three triplets which specify stop codons (i.e., TAA, TAG, TGA).

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein. The present invention contemplates transgenic cells comprising the oligonucleotide sequence of SEQ ID NO: 1 and SEQ ID NO: 2, and portions thereof.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. Heterologous DNA is not endogenous to the cell into which it is introduced, but has been obtained from another cell. Heterologous DNA also includes an endogenous DNA sequence which contains some modification (e.g. a conservative amino acid substitution). Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene. For example, the introduction of a gene having an oligonucleotide sequence selected from the group of SEQ ID NO: 1 and SEQ ID NO: 2 into a plant is the introduction of a foreign gene into a plant.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., S-adenosylmethionine:diacylglycerol 3-amino-3-carboxyl transferase and S-adenosylmethionine:diacylglycerol-homoserine-N-methyltransferase) encoded by the transgene (e.g., the btaA and btaB genes, respectively) as demonstrated herein [e.g., quantitative analysis of lipid extracts to detect the production of DGTS]. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. "Functionally stable transformants" refers to stable transformants that continue to express their incorporated transgenes. The present invention contemplates both stable and transient transformants comprising the oligonucleotide sequence of SEQ ID NO: 1 and SEQ ID NO: 2, and portions thereof.

A "transformed cell" is a cell or cell line that has acquired the ability to grow in cell culture for many multiple generations, the ability to grow in soft agar and the ability to not have cell growth inhibited by cell-to-cell contact. In this regard, "transformation" refers to the introduction of foreign genetic material into a cell or organism. Transformation may be accomplished by any method known which permits the successful introduction of nucleic acids into cells and which results in the expression of the introduced nucleic acid. "Transformation" methods include, but are not limited to, such methods as microinjection, electroporation, and DNA particle "bombardment." Transformation may be accomplished through use of any expression vector. For example, the use of *Agrobacterium tumefaciens* to introduce foreign nucleic acid (e.g. having the oligonucleotide sequence of SEQ ID NO: 1 and SEQ ID NO: 2, and portions thereof) into plant cells is contemplated. Additionally, transformation refers to cells that have been transformed naturally, usually through genetic mutation.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogens* (which causes hairy root disease in infected host plants).

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle bombardment as described herein.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture.

The term "embryonic cell" as used herein in reference to a plant cell refers to one or more plant cells (whether differentiated or undifferentiated) which are capable of differentiation into a plant tissue or plant. Embryonic cells include, without limitation, protoplasts such as those derived from the genera *Fragaria*, *Lotus*, *Medicago*, *Onobrychis*, *Trifolium*, *Trigonella*, *Vigna*, *Citrus*, *Linum*, *Geranium*, *Manihot*, *Daucus*, *Arabidopsis*, *Brassica*, *Raphanus*, *Sinapis*, *Atropa*, *Capsicum*, *Hyoscyamus*, *Lycopersicon*, *Nicotiana*, *Solanum*, *Petunia*, *Digitalis*, *Majorana*, *Ciohorium*, *Helianthus*, *Lactuca*, *Bromus*, *Asparagus*, *Antirrhinum*, *Hererocallis*, *Nemesia*, *Pelargonium*, *Panicum*, *Pennisetum*, *Ranunculus*, *Senecio*, *Salpiglossis*, *Cucumis*, *Browaalia*, *Glycine*, *Lolium*, *Zea*, *Triticum*, *Sorghum*, and *Datura*. Also included are embryos (such as those from sorghum, maize, banana), embryonic meristems (such as those from soybean), embryogenic callus (such as from sugarcane), protocorm-like bodies (such as from pineapple), and embryogenic cells as exemplified by those from garlic. The ability of an embryonic cell to differentiate into a plant is determined using methods known in the art. For example, differentiation of pineapple protocorm-like bodies into shoots may be accomplished by culturing the protocorm-like body on agar-solidified hormone-free modified Murashige & Skoog (MS) medium or on agar-solidified PM2 medium (U.S. Pat. No. 6,091,003 hereby incorporated by reference). Differentiation into pineapple roots may be accomplished by culture of protocorm-like bodies in liquid modified MS medium containing 1 mg/L NAA.

The term "conjugation" as used herein refers to the process in which genetic material is transferred from one microorganism to another involving a physical connection or union between the two cells. This process is commonly known to occur in bacteria, protozoa, and certain algae and fungi.

DETAILED DESCRIPTION OF THE INVENTION

The present invention relates to compositions and methods for the production of betaine lipids. The compositions of the present invention comprise isolated and purified DNA having an oligonucleotide sequence selected from the group consisting of SEQ ID NO: 1 and SEQ ID NO: 2, and portions thereof (as well as the homologs described above, and portions thereof). The methods of the present invention comprise the expression of recombinant enzymes (e.g. from *Rhodobacter sphaeroides*) in host cells (e.g. in bacteria and plants) to produce betaine lipid compounds including, but not limited to, Diacylglyceryl-O-4'-(N,N,N,-trimethyl) homoserine (DGTS). The compositions and methods of the present invention allow a reduction in the amount of plant cell membrane-associated phosphorus by replacing phosphorous lipids with non-phosphorous lipids. Thus, the overall amount of phosphate-containing fertilizer required for the growth of the plant is reduced.

Polar lipids are essential components of all biological membranes. Most common are glycerolipids containing a diacylglycerol moiety to which a polar head group is attached. A head group can be a carbohydrate moiety as in the very abundant plant galactolipids or a phosphorylester as in the glycerophospholipids, the most common lipid class in animals. Betaine lipids represent a third class of glycerolipids in which a quaternary amine alcohol is bound in an ether linkage to the diacylglycerol moiety. Betaine lipids are structural components of membranes in ferns, mosses, algae, and bacteria. The overall structure of betaine lipids resembles to some extent that of the glycerophospholipid phosphatidylcholine (PC). Although the phase transition temperature for betaine lipid is slightly higher compared to PC with identical fatty acid composition, the physical phase behavior of betaine lipid in mixtures with water is similar to that of PC.

Figure 11:
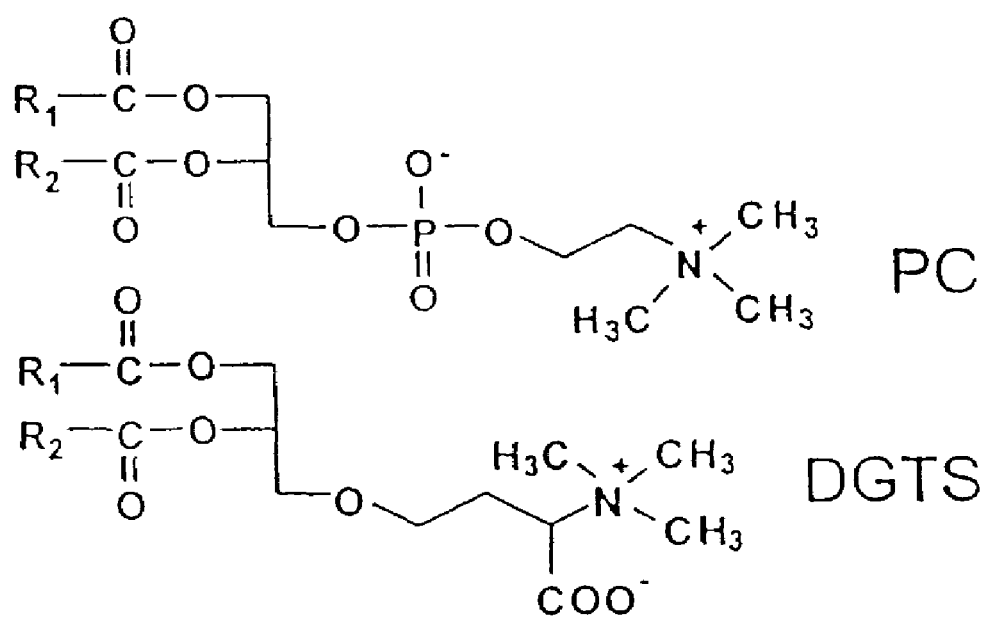
FIG. 11 shows the structures of phosphatidylcholine (PC) and diacylglyceryl-N,N,N-trimethylhomoserine (DGTS). R1 and R2 represent the hydrocarbon chains' respective acyl groups.
Figure 12:
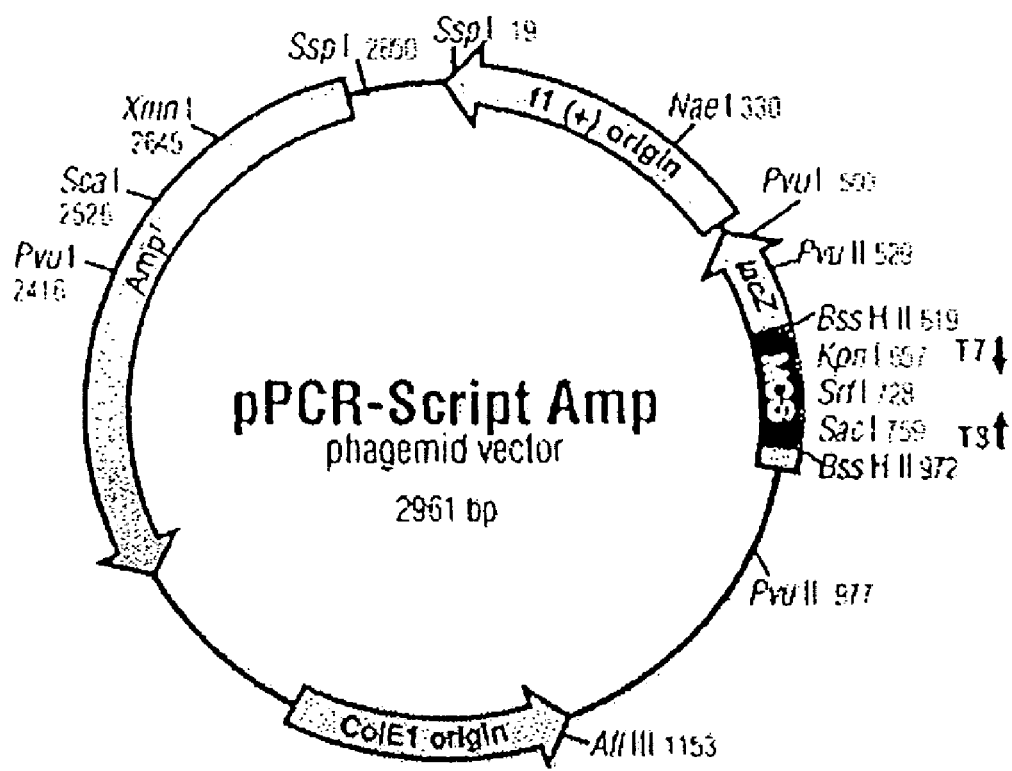
FIG. 12 schematically shows the vector map, including restriction endonuclease recognition sites, of the phagemid vector pPCR-Script Amp.
Figure 13:
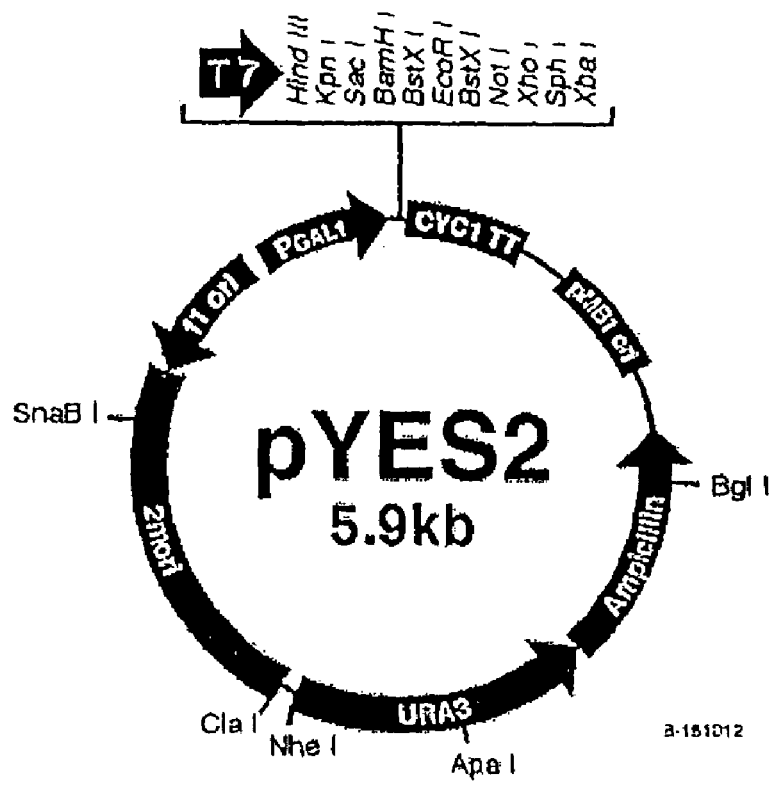
FIG. 13 schematically shows the vector map, including restriction endonuclease recognition sites, of the yeast expression vector pYES2.

The betaine lipid diacylgycerol-N-trimethylhomoserine (DGTS) is similar in structure to the common phosphoglycerolipid, phosphatidylglycerol (PC) (See FIG. 11), but lacks phosphorous. PC plays an important and central role in lipid metabolism in seed plants. However, many organisms alter their lipid composition in response to chemical or physical changes of the environment, permitting the organism to survive unfavorable conditions. For example, DGTS replaces PC to the extent that PC is actually absent in some algae. Thus, DGTS could take over these functions in organisms lacking PC.

Plants depend much less on phospholipids than animals. Recent discoveries indicate that plants are able to replace phospholipids with non-phosphorous glycolipids to conserve phosphate under phosphate-limiting growth conditions. Agricultural phosphate overfertilization creates environmental problems and will lead to a depletion of naturally occurring phosphate fertilizer resources in the near future. Therefore, it is highly desirable to develop new strategies to reduce the amount of phosphate fertilizer needed for the optimal growth of crop plants. The invention illustrates such a strategy by providing compositions and methods that reduce the amount of plant cell membrane-associated phosphorus (which represents approximately 30% of all organic phosphorus in a plant cell) by replacing the phosphorous lipids with non-phosphorous lipids.

The present invention is not limited by any specific reaction mechanism, and indeed it is not necessary to understand any particular underlying mechanism in order to practice the invention. It is believed that the production of the betaine lipid, DGTS, is driven by the activity of the *R. sphaeroides* btaA gene product, S-adenosyl methionine:diacylglycerol 3-amino-3-carboxyl transferase, coupled with the activity of the *R. sphaeroides* btaA gene product, S-adenosylmethionine:diacylglycerol homoserine-N-methyltransferase.

I. Cloning and Expression of the *R. sphaeroides* btaA and btaB Genes in *E. coli*

The present invention provides methods for the production of betaine lipids, including but not limited to DGTS, wherein the btaA (SEQ ID NO: 1) and btaB (SEQ ID NO: 2) genes of *R. sphaeroides* are cloned into, and expressed in, *Escherichia coli* cells. Although the present invention is not limited to a specific method whereby said genes are cloned and expressed in *E. coli*, in one embodiment, said genes are cloned and expressed as follows.

A. Cloning

1. Growth of *R. sphaeroides* Cell Cultures

Although the present invention is not limited to a specific method of growing cell cultures of *R. sphaeroides*, in one embodiment, said cell cultures are grown, and genomic DNA is isolated and purified therefrom, as follows.

Cell cultures were grown in the malate-basal-salt medium as described by Ormerod et al., "Light-dependent utilization of organic compounds and photoreduction of molecular hydrogen by photosynthetic bacteria; relationships with nitrogen metabolism," *Arch. Biochem. Biophys.*, 94: 449–463 (1961), or Sistrom's succinate-basal-salt medium. (See Sistrom W. R., "A requirement of sodium in the growth of *R. sphaeroides*," *J. Gen. Microbiol.*, 22:778–785 (1960); Sistrom W. R., "The kinetics of the synthesis of photopigments in *R. sphaeroides*," *J. Gen. Microbiol.* 28: 607–616 (1962). Agar plates (1.5% agar) were either incubated in the dark at 30° C. in air or in the light (100 µE m$^{-2}$ s$^{-1}$) at 30–35° C. in an atmosphere containing 5% $CO_2$ and 95% $N_2$. When required, 0.8 µg/ml tetracycline was added to agar plates containing Sistrom's medium. Aerobic chemoheterotrophic, liquid cultures inoculated with a single colony were incubated at 30° C. with shaking in Erlenmeyer flasks. Anaerobic photoheterotrophic, liquid cultures were grown in tightly-closed, filled, 200 ml bottles, in the light (100 µE m$^{-2}$ s$^{-1}$) at 30–35° C. The bottles are mixed for aeration once or twice a day by manual shaking.

2. Preparation of Genomic DNA from *R. sphaeroides*

Although the present invention is not limited to a specific method of purifying nucleic acids from *R. sphaeroides*, in one embodiment, genomic DNA is isolated and purified from *R. sphaeroides* as follows. The DNA prepared by this method is suitable for endonuclease restriction, Southern Blotting, and PCR applications.

*R. sphaeroides* cells are grown as noted above and 3 ml of the bacterial culture is centrifuged at 10,000×g in a 1.5 mL polypropylene tube. The bacterial cell pellet is resuspended in 1 ml TE buffer (Tris-Cl, 50 mM; EDTA, 1 mM; pH 8.0). The cells are re-centrifuged, followed by resuspension of the pellet in 1 mL TE buffer containing 1% SDS, 0.5 mg/mL Proteinase K. The cells are incubated for 1 hour at 37° C. To shear the genomic DNA, the sample is extruded from a syringe through a G20-1.5 needle. The DNA preparation is sequentially extracted with an equal volume of phenol, phenol/chloroform (1:1, v/v), and chloroform/isoamylalcohol (24:1, v/v), a technique that is well known in the field of art. The DNA is precipitated by adding 0.3 volumes of 3 M sodium acetate (pH 5.2) and 2 volumes of 200 proof ethanol to the extracted DNA. The DNA is pelleted by centrifugation at 15,000×g in a microcentrifuge for 2 minutes. The DNA pellet is air-dried and resuspended in 0.1 mL TE-buffer.

3. PCR of BtaA and BtaB from Genomic DNA and Cloning of the PCR Product into a Bacterial Expression Vector In one embodiment, in order to clone the btaA and btaB genes of *R. sphaeroides* into *Escherichia coli*, *R. sphaeroides* genomic DNA (isolated and purified as indicated above) is subjected to Polymerase Chain Reaction (PCR) such that the genomic sequences for btaA and btaB are respectively generated.

In order to amplify the btaA gene, a forward primer having the nucleotide sequence 5'-ACA TGC ATG CAG TGA CGC AGT TCG CCC TC-3' (SEQ ID NO: 36), and a reverse primer having the nucleotide sequence 5'-CGG GGT ACC AGG ACG ATC CGC TCG AAC CG-3' (SEQ ID NO: 37), were used such that Bam H1 and Hind III sites were provided for cloning into the bacterial expression vector pPCR-Script Amp (Stratagene Cat. No. 211188), a derivative of pBlueScript SK+. The forward primer amplifies the beginning of the gene, including the Val start site (GTG) (See FIG. 7: SEQ ID NO: 1). The reverse primer includes the stop codon of the btaA gene in the resulting PCR product. PCR products are run on 1% Tris-Acetate-EDTA (TAE) agarose gel in the presence of ethidium bromide and excised for purification by QIAEX II gel extraction kit (Qiagen Cat. No. 20021), followed by cloning into the SrfI site of pPCR-Script Amp (as described in the manufacturer's instructions). The resulting plasmid construct allows the expression of the recombinant btaA gene product in *E. coli*.

In order to amplify the btaB gene, a forward primer having the nucleotide sequence 5'-ACA TGC ATG CAG TGA CGC AGT TCG CCC TC-3' (SEQ ID NO: 36), and a reverse primer having the nucleotide sequence 5'-CGG GGT ACC AGG ACG ATC CGC TCG AAC CG-3' (SEQ ID NO: 37), were used such that Sph I and Kpn I sites were provided for cloning into pPCR-Script Amp. The forward primer amplifies the beginning of the gene, including the Met start site (ATG) (See FIG. 8: SEQ ID NO: 2). The reverse primer includes the stop codon of the btaB gene in the resulting PCR product. PCR products are run on 1% TAE agarose gel in the presence of ethidium bromide and excised for purification by QIAEX II gel extraction kit followed by cloning into the SrfI site of pPCR-Script Amp (as described in the manufacturer's instructions). The resulting plasmid construct allows the expression of the recombinant btaB gene product in E. coli.

In an alternative embodiment, the btaA and btaB genes are amplified as indicated above, but are cloned into a pBluescript II SK+ phagemid vector (Stratagene Cat. No. 212205). Both the vector and the PCR products are digested with the appropriate restriction endonucleases (i.e. digested with Bam H1 and Hind III for btaA, or digested with Sph I and Kpn I for btaB) prior to ligation to allow direct cloning of the products into the vector.

B. Expression of the btaA and btaB Gene Products

The present invention is not limited to a specific method of expressing the btaA and btaB gene products from R. sphaeroides (i.e. the proteins encoded by the amino acid sequences found in SEQ ID NO: 3 and SEQ ID NO: 4, respectively). However, in one embodiment, the invention contemplates the expression of the R. sphaeroides btaA and btaB gene in E. coli.

1. Cloning of btaA and btaB PCR Inserts into E. coli Expression Vectors pQE-31 and pACYC-31

In one embodiment, btaA and btaB genes generated from PCR (as described above) are cloned into either the pQE-31 (FIG. 1)(QIAGEN Cat.# 32915) or pACYC-31 vectors. The vector pACYC-31 is described in the publication Dormann et al., "Arabidopsis galactolipid biosynthesis and lipid trafficking mediated by DGD1," Science, 284: 2181–2184. (See FIG. 4). Said vectors are digested with Sph I and Kpn I (for btaA) or Bam HI and Hind III (for btaB), and gel purified using the QIAEX II gel extraction kit (Qiagen Cat. No. 20021). The btaA PCR insert is excised from pBlueScript SK+ by Sph I/Kpn I digest and gel purified as above. The btaB PCR insert is released from the pBlueScript SK+ vector by Bam HI/Hind III digestion and is then gel purified. The inserts and vectors are ligated together with T4 DNA ligase, a technique well-known in the field of art. Ligation reactions are then transformed into electroporation-competent E. coli XL 1-Blue (Stratagene Cat. No. 200228) and plated onto LB Ampicillin plates (i.e. for pQE-31) or LB Chloramphenicol plates (i.e. for pACYC-31).

Each construct is analyzed individually for protein expression (as detailed in the Qiagen QIAexpress System literature) using E. coli M15[pREP4] (QIAGEN Cat. No. 34210) as an expression host for the pQE-31 based plasmids and XL1-Blue as the host for pACYC-31 based constructs. Since the pACYC-31 and pQE-31 vectors carry compatible origins of replication, reconstitution of the DGTS biosynthetic pathway is achieved by concurrent expression of pACYC-31:BtaA and pQE-31:BtaB, or pACYC-31:BtaB and pQE-31: BtaA in XL1-Blue. Transformed E. coli cells are grown and subsequently analyzed by TLC (as described below) for DGTS production after induction with 1–5 mM isopropyl-β-D-thiogalactoside (IPTG) (Amersham Pharmacia Biotech, Piscataway, N.J.: Cat. No. 27-3054-03).

The present invention is not limited to the use of any specific protein expression vector or system. In one embodiment, the protein expression vector is selected from the group comprising pQE-9, pQE-16, pQE-30, pQE-31, pQE-32, pQE-40, pQE-60, pQE-70, pQE-80, pQE-81, pQE-82, pQE-100 (all available from QIAGEN, Inc., Valencia, Calif.). In another embodiment, the protein expression vector is selected from the group comprising pACYC-31 and pACYC184 (New England Biolabs, Beverly, Mass.: Cat. No. E4152S).

The present invention is not limited to any specifc means of purifying recombinant R. sphaeroides btaA and btaB gene products. In one embodiment, the resulting plasmid constructs, pQE-31: BtaA and pQE-31:BtaB, allowed the expression of their respective recombinant R. sphaeroides bta gene products in E. coli. Moreover, said plasmid constructs allow the purification of said gene products due to the selective binding of the six N-terminal histidine residues (i.e. 6xHis tag) of the plasmid construct to nickel nitriloacetic acid (Ni-NTA) agarose resin, following the manufacturer's instructions. (QIAGEN, Inc., Valencia, Calif.: Cat. No. 30210). The recombinant R. sphaeroides bta gene products are eluted with 200 mM imidazole (which was subsequently removed by use of a Millipore Ultrafree 4 concentrator (Millipore, Inc., Bedford, Mass.)) and stored in a buffer comprising glycerol, NaCl, and $NaH_2PO_4$ (pH 7.5) at $-20°$ C.

2. Expression of BtaA and BtaB in Yeast Using the pYES2 System

It is not intended that the present invention be limited solely to the expression of the btaA and btaB gene products from R. sphaeroides in E. coli. In one alternative embodiment, the present invention contemplates the expression of said gene products, resulting in the production of betaine lipids (including but not limited to DGTS) in yeast as follows.

In order to amplify the btaB gene from R. sphaeroides genomic DNA (isolation as described above), a forward primer having the nucleotide sequence 5'-GCA AAG CTT AGC ATG GCC GAC GCC ACC CAT-3' (SEQ ID NO: 8), and a reverse primer having the nucleotide sequence 5'-GCA GGA TCC CTC TCA CCG CGT GAG CGT G-3' (SEQ ID NO: 9), were used such that BamH1 and Hind III sites were provided for cloning into the yeast expression vector pYES2 (Invitrogen Cat. No. V825-20).

In order to amplify the btaA gene from R. sphaeroides genomic DNA (isolation as described above), a forward primer having the nucleotide sequence 5'-CGG GGT ACC ATG GCG CAG TTC GCC CTC-3' (SEQ ID NO: 9), and a reverse primer having the nucleotide sequence 5'-ACA TGC ATG CAG GAC GAT CCG CTC GAA CCG-3' (SEQ ID NO: 10), were used such that Sph I and Kpn I sites were provided for cloning into pYES2.

The reaction mixtures and thermal cycling conditions are the same as those noted below in the Examples. PCR products are run on a 1% TAE agarose gel in the presence of ethidium bromide and excised for purification by QIAEX II gel extraction kit, followed by ligation into the appropriate restriction sites of pYES2 (i.e. Sph I and Kpn I sites or Bam H1 and Hind III sites). Ligation reactions are transformed into XL-1 Blue cells, and the resultant constructs purified and transformed into INVSc1 ura3 yeast cells (Invitrogen Cat. No. V825-20) as described in the pYES2 product literature. The resulting plasmid constructs allow the expression of the recombinant btaA and btaB gene products in yeast.

Yeast cells transformed by this method are grown and subsequently analysed by TLC (as described below) for DGTS production after induction with 2% galactose-containing medium.

3. Co-Expression of *R. sphaeroides* btaA and btaB Gene Products

It is not intended that the invention be limited to the independent expression of a peptide having the amino acid sequence selected from the group of SEQ ID NO: 3 and SEQ ID NO: 4, or portions thereof, in a single host organism or plant. In one embodiment, the invention contemplates the co-expression of both of the peptides described above in a single host organism or plant. In one embodiment, co-expression of the peptides encoded by an amino acid sequence selected from the group consisting of SEQ ID NO: 3 and SEQ ID NO: 4 (for example, in separate protein expression vectors) in *E. coli*, such that a betaine lipid biosynthetic pathway (e.g. produces DGTS) is reconstituted, is contemplated as follows.

In order to express two proteins in *E. coli*, two compatible plasmids with the ability to express proteins, one for btaA and one for btaB, are utilized. Each plasmid must have a different antibiotic resistance marker in order to select for transformants with the correct combination of plasmids. The plasmid pQE-31 provides ampicillin resistance, whereas the plasmid, pACYC-31, provides chloramphenicol resistance. The btaA and btaB genes from *R. sphaeroides* are cloned into pQE-31 and pACYC-31 as described above. The M15 cell line (QIAGEN, Inc., Valencia, Calif.) is transformed with a pQE-31/btaA protein expression construct (as described above). The pACYC-31/btaB expression construct is transformed into the M15 cell line containing the pQE-31/btaA expression vector. Upon induction of expression with 1–5 mM isopropyl-β-D-thiogalactoside (IPTG) (Amersham Pharmacia Biotech, Piscataway, N.J.: Cat. No. 27-3054-03), both proteins are expressed.

C. Detection of Betaine Lipid Production

It is not intended that the present invention be limited by any specific means of detecting the production of betaine lipids, including but not limited to DGTS, by the compositions and methods contemplated herein. In one embodiment, detection of the production of betaine lipids comprises thin layer chromatography and visualization with iodine vapor. In another embodiment, detection of the production of betaine lipids comprises quantitative lipid analysis wherein reaction products are isolated from the TLC plates and used to prepare fatty acid methyl esters. The methyl esters are quantified by gas chromatography using myristic acid as the internal standard. In an alternative embodiment, detection of the production of betaine lipids comprises lipid extraction followed by fast atom bombardment-mass spectroscopy (FAB-MS).

1. Detection of DGTS Production by Thin Layer Chromatography (TLC)

Figure 5:
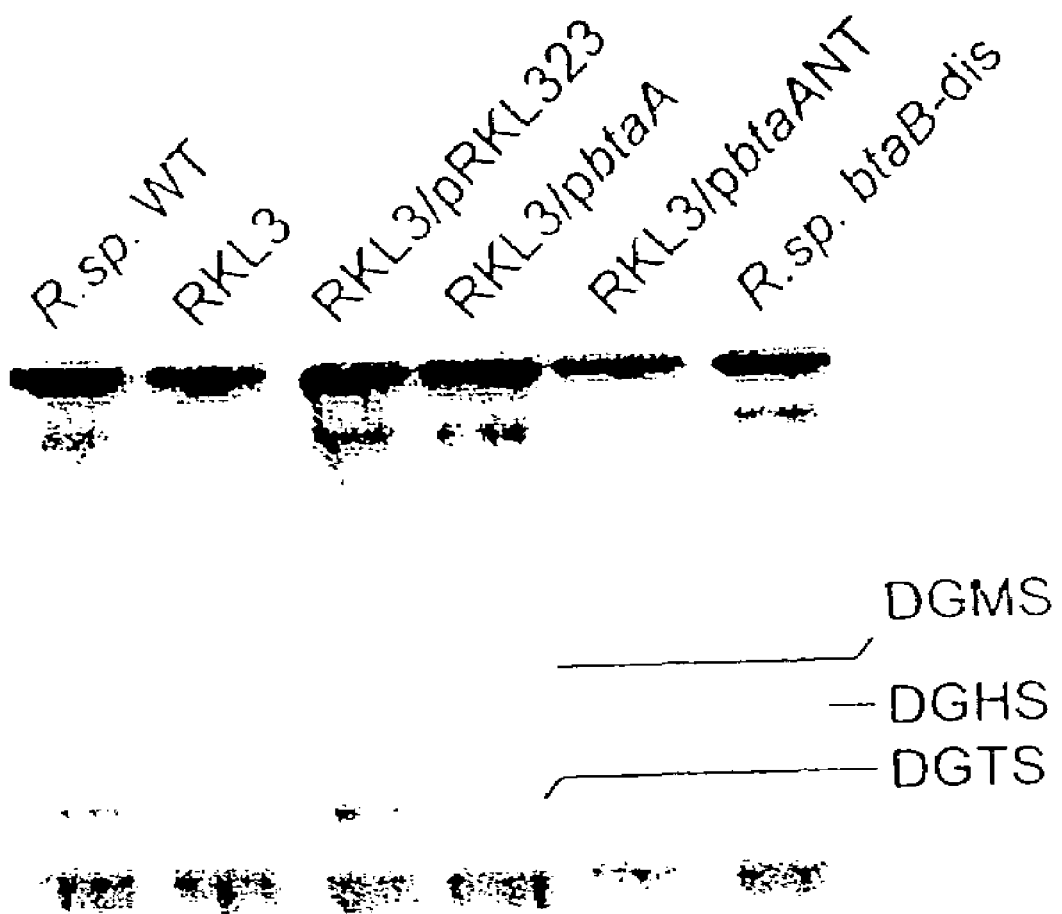
FIG. 5 depicts a comparison of lipid extracts from different strains of *R. sphaeroides*. All cells were grown under phosphate-limited conditions at an initial $P_i$-concentration of 0.1 mM. A one-dimensional thin-layer chromatogram stained by iodine vapor is shown. The indicated strains and plasmids are described in Table 1. DGHS, diacylglycerylhomoserine; DGMS, diacylglyceryl-N-monomethyl homoserine; DGTS, diacylglyceryl-N,N,N-trimethylhomoserine.

Randomly chosen colonies from a population of *R. sphaeroides* cells known to produce the lipid, DGTS, are streaked as small patches (0.5 by 0.5 cm) on fresh Z-broth plates. Lipids are isolated from these patches by collecting cells onto the wide end of a flat toothpick and swirling the material in 75 µl of chloroform-methanol (1:1, vol/vol) contained in polypropylene microcentrifuge tubes. Following the addition of 25 µl of 1 N KCl-0.2 M $H_3PO_4$, the tubes are vortexed and centrifuged to separate the organic and aqueous phases. A 10 µl aliquot is withdrawn from the lipid-containing lower phase and directly spotted onto an activated ammonium sulfate-impregnated silica gel thin layer chromatography (TLC) plate for one-dimensional lipid separation. For this purpose, Baker Si250 silica plates with a pre-adsorbent layer are prepared by soaking in 0.15 M ammonium sulfate for 30 seconds, followed by air drying to complete dryness. Immediately prior to use, the plates are activated for 2.5 h at 120° C. Activation of ammonium sulfate-treated plates at 120° C. produces sulfuric acid, which protonates phosphatidylglycerol, making it less polar. An acetone-benzene-water mixture (91:30:8, vol/vol/vol) is employed as the solvent system. Lipids were visualized by spraying the plates with 50% sulfuric acid followed by heating at 160° C. for 10 to 15 minutes to char the lipids. (See FIG. 5).

2. Quantitative Lipid Analysis to Verify the Production of DGTS

It is not intended that the present invention be limited to any specific method of verifying the production of betaine lipids including, but not limited to, DGTS. In one embodiment, a method for quantitative lipid analysis of lipids produced by the present invention is contemplated as described in Benning C. & Somerville C. R., "Isolation and Genetic Complementation of a Sulfolipid-Deficient Mutant of *Rhodobacter sphaeroides*," *J. Bacteriol.*, 174: 2352–2360 (1992).

For each strain, three 50-ml cultures were grown aerobically in Sistrom's medium (as described above) with shaking at 32° C. in the dark. The cells were grown under phosphate-limited conditions at an initial $P_i$ concentration of 0.1 mM. The cells were centrifuged, suspended in 0.5 ml of water, and extracted by vortexing with 4 ml of chloroform-methanol (1:1, vol/vol). Addition of 1.3 ml of 1 M KCl-0.2 M $H_3PO_4$, vortexing, and centrifugation resulted in phase partitioning of the lipids into the lower chloroform phase. The chloroform phase was removed and concentrated to 0.2 ml by evaporation under a stream of $N_2$. The sample was split, and the material was spotted onto activated (30 min at 110° C.) silica TLC plates (Si250; Baker). The plates were developed in two dimensions, first with chloroform-methanol-water (65:25:4, vol/vol/vol), and then with chloroform-acetone-methanol-acetic acid-water (50:20:10:10:5, by volume).

Figure 6:
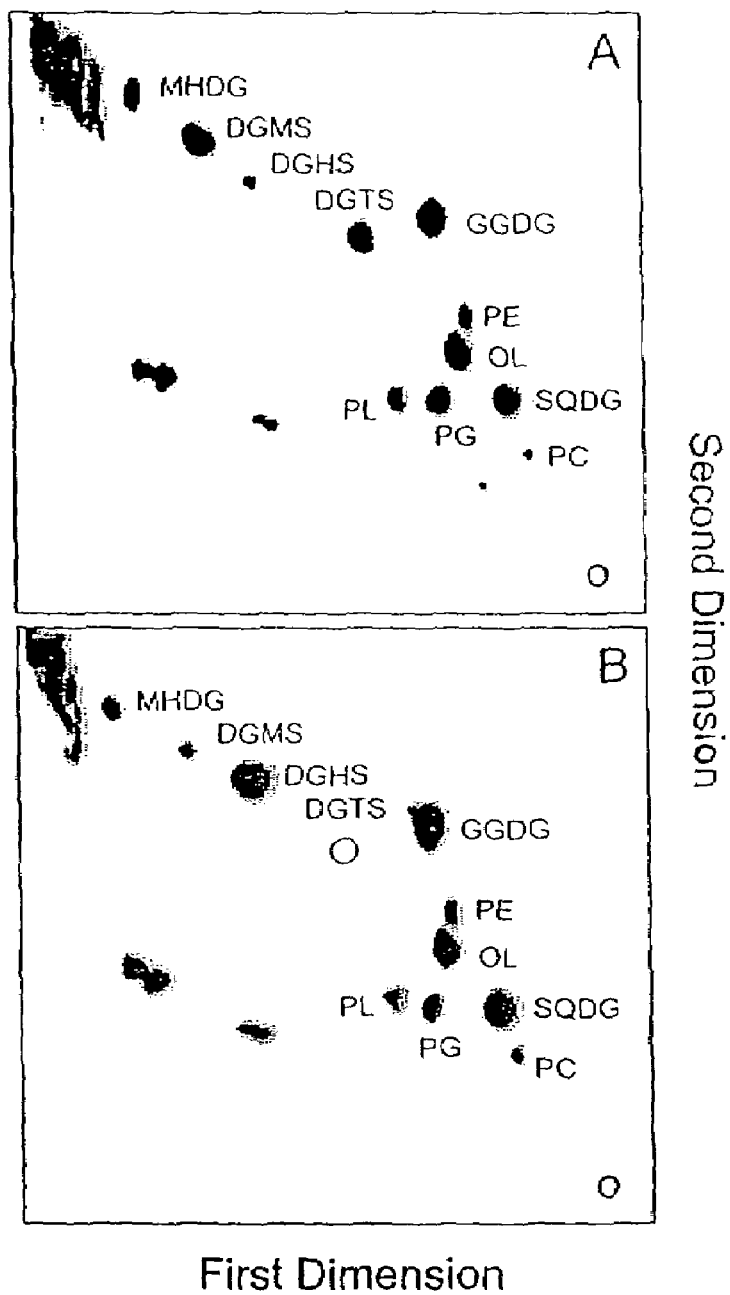
FIG. 6 depicts a two-dimensional thin layer chromatogram indicating the lipid phenotype of RKL3 containing pbtaA (A) and a mutant disrupted in btaB (B). The cells were grown under phosphate-limited conditions at an initial $P_i$-concentration of 0.1 mM. Abbreviations are as defined in the legend to Table 2.

Lipids were visualized with iodine vapor (See FIG. 6), and after desorption of iodine, the spots were individually scraped into 8-ml screw-cap tubes. To the samples, 5 µg of myristic acid methyl ester in 0.1 ml of hexane was added as an internal standard, since only negligible amounts of endogenous myristic acid are found in the bacterial lipids. Fatty acid methyl esters were prepared by addition of 1 ml of anhydrous 1 N methanolic HCl (Supelco) followed by incubation at 80° C. for 1 h. Following the addition of 1 ml of 0.95% (wt/vol) KCl, the fatty acid methyl esters were extracted into 1 ml of hexane and then dried to a volume of 0.1 ml.

Samples (2 µl each) were injected onto a gas chromatograph (Varian 2000) which was equipped with a 2.4-m column (2-mm inner diameter) packed with 3% SP-2310 and 2% SP-2300 on 100/120 Chromosorb WAW (Supelco). The carrier gas ($N_2$) flow rate was adjusted to 20 ml/min, and the column temperature was set for 2 min at 180° C., increasing to 200° C. over 10 min, and 4 min at 200° C.

The fatty acid methyl esters were detected by a flame ionization detector, and the data were integrated by a Spectra Physics integrator. To calculate the relative amounts of the polar lipids included in the analysis, the amount of fatty acids contained in each lipid of a particular sample was calculated from the resulting gas chromatogram based on the following formula: [(total area under all peaks−standard peak area)/standard peak area]×5 µg. The relative amount for each lipid in the sample was expressed as a percent of all lipids analyzed (See, Table 2). The validity of calculation was based on the assumption that each of the lipids, including the unidentified lipids, contain two fatty acids per molecule, and that the different lipids have a similar fatty acid composition.

TABLE 2

Lipid Composition of R. sphaeroides Wild Type and RKL3 Following Phosphate Deprivation

| Lipid | WT (mol %) | | RKL3 (mol %) | |
|---|---|---|---|---|
| MHDG | 1.3 | ±0.2 | 12.7 | ±1.6 |
| DGTS | 15.9 | ±1.7 | ND | |
| MPE | ND | | 0.9 | ±0.2 |
| GGDG | 32.6 | ±2.4 | 36.7 | ±2.8 |
| PE | 1.5 | ±0.1 | 7.5 | ±0.4 |
| OL | 21.2 | ±3.6 | 15.2 | ±0.1 |
| PG | 4.7 | ±0.6 | 7.5 | ±0.4 |
| SQDG | 17.5 | ±0.9 | 14.5 | ±0.7 |
| PC | 0.1 | ±0.1 | 1.1 | ±0.6 |
| PL | 5.3 | ±0.5 | 3.7 | ±0.2 |

Mean values from three independent cultures (0.1 mM $P_i$) and standard errors are shown. Abbreviations: DGTS, diacylglycerol-N,N,N-trimethylhomoserine; GGDG, glucosylgalactosyldiacylglycerol; MHGD, monohexosyldiacylglycerol; MPE, N-monomethylphosphatidylethanolamine; ND, not detected; OL, ornithine lipid; PC, phosphatidyl choline; PE, phosphatidylethanolamine; PG, phosphatidylglycerol; PL, undefined phospholipid; SQDG, sulfoquinovosyldiacylglycerol.

3. Confirmation of Betaine Lipid Production by FAB-MS and $^1$H-Nuclear Magnetic Resonance It is not intended that the present invention be limited any specific method of confirming betaine lipid production. In one embodiment, a method for confirming the production of the betaine lipid, DGTS, is contemplated comprising fast atom bombardment mass spectroscopy (FAB-MS) and $^1$H-NMR-spectroscopy as described in Benning et al., "Accumulation of a Novel Glycolipid and a Betaine Lipid in Cells of *Rhodobacter sphaeroides* Grown Under Phosphate-Limitation," *Arch. Biochem. Biophys.*, 317: 103–111 (1995). Lipids produced by the present invention (e.g. DGTS) may be analyzed by FAB-MS and $^1$H-NMR-spectroscopy and compared to the predicted values for a range of lipids, and more specifically, betaine lipids, in order to confirm production of the desired lipid.

FAB-MS measurements were done at the MSU-NIH Mass Spectrometry Facility using a JEOL HX-110 double focusing mass spectrometer (JEOL USA, Peabody, Mass.) operating in the negative ion mode (for glycolipids) or in the positive ion mode (for betaine lipids). Approximately 1 µg of lipid was mixed with 1 µl of matrix; either triethanolamine for glycolipids, or glycerol/15-crown-5 (2:1, v/v) for the betaine lipid. Ions were produced by bombardment with a beam of Xe atoms (6 keV). The accelerating voltage was 10 kV and the resolution was set at 1000. Exact mass measurements were obtained by peak matching at a resolution of ca. 10,000 to either a matrix ion or an ion of a reference compound added to the sample.

Briefly, the fatty acid composition of the Dragendorff-positive lipid (i.e. DGTS) accumulating in phosphate-starved cells of R. sphaeroides was determined. With cis-$\Delta^{11}$-octadecenoyl (vaccenoyl) at 87.5 mol % as the predominant fatty acid, simple patterns for mass- and $^1$H-NMR-spectroscopy of purified DGTS samples containing a mixture of molecular species were expected. Positive mode FAB-MS indicated DGTS had molecular ion, [M+H]+, at m/z 764. By high resolution FAB-MS peak matching to a reference ion ([M+H]+ at m/z 734.4691 for $C_{37}H_{67}NO_{13}$) of erythromycin mixed in the sample, a mass of 764.6370 was measured for the molecular ion of DGTS. This value is in agreement with the formula $C_{46}H_{86}NO_7$ (4.5 ppm error from the calculated mass of 764.6404 for the [M+H]+ ion of a N-trimethyl homoserine betaine lipid containing two acyl functions corresponding to a total fatty acid composition of 36:2, e.g. two vaccenoyl residues. Vaccenic acid was the predominant fatty acid in DGTS as determined by GC-analysis. The mass spectrum revealed a fragment at m/z 500 resulting from the loss of water and one 18:1 acyl group. An abundant fragment at m/z 236 of the MS/MS spectrum was interpreted as the result of a loss of two water molecules and two 18:1 acyl chains. A third fragment at m/z 162 representing the betaine head group, most likely resulted from elimination of glycerol minus water (propenediol) from the fragment m/z 236. Negative ion mode FAB-MS of DGTS was unsuccessful, as would be expected from a molecule carrying a net positive charge.

H-NMR analyses were performed in a Varian VXR500 spectrometer (500 MHz for protons) at 25° C., in $CD_3OD$ for the glycolipid and in $CD_3OD/CDCl_3$ (1:1 vol/vol) for the betaine lipid. The concentrations for the lipids were approximately 1 mg/ml. One-dimensional $^1$H-spectra were measured using a 30–90° tipping angle for the pulse and 0.2 seconds as a recycle delay between each of the 64 acquisitions. The chemical shifts are expressed in ppm downfield from an external standard of $Me_4Si$ and actually measured by reference to internal $CH_3OH$ (3.59 ppm) or $CHCl_3$ (7.24 ppm). Two-dimensional COSY—($^1$H-$^1$H correlated spectroscopy) and HMQC—(heteronuclear multiple quantum correlation spectroscopy) spectra were recorded using standard procedures.

Briefly, in order to confirm the structure of the betaine lipid accumulating in *R. sphaeroides*, a $^1$H-NMR was recorded for the purified compound. This spectrum was found to be nearly identical to published $^1$H-NMR spectra for N-trimethylhomoserine betaine lipid purified from the fern *Adiantum capillus-veneris* L. or the unicellular algae *Dunaliella parva* with the exception of the complexity for the fatty acid specific resonances due to different acyl groups in the different samples. The $^1$H-NMR spectra for DGTS showed resonance values for the fatty acyl chains (0.6–2.5 ppm) and the glycerol protons (H-2 5.12 ppm, H-1$_a$ 4.35 ppm, H-1$_b$ 4.13 ppm, H-3$_a$ 3.59 ppm, and H-3$_b$ 3.55 ppm), thereby suggesting a diacylglycerol structure for the lipid. The protons of the N,N,N-trimethyl group gave rise to a strong resonance at 3.18 ppm typical for all betaine lipids (See Sato, N., and Furuya, M., *Plant Cell Physiol.*, 21: 1113–1120 (1983); Evans et al., *Chem. Phys. Lipids*, 31: 331–338 (1982); and Vogel et al., *Chem. Phys. Lipids*, 52: 99–109 (1990)).

II. Expression of the *R. sphaeroides* btaA and btaB Genes in Plants

The present invention also contemplates the expression of the *R. sphaeroides* btaA and btaB genes in plants. Although the present invention is not limited to the expression of said genes in any specific plant, in one embodiment, the expression of the *R. sphaeroides* btaA and btaB genes in *Arabidopsis* is provided as follows.

A. Cloning and Expression of the *R. sphaeroides* btaA and btaB Genes in Transgenic Plants Transfer and expression of transgenes in plant cells is now routine practice to those skilled in the art. It has become a major tool to carry out gene expression studies and to attempt to obtain improved plant varieties of agricultural or commercial interest. The present invention is not limited to the expression of the recombinant *R. sphaeroides* peptides encoded by SEQ ID NO: 1 and SEQ ID NO: 2 in bacteria and yeast. The invention also contemplates the expression of recombinant *R. sphaeroides* btaA (SEQ ID NO: 1) and btaB (SEQ ID NO: 2) genes in transgenic plants through agrobacterial transformation as described by S. Clough and A. Bent, "Floral dip: a simplified method for Agrobacterium-mediated transformation of *Arabidopsis thaliana*," *Plant J.*, 16: 735–43 (1998).

In one embodiment, the general process for manipulating genes to be transferred into the genome of plant cells to result in the expression of a recombinant peptide is carried out in two phases. First, all the cloning and DNA modification steps are done in *E. coli*, and the plasmid containing the gene construct of interest is transferred by conjugation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria (e.g., streptomycin), and the other for selection in plants (e.g., a gene encoding for kanamycin resistance or a gene encoding for resistance to an herbicide such as hygromycin). Also present are restriction endonuclease sites for the addition of one or more transgenes operably linked to appropriate regulatory sequences and directional T-DNA border sequences which, when recognized by the transfer functions of *Agrobacterium*, delimit the region that will be transferred to the plant.

In another embodiment, plant cells may be transformed by shooting into the cell, tungsten microprojectiles on which cloned DNA is precipitated. (See, e.g., Gordon-Kamm et al., *Plant Cell*, 2: 603 (1990)). In one embodiment, the Biolistic Apparatus (Bio-Rad, Hercules, Calif.) is used for the shooting with a gunpowder charge (22 caliber Power Piston Tool Charge) or an air-driven blast driving a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the present invention the target can be any plant cell, tissue, seed, or embryo. The DNA introduced into the cell on the microprojectiles becomes integrated into either the nucleus or the chloroplast.

It is not intended that the present invention be limited to the particular manner by which the expression of any specific recombinant *R. sphaeroides* peptide in plants is achieved. In one embodiment, a peptide encoded by the nucleic acid sequences as set forth in SEQ ID NO: 1 is expressed in plants. In another embodiment, a peptide encoded by the nucleic acid sequence as set forth in SEQ ID NO: 2 is expressed in plants. In a further embodiment, two recombinant *R. sphaeroides* peptides encoded by the group of nucleic acid sequences comprising SEQ ID NO: 1 and SEQ ID NO: 2 are co-expressed in plants.

It is not intended that the present invention be limited by any particular plant cell type in which to generate the expression of recombinant *R. sphaeroides* gene products. In one embodiment, the plant cell is derived from a monocotyledonous plant. In an alternative embodiment, the plant cell is derived from a dicotyledonous plant. In another embodiment, the plant cell is derived from a group comprising the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea*. In a preferred embodiment, the plant cell is derived from *Arabidopsis thaliana*.

B. Detection of Betaine Lipid Production in Plants

It is not intended that the present invention be limited to any specific method of detecting the production of betaine lipids (including but not limited to DGTS) in plants. In one embodiment, the production of betaine lipids in plants is monitored by TLC as described above. In another embodiment, said detection comprises the isolation of plant nucleic acids and Northern Blot Hybridization Analysis as described below.

1. Isolation of Total RNA from *Arabidopsis thaliana* Tissues

It is not intended that the invention be limited by any specific method to isolate total RNA from *A. thaliana* tissues. In one embodiment, total RNA is isolated from said tissues by guanidine hydrochloride extraction as follows. Said tissues are frozen in liquid nitrogen and homogenized to a fine powder using a Waring blender. For small amounts of tissue (less than 0.5 g), a rotating pin in a 1.5-ml Eppendorf tube is used to homogenize the tissue. The extract is homogenized further at room temperature by the addition of 2 volumes of a guanidine buffer comprising 8 M guanidine hydrochloride, 20 mM MES (4-morpholineethansulfonic acid), 20 mM EDTA, and 50 mM 2-mercaptoethanol at pH 7.0.

The guanidine hydrochloride extract is centrifuged in a precooled (4° C.) centrifuge for 10 minutes at 10,000 rpm. Subsequently the RNA-containing supernatant is filtered through one layer of cheesecloth to get rid of floating particles. At least 0.2–1.0 vol of phenol/chloroform/IAA is added to extract proteins. After extraction the mixture is centrifuged for 45 minutes at 10,000 rpm at room temperature to separate the phases. The RNA-containing aqueous phase is collected and mixed with pre-cooled 0.7 volumes of ethanol and 0.2 volumes of 1 M acetic acid for precipitating the RNA and leaving DNA and residual proteins in the supernatant. An overnight incubation at −20° C., or a 1 hour incubation at −70° C., is recommended.

The precipitated RNA is pelleted at 10,000 rpm for 10 min and washed twice with sterile 3 M sodium acetate at pH 5.2 at room temperature. Low-molecular-weight RNAs and contaminating polysaccharides dissolve, whereas intact RNA stays as a pellet after centrifugation for 5 minutes at 10,000 rpm. The salt is removed by a final wash with 70% ethanol and the RNA pellet is subsequently dissolved in sterile water and stored at 20° C. until needed. In the event that the total RNA isolated as described above requires further enrichment and purification prior to Northern Blot Hybridization Analysis, said RNA may be subjected to Poly A+ mRNA isolation as described below.

2. Poly A+ mRNA Isolation from *Arabidopsis thaliana* Total RNA

The present invention is not limited to any specific means of isolating Poly A+ mRNA from the total RNA of *Arabidopsis thaliana* leaves. In one embodiment, Poly A+ mRNA was isolated from *A. thaliana* leaf total RNA with the Oligotex mRNA Mini Kit (QIAGEN Cat. No. 70022) following the manufacturer's instructions as follows.

The Oligotex Suspension is heated to 37° C. in a heating block, mixed by vortexing, and placed at room temperature. A sample containing 0.25 mg of *A. thaliana* leaf total RNA is pipetted into an RNase-free 1.5-ml microcentrifuge tube, and the volume of the reaction is adjusted to 0.25 ml with RNase-free water. A volume of 0.25 ml of Buffer OBB and 0.015 ml of Oligotex Suspension are added to the reaction. The contents are mixed thoroughly by pipetting. The sample incubated for 3 minutes at 70° C. in a water bath or heating block in order to disrupt secondary structure of the RNA. The sample is removed from the heating block, and placed at room temperature (20 to 30° C.) for 10 minutes to allow hybridization between the oligo dT30 of the Oligotex particle and the poly-A tail of the mRNA. The Oligotex:mRNA complex is pelleted by centrifugation for 2 minutes at maximum speed (14,000–18,000×g), and the supernatant is removed by pipetting.

The Oligotex:mRNA pellet is resuspended in 400 µl Buffer OW2 by vortexing, and pipetted onto a small spin column supplied with the kit. The spin column is centrifuged for 1 minute at maximum speed (14,000–18,000×g). The spin column is transferred to a new RNase-free 1.5-ml microcentrifuge tube, and 400 µl of Buffer OW2 is applied to the column. The spin column is centrifuged for 1 minute at maximum speed and the flow-through fraction is discarded.

The spin column is transferred to another 1.5-ml microcentrifuge tube. A volume of 20–100 µl hot (70° C.) Buffer OEB is pipetted onto the column. The resin is resuspended by pipetting up and down three or four times to allow elution of the mRNA, and centrifuged for 1 minute at maximum speed to pellet the suspension. The flow-through fraction, which contains the Poly A+ mRNA is isolated and stored at −20° C. until it is used.

3. Northern Blot Hybridization Analysis

Although the present invention is not limited to any specific method of performing Northern Blot analysis for detecting the production of betaine lipids (including but not limited to DGTS) in plants, in one embodiment, said analysis is performed as follows.

Prior to preparation of an agarose gel for Northern Blot Analysis, the electrophoresis chamber, gel tray, and gel comb are soaked in 1:10 diluted bleach for 30 min to 1 h. An agarose gel comprising 2.25 g of Agarose, 110 ml of $H_2O$, 15 ml of 10× MEN buffer (10× MEN: 41.9 g MOPS-NaOH, 4.1 g NaOAc, 3.72 g EDTA, pH 7.0, H2O to 1000 ml, DEPC, autoclaved), 25 ml of 37% formaldehyde (Merck Cat. No. 3999) is prepared. The gel is poured into a 14 cm×14 cm gel tray, and a 10-14 sample comb is inserted into the agarose gel.

Total RNA samples from plant tissue, isolated as described above, is prepared for electrophoresis as follows. For each sample, approximately 10 to 20 mg of RNA (in a volume of 20 µl) is mixed with 4 µl 10× MEN, 6 µl 37% formaldehyde, 20 µl fresh formamide, 0.5 µl 10 mg/ml ethidium bromide, 0.5 µl 1 mg/ml bromophenol blue (in DEPC-treated water) to a total sample volume of 51.1 µl. The samples are incubated for 10 min at 56° C., and then placed on ice until loaded into the agarose gel. The samples are loaded into the gel sample wells prior to adding 1000 ml of electrophoresis buffer (1× MEN). The gel is electrophoresed at 100 Volts (constant voltage). After 15 min, when the samples have entered the gel (ca. 1 cm), the gel is submerged in the 1× MEN buffer. The gel is run at 100 Volt, for 3 to 5 h, until the blue dye has migrated up to ⅔ of the gel. The gel is removed from the electrophoresis chamber and photographed.

The Northern Blot of the gel assembly is prepared by placing one 14 cm×14 cm sheet of hybridization membrane (Hybond N+ from Amersham), two 14 cm×14 cm sheets of filter paper (Whatman 3MM), and two 15 cm×25 cm sheets of filter paper, on top of the gel. The sequence of placement of the filter papers and membrane are as follows. Prior to placement on the gel, the filter papers are moistened with 10×SSC, and the hybridization membrane is soaked in distilled water. The gel chamber is filled with 500 ml 10×SSC. The two 15 cm×25 cm sheets of filter paper are placed in the gel chamber, and the agarose gel is placed upside-down on top of the sheets. The hybridization membrane is placed on top of the gel. The two 14 cm×14 cm sheets of filter paper are placed on top of the membrane. Finally, paper towels are placed on top of the 14 cm×14 cm sheets of filter paper, and a piece of plastic (e.g. gel tray) is placed on top of the assembly with a glass bottle (100 to 500 g) to act as a weight. The assembly is left to blot the RNA from the gel overnight. Note that 10×SSC buffer may be prepared by making a 1:2 dilution of 20×SSC (175.3 g NaCl, 88.2 g Na citrate, pH 7.0, distilled water to 1000 ml, DEPC-treated and autoclaved) in DEPC-treated water.

The next day, the membrane is removed from the gel and marked in the upper right corner with the date. The membrane is air-dried for 15 min. The membrane is fixed incubating in 50 mM NaOH for 5 min. Alternatively, the membrane may be baked for 2 h at 80° C. in a vacuum oven. Prior to pre-hybridization, the membrane is washed in 2×SSC for 2 min.

The membrane is placed in a 30 cm hybridization tube (Biometra) with pre-hybridization buffer comprising 250 mM $Na_xPO_4$, pH 7.4, 7% Sodium dodecyl sulfate (SDS), 1 mM EDTA, 1% Bovine Serum Albumin (BSA), 150 µl of a 10 mg/ml herring sperm DNA solution (denatured at 95° C. for 3 min), and distilled water. The membrane is allowed to pre-hybridize for at least 4 hours prior to hybridization at 68° C.

Prior to hybridization, a radio-labeled hybridization probe is prepared as follows. A DNA fragment comprising a nucleotide sequence selected from the group consisting of SEQ ID NO: 1 (btaA) and SEQ ID NO: 2 (btaB), and portions thereof, is labeled by random-priming with fresh $^{32}$P-dCTP (58 µCi, 3000 Ci/mol) using the Megaprime DNA labeling kit (Amersham Cat. No. RPN 1606-5-6-7) as per the manufacturer's instructions. The radio-labeled probe is added directly to the hybridization tube containing the pre-hybridization solution and membrane. The membrane is allowed to hybridize overnight at 68° C.

Upon completion of hybridization, the membrane is washed 2×SSC, 0.1% SDS at 68° C. in the hybridization tube for 5 min. The membrane is then removed from the tube and washed, in a glass or plastic container, 2–3 additional times for approximately 15 min each until the wash buffer is no longer radioactive. Once washing is completed, the membrane is placed in a plastic bag and exposed to X-ray film in a film cassette with an intensifying screen for 12–72 hours at −70° C. RNA samples which contained sequences homologous to the radio-labeled probe are visualized upon development of the X-ray film. A positive signal indicates that the plant from which the RNA sample was isolated produces RNA transcripts homologous to a nucleotide sequence selected from the group consisting of SEQ ID NO: 1 (btaA) and SEQ ID NO: 2 (btaB), and thus, indicates that the plant produces betaine lipids including, but not limited to, DGTS.

III. Method for the Production of DGTS in vitro

The methods of the present invention comprise the utilization of compositions comprising isolated and purified DNA having an oligonucleotide sequence selected from the group consisting of the R. sphaeroides btaA (SEQ ID NO: 1) and btaB (SEQ ID NO: 2) genes, and portions thereof, such that DGTS is produced. In one embodiment, the production of the betaine lipid DGTS from a reaction mixture comprising isolated and purified protein having an amino acid sequence selected from the group consisting of SEQ ID NO: 3 and SEQ ID NO: 4, and portions thereof, is contemplated.

In one embodiment, the R. sphaeroides btaA and btaB genes are cloned into pQE-31 and pACYC-31, respectively, and expressed in E. coli as described above. Next, the btaA gene product (i.e. a first peptide), and the btaB gene product (i.e. a second peptide), are substantially purified using the QIAexpress Ni-NTA/6×His-tag system as described above. Following purification of said peptides, DGHS (a betaine lipid precursor) is produced in a reaction containing means by reacting 50 mM Bicine (N,N,-bis(2-hydroxyethyl) glycine), pH 8.1, 10 mM $MgCl_2$, 1 mM cysteine, 100 μM S-adenosylmethionine (SAM), 100 μM diacylglycerol, and 10 μg of a substantially purified first peptide encoded by the amino acid sequence set forth in SEQ ID NO: 3, in a 100 μl reaction volume at 37° C. for 40 minutes. Next, 10 μg of a substantially purified second peptide encoded by the amino acid sequence set forth in SEQ ID NO: 4 and 100 μM SAM are added to the above reaction mixture such that DGTS is produced. (See, e.g., Arondel et al., "Isolation and Functional Expression in *Escherichia coli* of a Gene Encoding Phosphatidylethanolamine Methlytransferase (EC 2.1.1.17) from *Rhodobacter sphaeroides*," *J. Biol. Chem.*, 268(21): 16002–16008 (1993). In another embodiment, said first peptide is a gene product encoded by the nucleic acid sequence set forth in SEQ ID NO: 22 (Ml-btaA). In another embodiment, said second peptide is a gene product encoded by the nucleic acid sequence set forth in SEQ ID NO: 23 (Ml-btaB).

The present invention is not limited by a specific means for verifying the production of DGTS by the method described above. The production of DGTS as a reflection of S-adenosylmethionine:diacylglycerol-3-amino-3-carboxyl transferase and S-adenosylmethionine:diacylglycerol homoserine-N-methyltransferase activity is detected by Quantitative Lipid Analysis as described above. In another embodiment, the production of DGTS is verified by the following means. Aliquots of the above reaction are analyzed by thin layer chromatography (TLC) on activated ammonium sulfate impregnated silica gel TLC plates with a solvent system containing acetone-toluene-water (91:30:8, vol/vol/vol). Products of the above reaction are then visualized with iodine vapor and identified by co-chromatography with an R. sphaeroides lipid extract known to contain DGTS.

IV. Variants of the Peptides Encoded by the R. sphaeroides btaA and btaB Genes

The present invention also contemplates variants of the peptides defined by an amino acid sequence selected from the group consisting of SEQ ID NO: 3 and SEQ ID NO: 4.

It is believed that the R. sphaeroides btaA (SEQ ID NO: 3) and btaB (SEQ ID NO: 4) genes can be "altered" at one or more selected codons to produce variants of the peptides encoded by said genes without significantly disrupting the wild-type functions of the peptides. An alteration is defined as a substitution, deletion, or insertion of one or more codons in the gene encoding the peptide of interest that results in a change in the amino acid sequence of the peptide as compared with the unaltered or wild-type sequence of the peptide. Preferably, the alterations are by conservative substitution of at least one amino acid with another amino acid in one or more regions of the molecule.

For example, it is contemplated that an isolated replacement of a leucine with an isoleucine or valine, an alanine with a glycine, a threonine with a serine, or a similar replacement of an amino acid with a structurally related amino acid (i.e., conservative mutations) will not have a major effect on the biological activity of the resulting molecule. Conservative substitutions are those that take place within a family of amino acids that are related in their side chains. Amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In an alternative, yet similar fashion, the amino acid repertoire can be grouped as: (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer ed., *Biochemistry*, 2nd ed, WH Freeman and Co. (1981)).

Thus, in certain embodiments, modifications of the peptides encoded by an amino acid sequence selected from the group consisting of SEQ ID NO: 3 and SEQ ID NO: 4 are contemplated by the present invention. Guidance in determining which and how many amino acid residues may be substituted, inserted or deleted without abolishing biological or immunological activity may be found using computer programs well known in the art, for example, DNAStar software or GCG (Univ. of Wisconsin).

Whether a change in the amino acid sequence of a peptide defined by an amino acid sequence selected from the group consisting of SEQ ID NO: 3 and SEQ ID NO: 4 results in a peptide useful for the production of betaine lipids can be readily determined by monitoring the level of production of said lipids by TLC as described above (i.e. if the function of either the R. sphaeroides btaA or btaB peptide is significantly disrupted by the amino acid substitution, then the production of betaine lipids (e.g. DGTS) is reduced or completely abolished, and the TLC assay should reflect the difference in betaine lipid production when compared to such lipids produced by the wild-type R. sphaeroides peptides).

Oligonucleotide-mediated, or site-directed, mutagenesis is the preferred method for preparing substitution, deletion, or insertion variants of the peptides defined by the amino acid sequence of SEQ ID NO: 3 and SEQ ID NO: 4. The technique is well known in the art as described by Zoller et al., *Nucl. Acids Res.*, 10: 6487 (1987). (See also Carter et al., *Nucl. Acids. Res.*, 13: 4331 (1986)).

Generally, oligonucleotides of at least 25 nucleotides in length are used. Although smaller oligonucleotides can be employed, an optimal oligonucleotide has 12 to 15 nucleotides that are complementary to the template on either side of the nucleotide(s) coding for the mutation. This ensures that the oligonucleotide hybridizes properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can only be generated by those vectors that are either derived from bacteriophage M13 vectors (the commercially available M13mp18 and M13mp19 vectors are suitable), or those vectors that contain a single-stranded phage origin of replication as described by Vieira and Messing, *Meth. Enzymol.*, 153: 3–11 (1987). A preferred vector is pBlueScript II SK+ (Stratagene) which contains the filamentous phage f1 origin of replication, thereby allowing the rescue of single-stranded DNA upon co-infection with a helper phage. Thus, the DNA that is to be mutated must be inserted into one of these vectors in order to generate single-stranded template. Production of the single-stranded template is described in sections 4.21–4.41 of Sambrook et al., "Molecular Biology: A Laboratory Manual," Cold Spring Harbor Press, Cold Spring Harbor, N.Y. (1989).

Briefly, in one embodiment, the *R. sphaeroides* wild-type btaA and btaB genes are altered by hybridizing an oligonucleotide encoding the desired mutation to a DNA template under suitable hybridization conditions, wherein the template is the single-stranded form of the plasmid containing the unaltered or wild-type DNA sequence for btaA (SEQ ID NO: 1) or btaB (SEQ ID NO: 2). After hybridization, a DNA polymerizing enzyme (e.g. the Klenow fragment of DNA polymerase I) is then added to synthesize the complementary strand of the template using the oligonucleotide as a primer for synthesis, and thus incorporates the oligonucleotide primer and codes for the selected alteration in the btaA and btaB genes. A heteroduplex molecule is thus formed such that one strand of DNA encodes the mutated form of the btaA or btaB gene, and the other strand (the original template) encodes the wild-type, unaltered sequence of the btaA or btaB gene. This heteroduplex molecule is then transformed into a suitable host cell, usually a prokaryote such as *E. coli* JM101. After the cells are grown, they are plated onto agarose plates and screened by colony hybridization using the oligonucleotide primer radio-labeled with $^{32}$-Phosphate to identify the bacterial colonies that contain the mutated DNA. (See Short et al., *Nucleic Acids Res.*, 16: 7583–7599 (1988)).

The method described immediately above can be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(AS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA contains dCTP-(AS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

It is not intended that the present invention be limited to variants of the peptides defined by an amino acid sequence selected from the group consisting of SEQ ID NO: 3 and SEQ ID NO: 4 wherein only a single amino acid substitution has been made. The present invention also contemplates variants that comprise greater than one amino acid substitution. Variants with more than one amino acid to be substituted can be generated in one of several ways. In one embodiment, if the amino acids are located close together in the polypeptide chain, they can be mutated simultaneously using one oligonucleotide that codes for all of the desired amino acid substitutions. However, if the amino acids are located some distance from each other (separated by more than about ten amino acids), it is more difficult to generate a single oligonucleotide that encodes all of the desired changes. Instead, one of two alternative methods can be employed.

In another embodiment, a separate oligonucleotide is generated for each amino acid to be substituted. The oligonucleotides are then annealed to the single-stranded template DNA simultaneously, and the second strand of DNA that is synthesized form the template encodes all of the desired amino acid substitutions. An alternative embodiment involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Transformation of prokaryotic cells is readily accomplished using the calcium chloride method as described in section 1.82 of Sambrook et al., supra. Alternatively, electroporation (Neumann et al., *EMBO J.*, 1: 841 (1982)) can be used to transform these cells. The transformed cells are selected by growth on an antibiotic, commonly tetracycline, kanamycin, or ampicillin, to which they are rendered resistant due to the presence of tet, kan, and/or amp resistance genes on the vector.

Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue MRF' (Stratagene), and *E. coli* B; however, many other strains of *E. coli*, such as HB101, NM522, NM538, and NM539, and many other species and genera of prokaryotes can be used as well. In addition to the *E. coli* strains listed above, bacilli such as *Bacillus subtilis*, other enterobacteriaceae such as *Salmonella typhimuurium* or *Serratia marcescens*, and various *Pseudomonas* species can all be used as hosts.

After selection of the transformed cells, these cells are grown in culture and the plasmid DNA (or other vector with the foreign gene inserted) is then isolated. Plasmid DNA can be isolated using methods known in the art. Two suitable methods are the small-scale preparation of DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing to confirm the presence of the desired btaA or btaB mutation in the selected transformant. DNA sequencing is generally performed by either the method of Messing et al., "A system for shotgun DNA sequencing," *Nucleic Acids Res.,* 9: 309 (1981), the method of Maxam A. M. & Gilbert W., "Sequencing end-labelled DNA with base-specific chemical cleavages," *Meth. Enzymol.,* 65: 499–560 (1980), or the method of Sanger et al., "DNA sequencing with chain-terminating inhibitors," *Proc. Natl. Acad. Sci. USA,* 74: 5463–5467 (1977).

V. *R. sphaeroides* btaA and btaB Gene Homologs

It is not intended that the present invention be limited to the utilization of peptides encoded by the oligonucleotide sequence of the btaA (SEQ ID NO: 1) and btaB (SEQ ID NO: 2) genes from *R. sphaeroides*. The present invention also relates to methods for discovering homologs of the *R. sphaeroides* btaA and btaB genes in other organisms, and compositions comprised thereof. In one embodiment, the present invention contemplates utilizing compositions comprising peptides encoded by an oligonucleotide sequence selected from the group consisting of SEQ ID NO: 22 and SEQ ID NO: 23. In one embodiment, a method for the isolation and purification of the *R. sphaeroides* btaA and btaB gene homologs from *Mesorhizobium loti*, Ml-btaA (SEQ ID NO: 22)(FIG. 22) and Ml-btaB (SEQ ID NO: 23)(FIG. 23), is conducted as follows.

In order to identify *R. sphaeroides* btaA and btaB gene homologs in *M. loti*, the GenBank database of nucleic and amino acid sequences for *M. loti* (GenBank Accession Nos. AP002997, BA000012) is searched with the oligonucleotide and amino acid sequences of the *R. sphaeroides* btaA and btaB genes using TBLASTN. Two such homologs were identified in the organism *Mesorhizobium loti* (i.e. Ml-btaA and Ml-btaB), and an amino acid consensus alignment was perfomed. (See FIGS. 20 and 21). The identified homologs are then cloned into pPCR-Script Amp for expression in *E. coli* using a PCR-based strategy.

Briefly, genomic DNA from *M. loti* is isolated as described above for the isolation of *R. sphaeroides* genomic DNA. *M. loti* genomic DNA is then subjected to PCR in order to clone the Ml-btaA and Ml-btaB genes into *E. coli*. For example, for the Ml-btaA gene, a forward primer having the oligonucleotide sequence 5'-ACA TGC ATG CAA TGA CGG ACG TCT CCT CGG A-3' (SEQ ID NO: 24), and a reverse primer having the oligonucleotide sequence 5'-CGG GGT ACC TCA TGC CGT GCG CTT CAC AT-3' (SEQ ID NO: 25), are used such that Sph I and Kpn I sites, respectively, were generated. For the Ml-btaB gene, a forward primer having the oligonucleotide sequence 5'-GCG GAT CCG ATG ACC GAG CTG CCG G-3' (SEQ ID NO: 26), and a reverse primer having the oligonucleotide sequence 5'-GCA AGC TTT TAG CTG GCG ATC TTG ATC A-3' (SEQ ID NO: 27), are used such that Bam HI and HinD III sites, respectively, were generated.

Specifically, the Ml-btaA and Ml-btaB genes are generated by PCR in reaction mixtures (50 μl) comprising: 1×PCR buffer (Gibco-BRL); 2.5 mM $MgCl_2$ (Gibco-BRL); 350 nM forward primer; 350 nM reverse primer; 10% (v/v) DMSO; 200 μM dATP, dGTP, dCTP, dTTP; 1 ng *M. loti* genomic DNA; and 2.5 U Taq DNA polymerase (Roche Molecular). PCR reaction mixtures are subjected to thermal cycling in a GeneAmp PCR System 9600 thermal cycler (Applied Biosystems, Foster City, Calif.: Cat. No. N801-0001) under the following conditions: 1 denaturation cycle at 95° C. for 3 minutes; 30 cycles comprised of 95° C. for 30 seconds, 57° C. for 30 seconds, and 72° C. for 60 seconds; and 1 extension cycle at 72° C. for 5 minutes. PCR products are run on 1% TAE agarose gel in the presence of ethidium bromide, and excised for purification by QIAEX II gel extraction kit (Qiagen Cat. No. 20021), followed by cloning into the Srf I site of pPCR-Script Amp (as per manufacturer's instructions). The resulting plasmid constructs allow the independent expression of the recombinant *R. sphaeroides* btaA and btaB genes in *E. coli.*

Next, in order to isolate and purify the Ml-btaA and Ml-btaB gene products, the Ml-btaA and Ml-btaB genes are cloned into the protein expression vectors pQE-31 and pACYC-31. Briefly, for the Ml-btaA gene, pQE-31 and pACYC-31 vectors are digested with Sph I and Kpn I and gel purified using the QIAEX II kit. The PCR insert is excised from pPCR-Script Amp by Sph I/Kpn I digest and gel purified, followed by ligation of the insert and vectors. Ligation reactions are then transformed into electrocompetent XL1-Blue *E. coli* and plated onto LB Ampicillin plates (pQE-31) or LB Chloramphenicol plates (pACYC-31). For the Ml-btaB gene, pQE-31 and pACYC-31 are digested with Bam HI and HinD III and gel purified as described above. The insert is released from the vector by Bam HI/HinD III digest and gel purified, followed by ligation of insert and vectors. Ligation reactions are then transformed into electrocompetent XL1-Blue *E. coli* and plated onto LB Ampicillin plates (pQE-31) or LB Chloramphenicol plates (pACYC-31).

Each construct is analyzed individually for protein expression as detailed in the QIAexpress literature using M15[pREP4] as an expression host for the pQE-31 based plasmids and XL1-Blue as the host for pACYC-31 based constructs. Since the pACYC-31 and pQE-31 vectors carry compatible origins of replication, reconstitution of the DGTS biosynthetic pathway is achieved by the concurrent expression of pACYC-31:Ml-btaA and pQE-31:Ml-btaB, or pACYC-31:Ml-btaB and pQE-31:Ml-btaA, in XL1-Blue cells. Cells expressing both of said genes are analysed by TLC for DGTS production after induction with IPTG as described above.

EXPERIMENTAL

Example 1

In this example, a means for the amplification of the *R. sphaeroides* btaA and btaB genes, and their subsequent cloning into *E. coli*, is described. In one embodiment, the btaA gene was amplified from *R. sphaeroides* genomic DNA by PCR using a forward primer having the nucleotide sequence 5'-ACA TGC ATG CAG TGA CGC AGT TCG CCC TC-3' (SEQ ID NO: 5), and a reverse primer having the nucleotide sequence 5'-CGG GGT ACC AGG ACG ATC CGC TCG AAC CG-3' (SEQ ID NO: 6). The primers were used such that BamH1 and HindIII sites were provided for cloning into pPCR-Script Amp (Stratagene Cat. No. 211188).

In another embodiment, the btaB gene was amplified using a forward primer having the nucleotide sequence 5'-ACA TGC ATG CAG TGA CGC AGT TCG CCC TC-3' (SEQ ID NO: 7), and a reverse primer having the nucleotide sequence 5'-CGG GGT ACC AGG ACG ATC CGC TCG AAC CG-3' (SEQ ID NO: 8). The primers were used such that Sph I and Kpn I sites were provided for cloning into pPCR-Script Amp.

All 50 µl PCR reaction mixtures contained the following: 1×PCR buffer (Gibco-BRL Cat. No. 18067-017), 2.5 mM MgCl$_2$, 350 nM forward primer, 350 nM reverse primer, 10% (v/v) dimethylsulfoxide (DMSO), 200 µM dATP, dGTP, dCTP, dTTP, 1 ng R. sphaeroides genomic DNA (isolated and purified as described above), and 2.5 U Taq DNA polymerase (Roche Molecular Cat. No. 1146173). PCR reaction mixtures were subjected to thermal cycling in a GeneAmp PCR System 9600 thermal cycler (Applied Biosystems, Foster City, Calif.: Cat. No. N801-0001) under the following conditions: 1 denaturation cycle at 95° C. for 3 minutes; 30 cycles comprised of 95° C. for 30 seconds, 57° C. for 30 seconds, and 72° C. for 60 seconds; and 1 extension cycle at 72° C. for 5 minutes. PCR products were run on a 1% TAE agarose gel in the presence of ethidium bromide, and excised for purification by QIAEX II gel extraction kit (Qiagen Cat. No. 20021), followed by cloning into the SrfI site of pPCR-Script Amp (as per manufacturer's instructions). The resulting plasmid constructs allow the independent expression of the recombinant R. sphaeroides btaA and btaB genes in E. coli.

Example 2

In this example, a method for the reconstitution of the betaine lipid biosynthetic pathway in plants is performed. The compositions and methods described herein provide for the expression of the R. sphaeroides btaA and btaB genes targeted to the cytosol, or targeted to the plastid. Moreover, the compositions and methods described herein also provide for the selective expression of said genes only in seeds produced by the transformed plant, or alternatively, the constitutive expression of said genes in a transformed plant. All PCR reaction mixtures, thermal cycling program parameters, and component sources are as described above in Example 1.

a. Binary vectors for the constitutive expression of the R. sphaeroides btaA and btaB genes in the plant cytosol are prepared using a PCR-based strategy as follows. For this purpose, the btaA gene sequence was amplified by PCR using a forward primer having the nucleotide sequence 5'-GCT CTA GAA TGG CGC AGT TCG CCC TC-3' (SEQ ID NO: 11), and a reverse primer having the nucleotide sequence 5'-ACA TGC ATG CAG GAC GAT CCG CTC GAA CCG-3' (SEQ ID NO: 12). The btaB gene sequence was amplified by PCR using a forward primer having the nucleotide sequence 5'-GCT CTA GAA TGG CCG ACG CCA CCC AT-3' (SEQ ID NO: 13), and a reverse primer having the nucleotide sequence 5'-ACA TGC ATG CAG GAC GAT CCG CTC GAA CCG-3' (SEQ ID NO: 14). The primers were constructed such that Sph I and Xba I sites are provided for subsequent cloning of the btaA and btaB gene PCR products into the corresponding restriction sites on the binary vector, pBinAR-Hyg. This vector is derived from pBIB-Hyg (Becker, D., *Nucleic Acids Res.* 18: 203 (1990)) by insertion of the Hind III-Eco RI fragment from the central portion of pA7 (von Schaeven, A., Ph.D. thesis, Freie Universität Berlin (1989)). This construct is introduced into *Agrobacterium tumefaciens* strain C58C1 and used to transform *Arabidopsis thaliana* Col-2 plants as described below.

b. Binary vectors for the constitutive expression of the R. sphaeroides btaA and btaB genes targeted to the plastid are prepared using a two-stage Splicing by Overlap (SOE)-PCR-based strategy as follows. In the first stage, the btaA gene sequence was amplified by SOE-PCR using a forward primer having the nucleotide sequence 5'-ATG CAG GTG TGG CCT CCA GTG ACG CAG TTC GCC CTC-3' (SEQ ID NO: 15), and a rbcS-specific reverse primer having the nucleotide sequence 5'-GAG GGC GAA CTG CGT CAC TGG AGG CCA CAC CTG CAT-3' (SEQ ID NO: 16). The btaB gene sequence was amplified by SOE-PCR using a forward primer having the nucleotide sequence 5'-ATG CAG GTG TGG CCT CCA ATG ACC GAC GCC ACC CAT-3' (SEQ ID NO: 17), and rbcS-specific reverse primer having the nucleotide sequence 5'-ATG GGT GGC GTC GGT CAT TGG AGG CCA CAC CTG CAT-3' (SEQ ID NO: 18). The rbcS-specific primers are used to fuse the rbcS transit peptide from the Pea ribulose-1,5-bisphosphate carboxylase small subunit (rbcS) (GenBank Accession No. X04333), as described by Fluhr et al., "Expression and dynamics of the pea rbcS multigene family and organ distribution of the transcripts," *EMBO J.*, 5: 2063–2071 (1986), to the btaA and btaB gene sequences individually. After amplification, the rbcS, btaA, and btaB PCR products are gel purified using QIAEX II (QIAGEN).

In the second stage, the purified rbcS, btaA, and btaB PCR products are then subjected to a second round of PCR. For the btaA gene, a rbcS-specific forward primer having the nucleotide sequence 5'-GCT CTA GAA ACC ACA AGA ACT AAG AA-3' (SEQ ID NO: 19), and a reverse primer having the nucleotide sequence 5'-ACA TGC ATG CAG GAC GAT CCG CTC GAA CCG-3' (SEQ ID NO: 20), are used. For the btaB gene, a reverse primer having the nucleotide sequence 5'-ACA TGC ATG CCT CTC ACC GCG TGA GCG TG-3' (SEQ ID NO: 21), and the same rbcS-specific forward primer (SEQ ID NO: 19), are used.

The second-stage PCR primers were constructed such that Sph I and Xba I sites are provided for subsequent cloning of the rbcS transit peptide-fused btaA and btaB gene PCR products into the corresponding restriction sites on the binary vector, pBinAR-Hyg. However, prior to cloning into pBinAR-Hyg, said PCR products are cloned into pPCR-Script Amp and cut with Sph I and Xba I. The plasmids containing the desired PCR products are transformed into *E. coli* and grown in LB medium with 50 mg/ml ampicillin. The plasmid DNA is isolated and digested with Sph I and Xba I, followed by gel purification of the desired plasmid inserts as described above. Finally, the inserts are sub-cloned into the corresponding sites of pBinAR-Hyg. The resulting plasmid constructs are introduced into *Agrobacterium tumefaciens* strain C58C1 and used to transform *Arabidopsis thaliana* Col-2 plants as described below.

c. Binary vectors for the seed-specific expression of the R. sphaeroides btaA and btaB genes in the plant cytosol and plastid are prepared using a PCR-based strategy as described above with the following substitutions. In order to obtain seed-specific expression of the R. sphaeroides btaA and btaB genes in plants, the binary vector pBinUSP-Hyg is used in place of the pBinAR-Hyg vector described above. The pBinUSP-Hyg vector contains the USP promoter derived from the broad bean plant as described by Fiedler et al., "A complex ensemble of cis-regulatory elements controls the expression of a *Vicia faba* non-storage seed protein gene," *Plant Mol. Biol.*, 22: 669–679 (1993). The use of the USP promoter to obtain seed-specific expression of proteins has been demonstrated in *A. thaliana*. Bäumlein et al., "A novel seed protein gene from *Vica faba* is developmentally regulated in transgenic tobacco and *Arabidopsis* plants," *Mol. Gen. Genet.*, 225: 459–467 (1991). The resulting plasmid constructs are introduced into *Agrobacterium tumefaciens* strain C58C1 and used to transform *Arabidopsis thaliana* Col-2 plants as described below.

d. A means for the simplified transformation of *Arabidopsis* is described herein and follows the methods of S. Clough and A. Bent, "Floral dip: a simplified method for *Agrobacterium*-mediated transformation of *Arabidopsis thaliana*," *Plant J.*, 16:735–43 (1998). *Arabidopsis* plants are grown under long days in pots in soil covered with bridal veil, window screen or cheesecloth, until they are flowering. First bolts are clipped to encourage proliferation of many secondary bolts, causing the plants to be ready roughly 4–6 days after clipping. Optimal plants have many immature flower clusters and not many fertilized siliques, although a range of plant stages can be successfully transformed.

The *Agrobacterium tumefaciens* strain carrying the gene of interest on a binary vector is grown in a large liquid culture at 28° C. in LB (10 g tryptone, 5 g yeast extract, and 5 g NaCl per liter of water) with 25 μg/ml hygromycin B (Calbiochem) to select for the binary plasmid. The *Agrobacterium* culture is pelleted by centrifugation at 5500×g for 20 minutes, and resuspended to $OD_{600}=0.8$ in a sterile 5% Sucrose solution.

Before the above-ground parts of an *Arabidopsis* plant are dipped in the resuspended *Agrobacterium*/Sucrose solution, Silwet L-77 (OSi Specialties, Inc., Danbury, Conn.) is added to a concentration of 0.05% (500 μl/L) and mixed well. The above-ground parts of an *Arabidopsis* plant are dipped in the *Agrobacterium* solution for 2 to 3 seconds, with gentle agitation. The dipped plants are placed under a dome or cover for 16 to 24 hours to maintain high humidity. The dipped plants are not exposed to excessive sunlight as the air under the dome can get hot.

The plants are grown for a further 3–5 weeks and watered normally, tying up loose bolts with wax paper, tape, stakes, twist-ties, or other means. Watering is halted as the seeds of the plant become mature. Once mature, the dry seeds are harvested by the gentle pulling of grouped inflorescences (i.e. flower clusters) through fingers over a clean piece of paper. The majority of the stem and pod material is removed from the paper and the seeds are stored under dessication at 4° C.

Successful transformants capable of expressing a recombinant *A. thaliana* peptide are selected by using an antibiotic or herbicide selectable marker. In this example, 2000 harvested seeds (resuspended in 4 ml 0.1% agarose) are vapor-phase sterilized and plated on selection plates with 50 μg/ml hygromycin B, cold treated for 2 days, and then grown under continuous light (50–100 μEinsteins) for 7–10 days. The selection plates of the example further comprise 0.5× Murashige-Skoog medium (Sigma Chem. Cat. No. M-5519) and 0.8% tissue culture Agar (Sigma Chem. Cat. No. A-1296). Successful transformants are identified as hygromycin-resistant seedlings that produce green leaves and well-established roots, within the selective medium.

A sample of successful transformants are grown to maturity by transplantation into heavily moistened potting soil. Leaves from the transformants are removed and subjected to DNA extraction to isolate the genomic DNA of the plant. The extracted genomic DNA is subsequently subjected to restriction endonuclease digestion and Southern Blotting to confirm the incorporation of the gene of interest into the plant's genome.

e. A method for the crossing of a transformed plant containing the *R. sphaeroides* btaA gene with a transformed plant containing the *R. sphaeroides* btaB gene, such that the betaine lipid biosynthetic pathway is reconstituted in a single plant, is provided as follows.

A transformed female parent plant (4–6 weeks-old) containing the *R. sphaeroides* btaA is used as a pistil donor. Several young flower buds that are located at the top of the inflorescence on the main flowering stalk are chosen. The newly emerging white petals should be barely visible in the most mature flower bud chosen. The use of any flower bud that has opened and potentially exposed its pistil to parental pollen or another pollen source is avoided. For example, a bud at the correct stage will contain short immature stamens with anthers that are greenish-yellow in color. All other flower buds and flowers from the inflorescence are removed.

Prior to dissection of the chosen flower buds, forceps are sterilized in 95% ethanol and air-dried to remove contaminating pollen. Next, the sepals, petals, and stamens are removed from the flower buds beginning with the tissue near the base of the flower bud. Great care should be taken not to injure the pistil or flower stalk while dissecting the flower bud. When finished, the pistil is free of sepals, petals, and stamens.

A transformed male parent plant (4–6 weeks-old) containing *R. sphaeroides* btaB is used as a pollen donor. First, a suitable pollen-donor flower is selected. For example, for wild-type *Arabidopsis*, a flower that has opened and has petals that are perpendicular to the main flower body is chosen. To confirm that the chosen flowers are in the process of releasing pollen, visual examination of the anthers from several flowers to identify the flowering stage associated with pollen release is performed. Next, the flower is removed from the flowering stalk, followed by removal of the petals and sepals from the flower. This process yields 6 stamens (2 short and 4 tall) for each flower. Several stamens are removed and their anthers checked for pollen. The pollen grains should be clearly visible when viewed under a dissecting microscope. When anthers brimming with pollen are identified, they are used to pollinate the stigmas of the previously prepared pistils. To maximize the probability of pollination, each pistil is pollinated with several anthers.

When pollination is complete, the pistil is covered with a small piece of plastic wrap (1 cm×1 cm) to protect it from other pollen sources. The plastic wrap is folded in half around the pistil. Next, the pollinated pistil is marked by applying a small piece of tape describing the cross on the corresponding flowering stalk. The plastic wrap is removed in 1 to 2 days. Following a successful pollination, the pistil elongates as the seeds develop. When the silique is fully elongated and has dried to a golden-brown color, it is removed from the plant, taking care not shatter the silique and lose the seeds. The seeds are allowed to dry for at least one week before planting. The seeds can also be chilled at 4° C. for several days following imbibition to increase the frequency of germination. Germinated seeds are planted to produce plants which comprise both the *R. sphaeroides* btaA and btaB genes, thereby reconstituting the betaine lipid biosynthetic pathway in a single plant. Lipid extracts may be made from transformed plant leaves and seeds, and subjected to quantitative lipid analysis by TLC (as described above) to confirm the production of betaine lipids including, but not limited to, DGTS.

Example 3

In this example, one method of generating variants of the peptides defined by an amino acid sequence selected from the group consisting of SEQ ID NO: 3 and SEQ ID NO: 4, by conservative amino acid substitution is provided. Briefly, this method comprises the cloning of the *R. sphaeroides* btaA and btaB genes into the phagemid vector pBluescript II SK+, growth and recovery of single stranded DNA templates for each of said genes, oligonucleotide-directed mutagenesis, transformation of suitable host cells for production of double-stranded DNAs containing the directed mutation, and confirmation of the transformants as having incorporated the desired mutation. This method is performed as described in the manufacturer's instruction manual for the "pBlueScript II Exo/Mung DNA Sequencing System." (Stratagene Cat. No. 212301).

a. Cloning of btaA and btaB into pBluescript II SK+

The independent cloning of the *R. sphaeroides* btaA and btaB genes into the phagemid vector pBluescript II SK+ is accomplished as described above in Part I.A.

b. Recovery of Single-Stranded DNA Template from Cells Containing pBlueScript II SK+ Phagemids pBluescript II SK+ is a phagemid which can be secreted as single-stranded DNA in the presence of M13 helper phage. These phagemids contain the intergenic (IG) region of a filamentous f1 phage. This region encodes all of the cis-acting functions of the phage required for packaging and replication. In *E. coli* with the F+phenotype (containing an F' episome), pBluescript II SK+ phagemids will be secreted as single-stranded f1 "packaged" phage when the bacteria has been infected by a helper phage. Since these filamentous helper phages (VCSM13, f1) will not infect *E. coli* without an F' episome coding for pili, it is essential to use XL1-Blue MRF' (Stratagene Cat. No. 212301) or a similar strain containing the F' episome.

Typically, 30–50 pBluescript II SK+ molecules are packaged/helper phage DNA molecule. pBluescript II SK phagemids are offered with the IG region in either of two orientations: pBluescript II SK (+) is replicated so the coding strand of the β-galactosidase gene (the top strand in the enclosed map, the same strand as in the mp vectors) is secreted within the phage particles; pBluescript II SK (−) is replicated so the non-coding strand of the β-galactosidase gene is secreted in the phage particles.

Yields of single-stranded (ss)DNA depend on the specific insert sequence. For most inserts, over 1 μg of ssDNA can be obtained from a 1.5-ml miniprep if grown in XL1-Blue MRF'. A faint single-strand helper phage band may appear on a gel at ~4 kb for R408 or 6 kb for VCSM13. This DNA mixture can be sequenced with primers that are specific for pBluescript II SK+ (e.g. the SK primer and M13(−20) primer (Stratagene Cat. Nos. 300305 & 300303, respectively)) and do not hybridize to the helper phage genome.

VCSM13 and R408 helper phage produce the largest amount of single-strand pBluescript II SK+. R408 (single-strand size ~4 kb) is more stable and can be grown more easily. VCSM13 (single-strand size ~6 kb), being more efficient, yields more single-stranded phagemid; however it is more unstable and reverts to wild-type more frequently. This difficulty can be addressed by periodically propagating VCSM13 in the presence of kanamycin. VCSM13 (a derivative of M13KO7) has a kanamycin gene inserted into the intergenic region (IG), while R408 has a deletion in that region.

The advantages of using pBluescript II phagemids for site-specific mutagenesis using standard techniques are as follows: (1) pBluescript II SK phagemids do not replicate via the M13 cycle, lessening the tendency to delete DNA inserts, therefore it is unlikely that even 10-kb inserts will be deleted; (2) "packaging" of pBluescript II SK phagemids containing inserts is efficient since the pBluescript II SK vector is 3.5 kb (smaller than wild-type M13); and (3) oligonucleotide mutagenesis in pBluescript II SK vectors is advantageous because the mutagenized insert is located between the T3 and T7 promoters. The resultant mutant transcripts can be synthesized in vitro without further subcloning.

c. Single-Stranded Template DNA Rescue Protocol

In one embodiment, single-stranded DNA template for oligonucleotide-mediated mutagenesis is prepared from pBlueScript II SK+ phagemids comprising an oligonucleotide sequence selected from the group consisting of SEQ ID NO: 1 and SEQ ID NO: 2, as follows.

A single colony containing pBlueScript II SK+ comprising an oligonucleotide sequence selected from the group consisting of SEQ ID NO: 1 and SEQ ID NO: 2, is inoculated into 5 ml of 2×YT containing 50 μg/ml ampicillin and VCM13 or R408 helper phage at $10^7$–$10^8$ pfu/ml (multiplicity of infection ~10). The culture is grown at 37° C. with vigorous aeration for 1–2 hours. If VCSM13 is used as the helper phage, kanamycin is added to the media at a concentration of 70 μg/ml to select for infected cells. The cells are allowed to continue to grow at 37° C. for 16–24 hours, or until growth has reached saturation. The cells are transferred to 1.5 ml microcentrifuge tubes and centrifuged for 5 minutes. Approximately 1 ml of supernatant is removed, 150 μl of a 20% PEG (polyethylene glycol)/2.5 M NaCl solution is added, and the phage particles are allowed to precipitate on ice for 15 minutes. The phage particles are centrifuged for 5 minutes in a microcentrifuge, followed by the removal of the supernatant. The PEG/phage pellets are centrifuged for a few seconds more to collect residual liquid, which is subsequently removed. The pellets are resuspended in 400 μl of 0.3 M NaOAc (pH 6.0) and 1 mM EDTA by vortexing vigorously.

The resuspended pellets are extracted with 1 volume phenol:chloroform and centrifuged for 1–2 minutes to separate the aqueous and organic phases. The aqueous phase is transferred to a fresh tube, 1 ml of 100% ethanol is added, and the tube is centrifuged for 5 minutes. The ethanol is removed, the DNA pellet is air-dried and dissolved in 25 μl of TE buffer. For analysis, 1–2 μl of the dissolved ssDNA template may be run on an agarose gel.

d. Oligonucleotide-Mediated/Site-Directed Mutagenesis

Single-stranded DNA templates from cells containing pBluescript II SK+ Phagemids are isolated (as described above) and used for oligonucleotide-mediated mutagenesis according to the following protocol as described in the instruction manual for the "pBluescript II Exo/Mung DNA Sequencing System" (Stratagene Cat. No. 212301). Briefly, oligonucleotides having a oligonucleotide sequence selected from the group consisting of SEQ ID NO: 5, SEQ ID NO: 6, SEQ ID NO: 7, SEQ ID NO: 8, SEQ ID NO: 9, and SEQ ID NO: 10 are hybridized to their corresponding ssDNA templates in order to induce mutagenesis as follows. Said oligonucleotides are designed to generate the following corresponding mutations in either the *R. sphaeroides* btaA or btaB gene sequence as indicated in the table below.

TABLE 3

Details of R. sphaeroides btaA and btaB Mutagenesis

| Mutagenesis Oligonucleotide | Corresponding SEQ ID NO: | R. sphaeroides gene mutated | Amino Acid change generated |
|---|---|---|---|
| btaA-L9I | 5 | btaA | L9I |
| btaA-A201G | 6 | btaA | A201G |
| btaA-S399T | 7 | btaA | S399T |
| btaB-T13S | 8 | btaB | T13S |
| btaB-I115L | 9 | btaB | I115L |
| btaB-G206A | 10 | btaB | G206A |

An oligonucleotide having a oligonucleotide sequence selected from the group consisting of SEQ ID NO: 5, SEQ ID NO: 6, SEQ ID NO: 7, SEQ ID NO: 8, SEQ ID NO: 9, and SEQ ID NO: 10 is kinased in a reaction comprising: 100 ng of mutagenesis oligonucleotide; 4 µl of 10× ligase buffer (500 mM Tris-HCl, pH 7.5; 70 mM $MgCl_2$; and 10 mM dithiothreitol (DTT)); 4 µl of 10 mM rATP; 2 µl of T4 polynucleotide kinase (10 U) (Promega Cat. No. M4101); and water to 40 µl final volume. The reaction is incubated at 37° C. for 30 minutes.

In order to synthesize a btaA or btaB variant DNA strand comprising the desired amino acid substitution (i.e. mutation), the kinased mutagenesis oligonucleotide is annealed to 1 µg of ssDNA template in a reaction comprising 20 µl of oligonucleotide from the kinase reaction above (50 ng) and 5 µl of salmon sperm DNA. The reaction is incubated at 65° C. for 10 minutes, then at room temperature for 5 minutes. Once the mutagenesis oligonucleotide has been annealed to the ssDNA template, the second strand of the DNA template (incorporating the amino acid substitution) is generated by primer extension as follows. To the annealing reaction, the following is added: 4.0 µl of 10× ligase buffer (same as above); 2.0 µl of 2.5 mM dNTPs (N=A, C, G and T in equal concentration); 4.0 µl of 10 mM rATP; 1.0 µg of single-stranded DNA binding protein (Promega Cat. No. M3011); 1.5 U of DNA Polymerase I, Klenow Fragment (Promega Cat. No. M2201); 0.5 µl of T4 DNA ligase (2 U) (Promega Cat. No. M1801), and water to 40 µl final volume. The reaction is incubated at room temperature for 3–4 hours. After incubation is complete, E. coli XL1-Blue MRF' cells are transformed with 10 µl of synthesis reaction and plated on LB medium (10 g NaCl, 10 g tryptone, 5 g yeast extract, deionized water to 1000 ml, and adjusted to pH 7.0) plates containing 50 µg/ml ampicillin, 12.5 µg/ml tetracycline, 80 µg/ml freshly prepared X-Gal (Promega Cat. No. V3941), and 20 mM IPTG to allow antibiotic and blue-white color selection of transformed bacterial colonies containing phagemids comprising the desired amino acid change. Said colonies may be screened for incorporation of the desired amino acid substitution by colony hybridization analysis as described below. If said colonies are to be screened by colony hybridization, then transformed XL1-Blue MRF' cells should be plated onto nitrocellulose filters placed on top of three LB plates lacking IPTG. After 8–10 hours of incubation, the nitrocellulose filters are transferred to LB plates containing 5 mM IPTG for several hours.

e. Screening Transformant Colonies for Confirmation of Amino Acid Substitution

Colonies containing pBluescript II SK+ phagemids may be screened for recombinants by many techniques widely known in the art such as double-stranded DNA, RNA, or oligonucleotide hybridization (e.g. colony hybridization). (See Instruction Manual for the "pBluescript II Exo/Mung DNA Sequencing System" (Stratagene Cat. No. 212301)). Colonies may also be screened by restriction endonuclease mapping or by sequencing plasmid DNA (e.g. Sanger dideoxy chain terminator DNA sequencing, Maxam & Gilbert sequencing) to confirm the presence of an amino acid substitution at the desired amino acid residue.

Example 4

In this example, one method of cloning and expressing Bta1 from Chlamydomonas reinhardtii is provided.

Briefly, the protein sequence of BtaA from Rhodobacter sphaeroides (RsBtaA) was used as a query in a TBLASTN search against a draft of the C. reinhardtii genome found at the Joint Genome Institute website of the Department of Energy. In this way, a protein with strong similarity to RsBtaA was identified. The predicted protein is encoded by a gene on scaffold 250 from about position 17000–23500. The protein predicted by the "green genie" prediction program is 648 amino acids long and contains an N-terminal region with significant identity to the bacterial BtaB protein, and a C-terminal region similar to the bacterial BtaA protein. Thus, it is contemplated that a single C. reinhardtii protein is responsible for all reactions of DGTS synthesis, and thus the newly-identified gene was given the name "Bta1" to reflect this. The genomic DNA sequence of C. reinhardtii Bta1 is set forth herein as SEQ ID NO: 43, while the cDNA sequence is set forth as SEQ ID NO: 44, and the protein sequence (CrBta1) is set forth as SEQ ID NO: 45. Primers were designed to amplify the coding sequence by RT-PCR and to facilitate expression of the protein as an N-terminal His-tag fusion in the pQE-31 expression vector (See, FIG. 1). The forward primer contained a Bam HI site upstream of the start codon 5'-CAG GAT CCA ATG GGG TCG GGT CGT-3' (SEQ ID NO:46); while the reverse primer contained a Kpn I site upstream of the stop codon: 5'-CAG GTA CCG CCG CCA GCT GCT TA-3' (SEQ ID NO:47).

A C. reinhardtii cell-wall deficient mutant, CC-400, was grown to mid log phase in TAP medium, and harvested. A 50 ml culture aliquot was used for RNA isolation by TRIzol reagent (Invitrogen), and 2 µg total RNA was used in a reverse transcriptase reaction (SuperScript II RNAse H⁻ Reverse Transcriptase) according to the manufacturer's instructions. Subsequently, a 2 µl aliquot of the RT reaction was used as a template in a 50 µl PCR reaction with the above primers, using Pfu Turbo polymerase and Pfu Native Plus reaction buffer (Stratagene). Due to the high G+C content of Chlamydomonas DNA, DMSO was added to 10% (v/v). Primers were used at a concentration of 350 nm, and dNTPs were used at a concentration of 250 µM each. Cycling was as follows: 5 min at 95° C., then 35 cycles at 95° C. for 30 sec; 54° C. for 30 sec; and 72° C. for 2 min; with a final extension step at 72° C. for 10 min.

Figure 32:
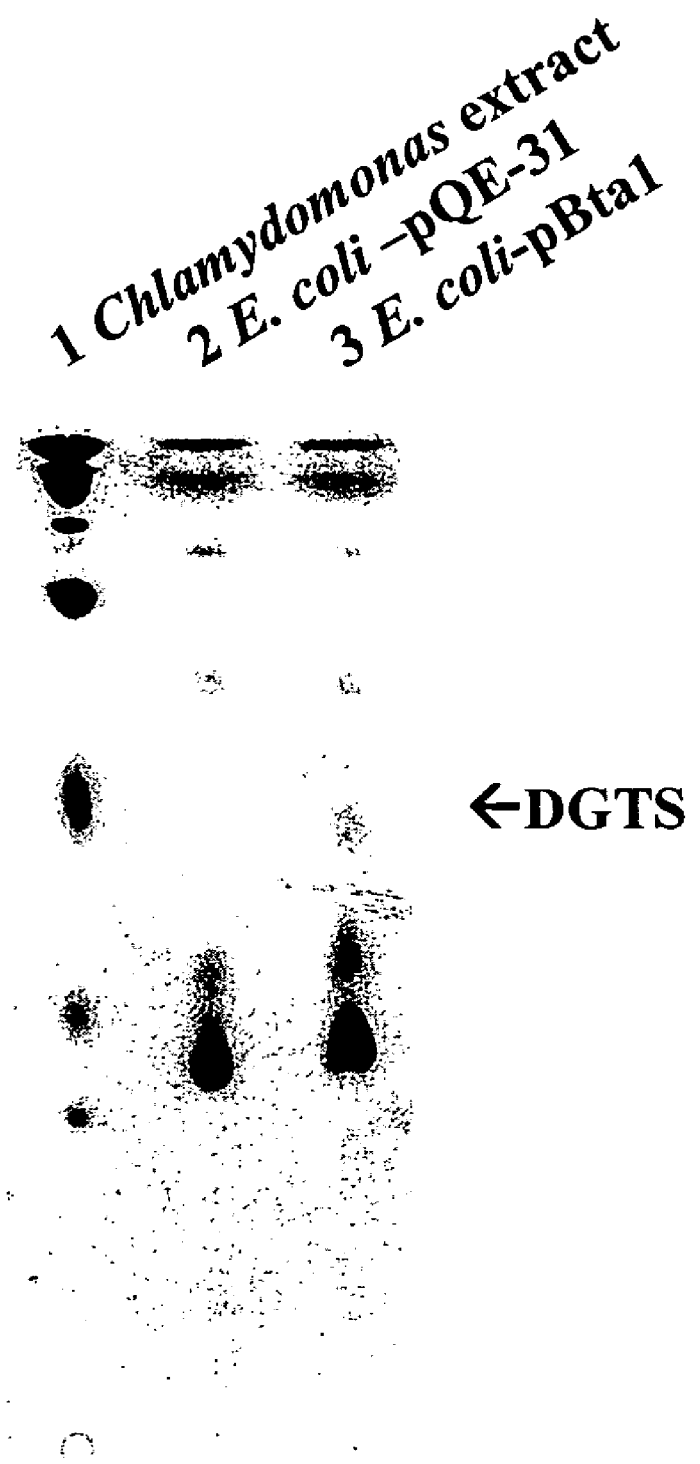
FIG. 32 provides a thin layer chromatogram of lipids extracted from *Chlamydomonas*, and *E. coli* transformed with an empty vector or a Crbta1 expression vector.
Figure 33:
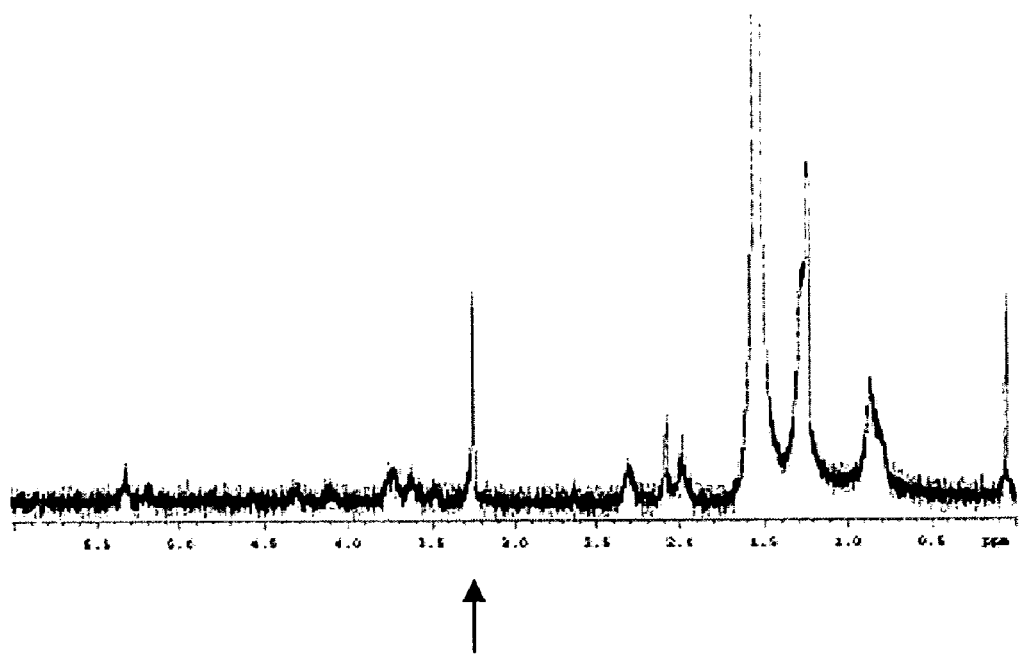
FIG. 33 provides an image of a nuclear magnetic resonance (NMR) analysis of DGTS purified from recombinant *E. coli* expressing Crbta1. The arrow is indicative of the quaternary ammonium function of DGTS.

A product of approximately 1950 bp was produced and cloned into the Eco RV site of pBlueScript II KS+ to facilitate sequencing, then excised by Bam HI and Kpn I digestion in order to directionally clone the fragment into the corresponding sites of pQE-31, giving rise to plasmid pBta1. As shown in FIG. 32, lipid extracts of cells harboring the pBta1 plasmid produced the lipid DGTS to a significant level, estimated at 10–15 mol % based on TLC iodine staining intensity. DGTS was purified from E. coli expressing CrBta1 and analyzed by NMR. As shown in FIG. 33, a strong resonance at ~3.2 ppm was detected, characteristic of the quaternary ammonium function of DGTS, thus confirming the identity of this product. In addition, the inventors contemplate subcloning CrBta1 into pBinAR-Hyg for expression in plants, as described above for *R. sphaerodies* BtaA and BtaB genes in Part II of the Description.

Example 5

In this example, one method of cloning and expressing Bta1 from *Neurospora crassa* is provided.

Briefly, a protein with domains sharing significant sequence similarity with the BtaA and BtaB proteins of bacteria was identified in *Neurospora crassa* genome contig 3.153, by using three sequence analysis programs (combination of FGENESH, FGENESH+, and GENEWISE). The contig is part of the *N. crassa* 3 database found at the web site of the Whitehead Institute's Center for Genome Research. The protein encoded by the minus strand of the *N. crassa* contig (at about position 218593–221450 as set forth in SEQ ID NO: 48) has a N-terminal portion similar to BtaB, and a C-terminal portion similar to BtaA. Thus, the inventors contemplate that the protein functions similarly to the Bta1 protein from *Chlamydomonas reinhardtii*, and hence the gene has been termed *N. crassa* Bta1. The coding region of the gene is provided herein as SEQ ID NO: 49, while the amino acid sequence of the predicted protein (NcBta1) is provided as SEQ ID NO: 50.

Cloning of the open reading frame by RT-PCR is accomplished using the following primer pair: forward, 5'-CAG GTA CCG GAT CCA ATA GCA ATG GGA GAC AAC-3' (SEQ ID NO: 51); and reverse, 5'-CAA AGC TTT CTA GAC TAC TTA AGC TGA GTC AAC C-3' (SEQ ID NO: 52). The Kpn I and Bam HI sites in the forward primer and the HinD III and Xba I sites in the reverse primer were introduced to facilitate cloning into pQE-31 for expression in *E. coli* and pBinAR-Hyg for expression in plants, as described above for *R. sphaerodies* BtaA and BtaB genes in Parts I and II of the Description.

During development of the present invention, the DGTS lipid was found to be produced by *N. crassa* only during low phosphate conditions. Specifically, as shown in FIG. 34, DGTS was produced by *N. crassa* when grown in a modified Vogel's medium containing MES and 0.01 mM Pi, but not when grown in Vogel's medium containing 20 mM Pi. A similar expression pattern was observed for NcBta1 RNA. A complete description of Vogel's medium can be found in Vogel, Microbiol. Genetics Bull., 13:42–43 (1956), herein incorporated by reference.

All publications and patents mentioned in the above specification are herein incorporated by reference. Various modifications and variations of the described method and system of invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A composition comprising a purified DNA having a Bta1 nucleotide sequence of SEQ ID NO: 44.

2. Purified RNA transcribed from the DNA of claim 1.

3. A vector comprising the DNA of claim 1.

4. A host cell comprising the vector of claim 3.

5. The host cell of claim 4, wherein said host cell is *E. coli*.

6. The host cell of claim 4, wherein said host cell is *R. sphaeroides*.

7. The host cell of claim 4, wherein said host cell is *A. thaliana*.

8. Transgenic plants comprising the vector of claim 3.

9. A composition comprising a purified DNA encoding a Bta1 protein having the amino acid sequence of SEQ ID NO: 45.

10. Purified RNA transcribed from the DNA of claim 9.

11. A vector comprising the DNA of claim 9.

12. A host cell comprising the vector of claim 11.

13. The host cell of claim 12, wherein said host cell is *E. coli*.

14. The host cell of claim 12, wherein said host cell is *R. sphaeroides*.

15. The host cell of claim 12, wherein said host cell is *A. thaliana*.

16. Transgenic plants comprising the vector of claim 11.

17. A purified Bta1 nucleic acid that specifically hybridizes to the complement of SEQ ID NO:44 under highly stringent conditions in 5×SSPE, 1% SDS, 5× Denhardt's reagent and 100 µg/ml denatured salmon sperm DNA at 68° C. overnight, followed by a washing in a solution comprising 0.1×SSPE and 0.1% SDS at 68° C., wherein said nucleic acid encodes a protein which synthesizes DGTS.

18. A vector comprising the nucleic acid of claim 17.

19. A host cell comprising the vector of claim 18.

20. A transgenic plant comprising the vector of claim 18.

21. A purified Bta1 nucleic acid comprising a sequence that is at least 95% identical to SEQ ID NO:44, wherein said sequence encodes a protein which synthesizes DGTS.

22. A vector comprising the nucleic acid of claim 21.

23. A host cell comprising the vector of claim 22.

24. A transgenic plant comprising the vector of claim 22.

* * * * *

SEQUENCE LISTING

```
<160> NUMBER OF SEQ ID NOS: 52

<210> SEQ ID NO 1
<211> LENGTH: 1252
<212> TYPE: DNA
<213> ORGANISM: Rhodobacter sphaeroides

<400> SEQUENCE: 1
gtgacgcagt tcgccctcac ccacctgccc gccccgccgg ttgcccgcca gatcggcgcc     60
gccgtgcacc gcacgtcgct tctcagcgcc gaaggactga tggagcggat gttctcgcgc    120
ctcttccacg gcctcgtcta tccgcagatc tgggaggatc cggcggtgga catggcggcc    180
ctcgccatcc gccccgggga ccggctggtg gccatcgcct cgggcggttg caacgtgctt    240
tcctatctca cgcaggggcc gggctcgatc ctcgccgtgg atctctcgcc cgcccatgtg    300
gcgctggggc ggctgaagct cgccgccgcg cggacgctgc ccgaccatgc cgccttcttc    360
gatctcttcg gtcgcgcaga cctgccccggc aatgcggccc tctacgaccg ccacatcgcg    420
cccgcgctcg acggccggag ccgccgctac tgggaggcgc gcagcccctt cggccggcgc    480
atccagctgt tcgagcgcgg cttctaccgg cacggtgccc tcggccgctt catcggcgcg    540
gcccatacgc tcgcgcgggc cgcgggcacc gacctgcggg gctttctcga ctgtcccgac    600
atcgaggcgc agcgcagctt cttctacgcc catatcgggc cgctcttcga ggcgcccgtg    660
gtgcaggcgc tcgcccgacg gccggccgcg ctcttcgggc tggggatccc gcccgcgcaa    720
tatgcgcttc tggcgggaga cggcgacggc gacgtgctgc cggtgctgcg ccagcgcctc    780
caccggctgc tctgtgactt ccccctgcgc gagaactact tcgccttcca ggccatcgcc    840
cgccgctatc cgcggcccgg cgagggcgcg ctgccgccct atctcgaacc caccgccttc    900
```

-continued

```
gagacgctgc gcgagaacgc gggccgggtg cagatcgaga accgcagcct gaccgaggcg    960
ctcgcggccg aacccgagga gagcatccac ggcttcaccc tgctcgatgc gcaggactgg   1020
atgacggacg cgcagctgac cgcgctctgg cggcaggtga cgcgcactgc agcgccgggc   1080
gcgcgggtga tcttccgcac cggcggggcg gccgacctgc tgcccggccg agtgcccgag   1140
gagatcctcg ggcactggcg cgccgaccgg cggcgggac aggcgggcca tgccgccgac   1200
cgttcggcga tctacggcgg cttccacctc taccggcgga gggacgccat ga          1252
```

<210> SEQ ID NO 2
<211> LENGTH: 1255
<212> TYPE: DNA
<213> ORGANISM: Rhodobacter sphaeroides

<400> SEQUENCE: 2

```
atgaccgacg ccacccatgc ggcgctgatg gacgcgacct accgccacca gcgccggatc     60
tacgacgtca cgcggcggca cttcctgctc ggccgcgacc ggctgatcgc cgagctcgac    120 ccgcccccg cgcccgggt gctcgagatc gcctgcggca cggggcgcaa cctcgacctg     180
atcggccggc gctggcccgg ctgccggctc tcggggctcg acatctcgca ggagatgctg    240
gcctcggccc gcgcgcgtct gggccggcgc gcgacgctgg cgctcggcga tgccaccccgg   300 ttcgaggccc tgcccctctt cggcaccgac cggttcgagc ggatcgtcct ctcctacgcg    360
ctctcgatga tccccgactg gcgcgaggcc ctgcgtgagg cggcgcttca tctcgtgccg    420 gggggggcggc tgcatgtcgt cgacttcggc gatcaggcgg gcctgcccgg ctgggcccgc   480
gccggcctgc gcggctggat cgggcgcttc cacgtcacgc gcgcgacga tctgggcacg    540 gcactgggcg aaacggcgct cgggatcggg ggctatgccg aataccggtc cctcggcggg   600
ggatatgcga ttctcggcac gctcacgcgg tgagagatcc cctgccctgc gcgtgacgct   660
tgtctgcccg caggcgaccg gccgcgcgac ggccggcctg cgggcgatcc ggcgcactga   720
aggcccggcg cgtcgcgcgc ggggacgtag cccgcagcgg caagcggccg acagagcctg    780
acagaccgtt cacggtgcgc gctccggatc gggtgtggag ccggtgttgc agaggtcagg    840
cctcgaggga aagccctctg gcccgacggg caaattgtcc gggatctcta atcgggaaat    900
tggtcggagc gagaggattc gaacctccga ccccctgctc ccgaagcagg tgcgctacca    960
ggctgcgcta cgctccgacc ttggcgtgcg gattataggg tcgcgcatcc gaatgcaagg   1020
gggtccgaac gcaattcgct acggagtgtc tcgcgtctcg cggcggcgca gaaggcgcgg   1080
catgaggccc acctcgggcc gcaggcgcgt ctggctcgcc gggcggttct ccgacacgtt   1140
gcggcgcgat tcgcggccga cgatatagag gccgctcgcg atgatgaccc ccgcccccgac  1200 ccaggtccag acgtcggacc gctcgccgaa gatgagccag ccgaagatcc ctgac        1255
```

<210> SEQ ID NO 3
<211> LENGTH: 416
<212> TYPE: PRT
<213> ORGANISM: Rhodobacter sphaeroides

<400> SEQUENCE: 3

```
Met Thr Gln Phe Ala Leu Thr His Leu Pro Ala Pro Val Ala Arg
1               5                  10                  15

Gln Ile Gly Ala Ala Val His Arg Thr Ser Leu Leu Ser Ala Glu Gly
                20                  25                  30

Leu Met Glu Arg Met Phe Ser Arg Leu Phe His Gly Leu Val Tyr Pro
        35                  40                  45
```

```
Gln Ile Trp Glu Asp Pro Ala Val Asp Met Ala Ala Leu Ala Ile Arg
 50                  55                  60

Pro Gly Asp Arg Leu Val Ala Ile Ala Ser Gly Gly Cys Asn Val Leu
 65                  70                  75                  80

Ser Tyr Leu Thr Gln Gly Pro Gly Ser Ile Leu Ala Val Asp Leu Ser
                 85                  90                  95

Pro Ala His Val Ala Leu Gly Arg Leu Lys Leu Ala Ala Ala Arg Thr
            100                 105                 110

Leu Pro Asp His Ala Ala Phe Phe Asp Leu Phe Gly Arg Ala Asp Leu
        115                 120                 125

Pro Gly Asn Ala Ala Leu Tyr Asp Arg His Ile Ala Pro Ala Leu Asp
130                 135                 140

Gly Arg Ser Arg Arg Tyr Trp Glu Ala Arg Ser Pro Phe Gly Arg Arg
145                 150                 155                 160

Ile Gln Leu Phe Glu Arg Gly Phe Tyr Arg His Gly Ala Leu Gly Arg
                165                 170                 175

Phe Ile Gly Ala Ala His Thr Leu Ala Arg Ala Ala Gly Thr Asp Leu
            180                 185                 190

Arg Gly Phe Leu Asp Cys Pro Asp Ile Glu Ala Gln Arg Ser Phe Phe
        195                 200                 205

Tyr Ala His Ile Gly Pro Leu Phe Glu Ala Pro Val Val Gln Ala Leu
210                 215                 220

Ala Arg Arg Pro Ala Ala Leu Phe Gly Leu Gly Ile Pro Pro Ala Gln
225                 230                 235                 240

Tyr Ala Leu Leu Ala Gly Asp Gly Asp Gly Asp Val Leu Pro Val Leu
                245                 250                 255

Arg Gln Arg Leu His Arg Leu Leu Cys Asp Phe Pro Leu Arg Glu Asn
            260                 265                 270

Tyr Phe Ala Phe Gln Ala Ile Ala Arg Arg Tyr Pro Arg Pro Gly Glu
        275                 280                 285

Gly Ala Leu Pro Pro Tyr Leu Glu Pro Thr Ala Phe Glu Thr Leu Arg
290                 295                 300

Glu Asn Ala Gly Arg Val Gln Ile Glu Asn Arg Ser Leu Thr Glu Ala
305                 310                 315                 320

Leu Ala Ala Glu Pro Glu Glu Ser Ile His Gly Phe Thr Leu Leu Asp
                325                 330                 335

Ala Gln Asp Trp Met Thr Asp Ala Gln Leu Thr Ala Leu Trp Arg Gln
            340                 345                 350

Val Thr Arg Thr Ala Ala Pro Gly Ala Arg Val Ile Phe Arg Thr Gly
        355                 360                 365

Gly Ala Ala Asp Leu Leu Pro Gly Arg Val Pro Glu Glu Ile Leu Gly
370                 375                 380

His Trp Arg Ala Asp Arg Ala Ala Gly Gln Ala Gly His Ala Ala Asp
385                 390                 395                 400

Arg Ser Ala Ile Tyr Gly Gly Phe His Leu Tyr Arg Arg Arg Asp Ala
                405                 410                 415

<210> SEQ ID NO 4
<211> LENGTH: 210
<212> TYPE: PRT
<213> ORGANISM: Rhodobacter sphaeroides

<400> SEQUENCE: 4

Met Thr Asp Ala Thr His Ala Ala Leu Met Asp Ala Thr Tyr Arg His
```

```
                  1               5                  10                 15
             Gln Arg Arg Ile Tyr Asp Val Thr Arg Arg His Phe Leu Leu Gly Arg
                            20                 25                 30

Asp Arg Leu Ile Ala Glu Leu Asp Pro Pro Gly Ala Arg Val Leu
                        35                 40                 45

Glu Ile Ala Cys Gly Thr Gly Arg Asn Leu Asp Leu Ile Gly Arg Arg
                        50                 55                 60

Trp Pro Gly Cys Arg Leu Ser Gly Leu Asp Ile Ser Gln Glu Met Leu
             65                 70                 75                 80

Ala Ser Ala Arg Ala Arg Leu Gly Arg Arg Ala Thr Leu Ala Leu Gly
                            85                 90                 95

Asp Ala Thr Arg Phe Glu Ala Leu Pro Leu Phe Gly Thr Asp Arg Phe
                            100                105                110

Glu Arg Ile Val Leu Ser Tyr Ala Leu Ser Met Ile Pro Asp Trp Arg
                            115                120                125

Glu Ala Leu Arg Glu Ala Ala Leu His Leu Val Pro Gly Gly Arg Leu
                        130                135                140

His Val Val Asp Phe Gly Asp Gln Ala Gly Leu Pro Gly Trp Ala Arg
             145                150                155                160

Ala Gly Leu Arg Gly Trp Ile Gly Arg Phe His Val Thr Pro Arg Asp
                            165                170                175

Asp Leu Gly Thr Ala Leu Gly Glu Thr Ala Leu Gly Ile Gly Gly Tyr
                        180                185                190

Ala Glu Tyr Arg Ser Leu Gly Gly Gly Tyr Ala Ile Leu Gly Thr Leu
                        195                200                205

Thr Arg
                 210

<210> SEQ ID NO 5
<211> LENGTH: 26
<212> TYPE: DNA
<213> ORGANISM: Rhodobacter sphaeroides

<400> SEQUENCE: 5
cgccctcacc cacattcccg ccccgc                                            26

<210> SEQ ID NO 6
<211> LENGTH: 31
<212> TYPE: DNA
<213> ORGANISM: Rhodobacter sphaeroides

<400> SEQUENCE: 6
gactgtcccg agatcgaggg ccagcgccag c                                      31

<210> SEQ ID NO 7
<211> LENGTH: 26
<212> TYPE: DNA
<213> ORGANISM: Rhodobacter sphaeroides

<400> SEQUENCE: 7
gccgccgacc gtacggcgat ctacgg                                            26

<210> SEQ ID NO 8
<211> LENGTH: 28
<212> TYPE: DNA
<213> ORGANISM: Rhodobacter sphaeroides

<400> SEQUENCE: 8
```
gctgatggac gcgtcctacc gccaccag                                    28

<210> SEQ ID NO 9
<211> LENGTH: 29
<212> TYPE: DNA
<213> ORGANISM: Rhodobacter sphaeroides

<400> SEQUENCE: 9
cggttcgagc ggctcgtcct ctcctacgc                                   29

<210> SEQ ID NO 10
<211> LENGTH: 29
<212> TYPE: DNA
<213> ORGANISM: Rhodobacter sphaeroides

<400> SEQUENCE: 10
ggatatgcga ttctcgccac gctcacgcg                                   29

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
gctctagaat ggcgcagttc gccctc                                      26

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
acatgcatgc aggacgatcc gctcgaaccg                                  30

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
gctctagaat ggccgacgcc acccat                                      26

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
acatgcatgc aggacgatcc gctcgaaccg                                  30

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
atgcaggtgt ggcctccagt gacgcagttc gccctc        36

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
gagggcgaac tgcgtcactg gaggccacac ctgcat        36

<210> SEQ ID NO 17
<211> LENGTH: 36
<212> TYPE: DNA
<213> ORGANISM: Artificial Sequence
<220> FEATURE:
<223> OTHER INFORMATION: Synthetic

<400> SEQUENCE: 17
atgcaggtgt ggcctccaat gaccgacgcc acccat        36

<210> SEQ ID NO 18
<211> LENGTH: 36
<212> TYPE: DNA
<213> ORGANISM: Artificial Sequence
<220> FEATURE:
<223> OTHER INFORMATION: Synthetic

<400> SEQUENCE: 18
atgggtggcg tcggtcattg gaggccacac ctgcat        36

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
gctctagaaa ccacaagaac taagaa        26

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
acatgcatgc aggacgatcc gctcgaaccg        30

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
acatgcatgc ctctcaccgc gtgagcgtg        29

<210> SEQ ID NO 22
<211> LENGTH: 1248
<212> TYPE: DNA

<213> ORGANISM: Mesorhizobium loti

<400> SEQUENCE: 22

```
atgacggacg tctcctcgga tctggttttt cgccgcggca aggaagttgg aaaggccgtc        60
taccagaacc gcgcgctttc aaagccggc atctccgagc ggctgttcgc cttcctgttt       120
tccggcctcg tctatccgca gatctgggaa gaccccgatg tcgacatgga ggccatgcag      180
cttggtcagg gccatcgcat cgtcacaatc gcttccggcg gctgcaacat cctcgcctac      240
ctcacccgtt cgccggcacg gatcgacgcc gtcgacctca acgccgccca catcgcgctg      300
aaccgcatga agctggaggc ggtgcgccgt ctgccctcgc agggcgatct gttccgcttt      360
ttcggcgccg ccgacaccag ccacaattcg caagcctatg accgctttat tgcgccgcat      420
ctcgatccgg tcagccgcca ctattgggag cgccgcaact ggcgtggtcg ccggcgcatc      480
gccgtcttcg accgcaattt ctaccagacc ggcctgctcg gcctgttcat cgccatgggc      540
catcgcacgc cgaaattctt cggcgtcaac cggcccaca tgatggaagc caggaatatc       600
ggcgagcagc gccgcttctt caacgaggag ctggcgccgg tcttcgacaa gaagcttttg     660
aaatgggcga cctcgcgtaa ggcctcgctg ttcggcctcg gcattccgcc ggcgcagtac      720
gattccctga tcacctcagg cgacggcacc atggccagcg ttctgaaggc ccggctggaa     780
aagctcgcct gcgattttcc cctggaaaac aattatttcg cctggcaggc ttttgccccgc    840
cgctatccaa atcccggtga ggccgccctg ccgcctatc tggaaaagca gaactacgaa      900
accatccgcg gcaatatcga ccgcgtcgcc atccaccatg ccaatctgat cgaattcctc     960
gccggcaagg acgcgggcac cgtcgatcgc ttcatcctgc tcgatgcgca ggactggatg    1020
accgatgacc agctcaacgc gctgtggtcg gaaatcagcc gcaccgcctc cgcaggcgcc    1080
cgcgtcatct tccgcaccgc cgccgagccc agcctgctgc caggccgcgt ctcgacctcg    1140
ctgctcgacc agtgggacta tcaggacgag gcgtcgcgcg aattctcggc acgcgaccgt    1200
tcggccatct atggcggctt ccacctctat gtgaagcgca cggcatga                 1248
```

<210> SEQ ID NO 23
<211> LENGTH: 678
<212> TYPE: DNA
<213> ORGANISM: Mesorhizobium loti

<400> SEQUENCE: 23

```
atgaccgagc tgccggccag ccccgaattc aaggccaatc atgccgaact gatggacggc       60
gtctaccact ggcagcgcca catctatgac ctgactcgaa atactatct gctcggccgc       120
gaccggctga tcgatgggct tgaggtgccg caaggcggca ccgtgctgga actcggctgc      180
ggcaccggcc gcaacatcat cctggccgcc cgccgctacc tgatgcccg cttcttcggc      240
ctggatatct cggccgagat gctggagacg gccggcaagg cgatcgaccg cgaaggcctg     300
tccgccacg taacgctgac acgaggcgac gccaccgatt tcgacgccgc ggcactttac     360
ggcatcgagc gcttcgaccg cgtcttcgtc tcctattcgc tgtcgatgat cccaggctgg   420
gaaaagacgg tgtcggcggc actcgccgca ctatcccca acggctcgct gcacatcgtc    480
gatttcggcc agcaggaagg cctaccgggc tggttccgta ccttgctgcg cggttggctg    540
aaaaaattcc acgtaacgcc gcgtgaatcg ctgcgcgaag ttctggaatc ggaatctcgg   600
cgaaccggcg caaccttccg tttccgcacg ctttatcgcg gttacgcctg gctggcgatg  660
atcaagatcg ccagctaa                                                     678
```

<210> SEQ ID NO 24
<211> LENGTH: 31
<212> TYPE: DNA
<213> ORGANISM: Artificial Sequence
<220> FEATURE:
<223> OTHER INFORMATION: Synthetic

<400> SEQUENCE: 24
acatgcatgc aatgacggac gtctcctcgg a					31

<210> SEQ ID NO 25
<211> LENGTH: 29
<212> TYPE: DNA
<213> ORGANISM: Artificial Sequence
<220> FEATURE:
<223> OTHER INFORMATION: Synthetic

<400> SEQUENCE: 25
cggggtacct catgccgtgc gcttcacat					29

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
gcggatccga tgaccgagct gccgg					25

<210> SEQ ID NO 27
<211> LENGTH: 28
<212> TYPE: DNA
<213> ORGANISM: Artificial Sequence
<220> FEATURE:
<223> OTHER INFORMATION: Synthetic

<400> SEQUENCE: 27
gcaagctttt agctggcgat cttgatca					28

<210> SEQ ID NO 28
<211> LENGTH: 1251
<212> TYPE: DNA
<213> ORGANISM: Agrobacterium tumefaciens

<400> SEQUENCE: 28
atgacgagtg cggcacccaa gaccggcttc agcaaaaaca cgaaactgaa gtccgcattg			60
ctccagcaca aggcactctc caaaagcggc ctgtccgaac ggttttttcgg cgtcctcttt		120
tccggcctcg tctatccgca gatctgggaa gaccccgaga tcgacatgga agcgatggag		180
cttggcgaag gccaccgcat cgtcaccatc ggctccggcg gctgcaacat gctggcctat		240
ctctcgcgca accggccag catcgatgtg tggacctca acccgcacca catcgcgctg		300
aacaagctga agctcgctgc cttccgccat ctgcccgccc atcaggatgt ggtgcgccac		360
ttcggccgcg ccggcacccg cagcaacagc gtcggttatg accgtttcat cgccgagcat		420
ctggatgcca cgaccaaggc atactggtcg aagcgcaccc tttccggccg ccgtcgcatt		480
tcggtgttcg acaggaacat ctaccggacc ggcctgctcg gccgtttcat cggcgccggc		540
cacatcatgg cccgcctgca cggcgtgaaa ctcaccgaaa tggccaagac ccggacgctg		600
gacgaacagc gccagttttt tgacagcaag gtcgcgccgc ttttcgacaa gccggtggtg		660
cgctggctga cgaagcgcaa gagctcgctt ttcggccttg gcattccgcc gcgccagtat		720

```
gacgagctgg caagcctttc cagcgacggc acgttgcct ccgtcctcaa ggagcggctg    780
gaaaagcttg cctgcaactt cccgctcagc gacaattatt tcgcctggca ggcctttgcg    840
cgccgttatc ccgagccgca tgagggtgcc ctgcccgctt atctcaagcc ggaatattac    900
gaaaagatcc gcaacaacac cgcgcgcgtc gcggtgcatc acgccaccta taccgagctg    960
ctttcccgca agccggcaaa tggcgtcgac cgctatatcc tgctcgatgc gcaggactgg   1020
atgacggatg tgcagctcaa cgagttatgg tcgcagatca gccgcactgc cgcatccggg   1080
gcacgcgtca tcttccgcac cgcggccgaa aagagcgtta tcgagggccg gctttcgccc   1140
gacatccgca accagtgggt ctatctcgaa gagcgctcca cgaactcaa cgccatggac   1200 cgctcggcca tttatggcgg cttccatatc taccagaggg ctatggcatg a            1251
```

```
<210> SEQ ID NO 29
<211> LENGTH: 416
<212> TYPE: PRT
<213> ORGANISM: Agrobacterium tumefaciens

<400> SEQUENCE: 29

Met Thr Ser Ala Ala Pro Lys Thr Gly Phe Ser Lys Asn Thr Lys Leu
1               5                   10                  15

Lys Ser Ala Leu Leu Gln His Lys Ala Leu Ser Lys Ser Gly Leu Ser
            20                  25                  30

Glu Arg Phe Gly Val Leu Phe Ser Gly Leu Val Tyr Pro Gln Ile
        35                  40                  45

Trp Glu Asp Pro Glu Ile Asp Met Glu Ala Met Glu Leu Gly Glu Gly
    50                  55                  60

His Arg Ile Val Thr Ile Gly Ser Gly Gly Cys Asn Met Leu Ala Tyr
65                  70                  75                  80

Leu Ser Arg Asn Pro Ala Ser Ile Asp Val Val Asp Leu Asn Pro His
                85                  90                  95

His Ile Ala Leu Asn Lys Leu Lys Leu Ala Ala Phe Arg His Leu Pro
            100                 105                 110

Ala His Gln Asp Val Val Arg His Phe Gly Arg Ala Gly Thr Arg Ser
        115                 120                 125

Asn Ser Val Gly Tyr Asp Arg Phe Ile Ala Glu His Leu Asp Ala Thr
    130                 135                 140

Thr Lys Ala Tyr Trp Ser Lys Arg Thr Leu Ser Gly Arg Arg Arg Ile
145                 150                 155                 160

Ser Val Phe Asp Arg Asn Ile Tyr Arg Thr Gly Leu Leu Gly Arg Phe
                165                 170                 175

Ile Gly Ala Gly His Ile Met Ala Arg Leu His Gly Val Lys Leu Thr
            180                 185                 190

Glu Met Ala Lys Thr Arg Thr Leu Asp Glu Gln Arg Gln Phe Phe Asp
        195                 200                 205

Ser Lys Val Ala Pro Leu Phe Asp Lys Pro Val Val Arg Trp Leu Thr
    210                 215                 220

Lys Arg Lys Ser Ser Leu Phe Gly Leu Gly Ile Pro Pro Arg Gln Tyr
225                 230                 235                 240

Asp Glu Leu Ala Ser Leu Ser Ser Asp Gly Thr Val Ala Ser Val Leu
                245                 250                 255

Lys Glu Arg Leu Glu Lys Leu Ala Cys Asn Phe Pro Leu Ser Asp Asn
            260                 265                 270

Tyr Phe Ala Trp Gln Ala Phe Ala Arg Arg Tyr Pro Glu Pro His Glu
        275                 280                 285
```

```
Gly Ala Leu Pro Ala Tyr Leu Lys Pro Glu Tyr Tyr Glu Lys Ile Arg
            290                 295                 300

Asn Asn Thr Ala Arg Val Ala Val His His Ala Thr Tyr Thr Glu Leu
305                 310                 315                 320

Leu Ser Arg Lys Pro Ala Asn Gly Val Asp Arg Tyr Ile Leu Leu Asp
                325                 330                 335

Ala Gln Asp Trp Met Thr Asp Val Gln Leu Asn Glu Leu Trp Ser Gln
            340                 345                 350

Ile Ser Arg Thr Ala Ala Ser Gly Ala Arg Val Ile Phe Arg Thr Ala
            355                 360                 365

Ala Glu Lys Ser Val Ile Glu Gly Arg Leu Ser Pro Asp Ile Arg Asn
            370                 375                 380

Gln Trp Val Tyr Leu Glu Arg Ser Asn Glu Leu Asn Ala Met Asp
385                 390                 395                 400

Arg Ser Ala Ile Tyr Gly Gly Phe His Ile Tyr Gln Arg Ala Met Ala
                405                 410                 415

<210> SEQ ID NO 30
<211> LENGTH: 720
<212> TYPE: DNA
<213> ORGANISM: Agrobacterium tumefaciens

<400> SEQUENCE: 30
atgaaaacca tcggcgagaa tgtcggcctt gcagacagcg cgcatgcggg cttgatggac      60
cgcatgtatc gccaccagcg ccatatctac gatatcaccc gcaaatatta tcttctgggc     120
cgtgaccgga ccatttccgg cctcgacgtg ccaaagggcg gcacgctgct ggaaatcggc     180
tgcggcaccg gccgcaacct gctgctggcc agccgccggt ttcccgacgc caaactcttc     240
ggcctcgata tatcagccga aatgctgctg accgcctccg agaattttgc cggcaaagcg     300
gagcgaccca ttctgcgtgt cgccgatgcc accgctttcc ggtcttcgga attcggccag     360
cccgatggct tcgaccgcgt catgatccct tatgcgctgt cgatgatacc ggactgggaa     420
aaagcgatcg aacaggcgct cgcggcgctg aaacccggcg ttcgctgca tatcgtcgat      480 ttcggccagc aggaacagtt gccgaagtgg ttccgcacgc ttcttcaagc ctggctcacc     540
cgctttcacg ttacgccccg cgcaaatctc cgttacgttc tcgccaatat ggccggccgt     600
ttcgacggga atctcgtctt cgaggaaatc gcgaggggat acgcatggcg ggctgtcatc     660
acgcttccgg ttgccgaagc cccgcagccg aagatccacc gcttattggc tgacgcctga     720

<210> SEQ ID NO 31
<211> LENGTH: 210
<212> TYPE: PRT
<213> ORGANISM: Agrobacterium tumefaciens

<400> SEQUENCE: 31

Met Thr Asp Ala Thr His Ala Ala Leu Met Asp Ala Thr Tyr Arg His
1               5                   10                  15

Gln Arg Arg Ile Tyr Asp Val Thr Arg Arg His Phe Leu Leu Gly Arg
            20                  25                  30

Asp Arg Leu Ile Ala Glu Leu Asp Pro Pro Gly Ala Arg Val Leu
        35                  40                  45

Glu Ile Ala Cys Gly Thr Gly Arg Asn Leu Asp Leu Ile Gly Arg Arg
    50                  55                  60

Trp Pro Gly Cys Arg Leu Ser Gly Leu Asp Ile Ser Gln Glu Met Leu
65                  70                  75                  80
```

```
Ala Ser Ala Arg Ala Arg Leu Gly Arg Arg Ala Thr Leu Ala Leu Gly
            85                  90                  95

Asp Ala Thr Arg Phe Glu Ala Leu Pro Leu Phe Gly Thr Asp Arg Phe
            100                 105                 110

Glu Arg Ile Val Leu Ser Tyr Ala Leu Ser Met Ile Pro Asp Trp Arg
            115                 120                 125

Glu Ala Leu Arg Glu Ala Ala Leu His Leu Val Pro Gly Gly Arg Leu
        130                 135                 140

His Val Val Asp Phe Gly Asp Gln Ala Gly Leu Pro Gly Trp Ala Arg
145                 150                 155                 160

Ala Gly Leu Arg Gly Trp Ile Gly Arg Phe His Val Thr Pro Arg Asp
                165                 170                 175

Asp Leu Gly Thr Ala Leu Gly Glu Thr Ala Leu Gly Ile Gly Gly Tyr
            180                 185                 190

Ala Glu Tyr Arg Ser Leu Gly Gly Gly Tyr Ala Ile Leu Gly Thr Leu
            195                 200                 205

Thr Arg
    210

<210> SEQ ID NO 32
<211> LENGTH: 1251
<212> TYPE: DNA
<213> ORGANISM: Sinorhizobium meliloti

<400> SEQUENCE: 32
atgaccgact tcgccccgga tgccggcttc ggcaagaaga atccgaaact gaaaagcgca      60
ctcctgcagc acaaagctct ctcccccgcc ggtctctccg aacgcctgtt cgggctgctc     120
ttttccggac tcgtctaccc gcagatctgg gaggacccga ttgtcgacat ggaagcgatg     180
cagatccgtc ccggacatcg gatcgtgacg atcggttccg gcggctgcaa catgctgacc     240
tatctctccg ccgagcctgc ccggatagac gtggtcgatc tcaaccccca tcacatcgcg     300
ctcaaccggc tgaagctgtc tgcctttcgc cacctgccga gccacaagga cgtggtgcgg     360
ttcctcgccg tcgaaggtac gcgcacgaat ggccaggcct acgacgtgtt cctcgcgccg     420
aagctcgatc cggcaacccg cgcctattgg aacggccgag atctcaccgg ccgccggcgc     480
atcggcgtct cgggcgcaa cgtttatcgt accggcctgc ttggccgttt catttccgcc     540
agccatgctc tcgcacggct gcacggcatc aatccggaag atttcgtcaa ggcgcgctcc     600
atgcgcgagc agcggcagtt cttcgacgac aagctcgctc cgctcttcga cgtccggtc      660 atccgttgga tcaccagccg caagagctcc cttttcggcc tcggcatccc gccgcagcag     720
ttcgacgaac tcgcgagcct gagccgggag aaatccgtcg ccgcggtgct cgcaatcgc      780 ctggaaaagc tgacctgtca tttcccttg cgcgataact acttcgcctg caggcctttg     840
gcacggcgct acccgcggcc ggacgagggc gagttgccac cttatcttca ggcatcgcga     900
tacgaagcga ttcgcgacaa tgcggagcgc gtcgaggtcc accatgcgag cttcacggag     960
cttctcgccg gcaagcccgc cgcctcagtc gaccgctacg tgctcctcga cgcacaggac    1020
tggatgaccg accagcagct gaacgacctc tggacggaga tcacccgcac cgccgacgcc    1080
ggcgcggtcg tgatcttccg cacggcggcc gaagcgagca tcctgccggg cgcctctcc     1140 accaccctcc tcgatcagtg gtactatgat gccgagactt cgatgaggct cggcgctgaa    1200
gaccggtcgg cgatctatgg cggcttccac atctaccgga agaaagcatg a             1251
```

<210> SEQ ID NO 33
<211> LENGTH: 416
<212> TYPE: PRT
<213> ORGANISM: Sinorhizobium meliloti

<400> SEQUENCE: 33

```
Met Thr Asp Phe Ala Pro Asp Ala Gly Phe Gly Lys Lys Asn Pro Lys
1               5                   10                  15

Leu Lys Ser Ala Leu Leu Gln His Lys Ala Leu Ser Pro Ala Gly Leu
            20                  25                  30

Ser Glu Arg Leu Phe Gly Leu Leu Phe Ser Gly Leu Val Tyr Pro Gln
        35                  40                  45

Ile Trp Glu Asp Pro Ile Val Asp Met Glu Ala Met Gln Ile Arg Pro
50                  55                  60

Gly His Arg Ile Val Thr Ile Gly Ser Gly Gly Cys Asn Met Leu Thr
65                  70                  75                  80

Tyr Leu Ser Ala Glu Pro Ala Arg Ile Asp Val Val Asp Leu Asn Pro
                85                  90                  95

His His Ile Ala Leu Asn Arg Leu Lys Leu Ser Ala Phe Arg His Leu
            100                 105                 110

Pro Ser His Lys Asp Val Val Arg Phe Leu Ala Val Glu Gly Thr Arg
        115                 120                 125

Thr Asn Gly Gln Ala Tyr Asp Val Phe Leu Ala Pro Lys Leu Asp Pro
130                 135                 140

Ala Thr Arg Ala Tyr Trp Asn Gly Arg Asp Leu Thr Gly Arg Arg
145                 150                 155                 160

Ile Gly Val Phe Gly Arg Asn Val Tyr Arg Thr Gly Leu Leu Gly Arg
                165                 170                 175

Phe Ile Ser Ala Ser His Ala Leu Ala Arg Leu His Gly Ile Asn Pro
            180                 185                 190

Glu Asp Phe Val Lys Ala Arg Ser Met Arg Glu Gln Arg Gln Phe Phe
        195                 200                 205

Asp Asp Lys Leu Ala Pro Leu Phe Glu Arg Pro Val Ile Arg Trp Ile
210                 215                 220

Thr Ser Arg Lys Ser Ser Leu Phe Gly Leu Gly Ile Pro Pro Gln Gln
225                 230                 235                 240

Phe Asp Glu Leu Ala Ser Leu Ser Arg Glu Lys Ser Val Ala Ala Val
                245                 250                 255

Leu Arg Asn Arg Leu Glu Lys Leu Thr Cys His Phe Pro Leu Arg Asp
            260                 265                 270

Asn Tyr Phe Ala Trp Gln Ala Phe Ala Arg Arg Tyr Pro Arg Pro Asp
        275                 280                 285

Glu Gly Glu Leu Pro Pro Tyr Leu Gln Ala Ser Arg Tyr Glu Ala Ile
290                 295                 300

Arg Asp Asn Ala Glu Arg Val Glu Val His His Ala Ser Phe Thr Glu
305                 310                 315                 320

Leu Leu Ala Gly Lys Pro Ala Ala Ser Val Asp Arg Tyr Val Leu Leu
                325                 330                 335

Asp Ala Gln Asp Trp Met Thr Asp Gln Gln Leu Asn Asp Leu Trp Thr
            340                 345                 350

Glu Ile Thr Arg Thr Ala Asp Ala Gly Ala Val Val Ile Phe Arg Thr
        355                 360                 365

Ala Ala Glu Ala Ser Ile Leu Pro Gly Arg Leu Ser Thr Thr Leu Leu
370                 375                 380
```

-continued

```
Asp Gln Trp Tyr Tyr Asp Ala Glu Thr Ser Met Arg Leu Gly Ala Glu
385                 390                 395                 400

Asp Arg Ser Ala Ile Tyr Gly Gly Phe His Ile Tyr Arg Lys Lys Ala
            405                 410                 415
```

<210> SEQ ID NO 34
<211> LENGTH: 666
<212> TYPE: DNA
<213> ORGANISM: Sinorhizobium meliloti

<400> SEQUENCE: 34

```
atgagcgccg tgcagaccgc gaatgaaagc cacgctcatc tgatggaccg catgtatcgc      60
taccagcggt acatctatga tttcactcgc aaatactatc tcttcggccg tgacacgctg     120
atccgtgaac tgaacccgcc gccaggcgca tcggtgctgg aagtcggctg cggcacgggc     180
cgcaatctcg ccgtgatcgg ggatctctac cccggtgcgc gcctcttcgg cctcgatatc     240
tcggccgaaa tgctggcgac cgccaaagcc aagctccggc gccaaaatcg gccggacgca     300
gtgttgcggg tcgccgacgc gacgaatttc accgccgcct cattcgatca ggaaggcttc     360
gaccggatcg tcatttccta cgccctttcc atggttcccg aatgggaaaa ggcggtcgat     420
gccgcgattg ccgcgctcaa gccgggcggc tcgctgcata tcgccgactt cggccagcag     480
gaaggttggc cggccggctt ccgccgcttc ctccaggcct ggctcagacg cttccacgtc     540
acgccgcgcg aaacgctttt cgatgtgatg cgcaaaagag ccgagagaaa cggagcggcg     600
ctcgaggtca gatcgctgag acgaggttat gcctggcttg tcgtctatcg ccgcgcggca     660
ccgtag                                                               666
```

<210> SEQ ID NO 35
<211> LENGTH: 221
<212> TYPE: PRT
<213> ORGANISM: Sinorhizobium meliloti

<400> SEQUENCE: 35

```
Met Ser Ala Val Gln Thr Ala Asn Glu Ser His Ala His Leu Met Asp
1               5                   10                  15

Arg Met Tyr Arg Tyr Gln Arg Tyr Ile Tyr Asp Phe Thr Arg Lys Tyr
            20                  25                  30

Tyr Leu Phe Gly Arg Asp Thr Leu Ile Arg Glu Leu Asn Pro Pro
        35                  40                  45

Gly Ala Ser Val Leu Glu Val Gly Cys Gly Thr Gly Arg Asn Leu Ala
    50                  55                  60

Val Ile Gly Asp Leu Tyr Pro Gly Ala Arg Leu Phe Gly Leu Asp Ile
65                  70                  75                  80

Ser Ala Glu Met Leu Ala Thr Ala Lys Ala Lys Leu Arg Arg Gln Asn
                85                  90                  95

Arg Pro Asp Ala Val Leu Arg Val Ala Asp Ala Thr Asn Phe Thr Ala
            100                 105                 110

Ala Ser Phe Asp Gln Glu Gly Phe Asp Arg Ile Val Ile Ser Tyr Ala
        115                 120                 125

Leu Ser Met Val Pro Glu Trp Glu Lys Ala Val Asp Ala Ala Ile Ala
    130                 135                 140

Ala Leu Lys Pro Gly Gly Ser Leu His Ile Ala Asp Phe Gly Gln Gln
145                 150                 155                 160

Glu Gly Trp Pro Ala Gly Phe Arg Arg Phe Leu Gln Ala Trp Leu Arg
                165                 170                 175
```

-continued

```
Arg Phe His Val Thr Pro Arg Glu Thr Leu Phe Asp Val Met Arg Lys
            180                 185                 190

Arg Ala Glu Arg Asn Gly Ala Ala Leu Glu Val Arg Ser Leu Arg Arg
        195                 200                 205

Gly Tyr Ala Trp Leu Val Val Tyr Arg Arg Ala Ala Pro
    210                 215                 220

<210> SEQ ID NO 36
<211> LENGTH: 29
<212> TYPE: DNA
<213> ORGANISM: Artificial Sequence
<220> FEATURE:
<223> OTHER INFORMATION: Synthetic

<400> SEQUENCE: 36
acatgcatgc agtgacgcag ttcgccctc                                      29

<210> SEQ ID NO 37
<211> LENGTH: 29
<212> TYPE: DNA
<213> ORGANISM: Artificial Sequence
<220> FEATURE:
<223> OTHER INFORMATION: Synthetic

<400> SEQUENCE: 37
cggggtacca ggacgatccg ctcgaaccg                                      29

<210> SEQ ID NO 38
<211> LENGTH: 89
<212> TYPE: DNA
<213> ORGANISM: Artificial Sequence
<220> FEATURE:
<223> OTHER INFORMATION: 39

<400> SEQUENCE: 38
atgagaggat cgcatcacca tcaccatcac ggatccgcat gcgagctcgg taccccgggt    60
cgacctgcag ccaagcttaa ttagctgag                                      89

<210> SEQ ID NO 39
<211> LENGTH: 91
<212> TYPE: DNA
<213> ORGANISM: Artificial Sequence
<220> FEATURE:
<223> OTHER INFORMATION: Synthetic

<400> SEQUENCE: 39
atgagaggat ctcatcacca tcaccatcac acggatccgc atgcgagctc ggtaccccgg    60
gtcgacctgc agccaagctt aattagctga g                                   91

<210> SEQ ID NO 40
<211> LENGTH: 90
<212> TYPE: DNA
<213> ORGANISM: Artificial Sequence
<220> FEATURE:
<223> OTHER INFORMATION: Synthetic

<400> SEQUENCE: 40
atgagaggat ctcatcacca tcaccatcac gggatccgca tgcgagctcg gtaccccggg    60
tcgacctgca gccaagctta attagctgag                                     90

<210> SEQ ID NO 41
<211> LENGTH: 415
<212> TYPE: PRT
```

<213> ORGANISM: Mesorhizobium loti

<400> SEQUENCE: 41

```
Met Thr Asp Val Ser Ser Asp Leu Val Phe Arg Arg Gly Lys Glu Val
1               5                   10                  15

Gly Lys Ala Val Tyr Gln Asn Arg Ala Leu Ser Lys Ala Gly Ile Ser
                20                  25                  30

Glu Arg Leu Phe Ala Phe Leu Phe Ser Gly Leu Val Tyr Pro Gln Ile
            35                  40                  45

Trp Glu Asp Pro Asp Val Asp Met Glu Ala Met Gln Leu Gly Gln Gly
    50                  55                  60

His Arg Ile Val Thr Ile Ala Ser Gly Gly Cys Asn Ile Leu Ala Tyr
65                  70                  75                  80

Leu Thr Arg Ser Pro Ala Arg Ile Asp Ala Val Asp Leu Asn Ala Ala
                85                  90                  95

His Ile Ala Leu Asn Arg Met Lys Leu Glu Ala Val Arg Arg Leu Pro
            100                 105                 110

Ser Gln Gly Asp Leu Phe Arg Phe Gly Ala Ala Asp Thr Ser His
    115                 120                 125

Asn Ser Gln Ala Tyr Asp Arg Phe Ile Ala Pro His Leu Asp Pro Val
130                 135                 140

Ser Arg His Tyr Trp Glu Arg Arg Asn Trp Arg Gly Arg Arg Ile
145                 150                 155                 160

Ala Val Phe Asp Arg Asn Phe Tyr Gln Thr Gly Leu Leu Gly Leu Phe
                165                 170                 175

Ile Ala Met Gly His Arg Thr Ala Lys Phe Phe Gly Val Asn Pro Ala
            180                 185                 190

His Met Met Glu Ala Arg Asn Ile Gly Glu Gln Arg Arg Phe Phe Asn
    195                 200                 205

Glu Glu Leu Ala Pro Val Phe Asp Lys Lys Leu Leu Lys Trp Ala Thr
210                 215                 220

Ser Arg Lys Ala Ser Leu Phe Gly Leu Gly Ile Pro Pro Ala Gln Tyr
225                 230                 235                 240

Asp Ser Leu Ile Thr Ser Gly Asp Gly Thr Met Ala Ser Val Leu Lys
                245                 250                 255

Ala Arg Leu Glu Lys Leu Ala Cys Asp Phe Pro Leu Glu Asn Asn Tyr
            260                 265                 270

Phe Ala Trp Gln Ala Phe Ala Arg Arg Tyr Pro Asn Pro Gly Glu Ala
    275                 280                 285

Ala Leu Pro Ala Tyr Leu Glu Lys Gln Asn Tyr Glu Thr Ile Arg Gly
290                 295                 300

Asn Ile Asp Arg Val Ala Ile His His Ala Asn Leu Ile Glu Phe Leu
305                 310                 315                 320

Ala Gly Lys Asp Ala Gly Thr Val Asp Arg Phe Ile Leu Leu Asp Ala
                325                 330                 335

Gln Asp Trp Met Thr Asp Asp Gln Leu Asn Ala Leu Trp Ser Glu Ile
            340                 345                 350

Ser Arg Thr Ala Ser Ala Gly Ala Arg Val Ile Phe Arg Thr Ala Ala
    355                 360                 365

Glu Pro Ser Leu Leu Pro Gly Arg Val Ser Thr Ser Leu Leu Asp Gln
370                 375                 380

Trp Asp Tyr Gln Asp Glu Ala Ser Arg Glu Phe Ser Ala Arg Asp Arg
385                 390                 395                 400
```

Ser Ala Ile Tyr Gly Gly Phe His Leu Tyr Val Lys Arg Thr Ala
        405                 410                 415

<210> SEQ ID NO 42
<211> LENGTH: 225
<212> TYPE: PRT
<213> ORGANISM: Mesorhizobium loti

<400> SEQUENCE: 42

Met Thr Glu Leu Pro Ala Ser Pro Glu Phe Lys Ala Asn His Ala Glu
1               5                   10                  15

Leu Met Asp Gly Val Tyr His Trp Gln Arg His Ile Tyr Asp Leu Thr
            20                  25                  30

Arg Lys Tyr Tyr Leu Leu Gly Arg Asp Arg Leu Ile Asp Gly Leu Glu
        35                  40                  45

Val Pro Gln Gly Gly Thr Val Leu Glu Leu Gly Cys Gly Thr Gly Arg
    50                  55                  60

Asn Ile Ile Leu Ala Ala Arg Arg Tyr Pro Asp Ala Arg Phe Phe Gly
65                  70                  75                  80

Leu Asp Ile Ser Ala Glu Met Leu Glu Thr Ala Gly Lys Ala Ile Asp
                85                  90                  95

Arg Glu Gly Leu Ser Gly His Val Thr Leu Thr Arg Gly Asp Ala Thr
            100                 105                 110

Asp Phe Asp Ala Ala Ala Leu Tyr Gly Ile Glu Arg Phe Asp Arg Val
        115                 120                 125

Phe Val Ser Tyr Ser Leu Ser Met Ile Pro Gly Trp Glu Lys Thr Val
    130                 135                 140

Ser Ala Ala Leu Ala Ala Leu Ser Pro Asn Gly Ser Leu His Ile Val
145                 150                 155                 160

Asp Phe Gly Gln Gln Glu Gly Leu Pro Gly Trp Phe Arg Thr Leu Leu
                165                 170                 175

Arg Gly Trp Leu Lys Lys Phe His Val Thr Pro Arg Glu Ser Leu Arg
            180                 185                 190

Glu Val Leu Glu Ser Glu Ser Arg Arg Thr Gly Ala Thr Phe Arg Phe
        195                 200                 205

Arg Thr Leu Tyr Arg Gly Tyr Ala Trp Leu Ala Met Ile Lys Ile Ala
    210                 215                 220

Ser
225

<210> SEQ ID NO 43
<211> LENGTH: 5242
<212> TYPE: DNA
<213> ORGANISM: Chlamydomonas reinhardtii

<400> SEQUENCE: 43
tgtttattgc cgagcggtgc gcggcgtgac cgccgtgggg ccccagggcc gggcactgcc      60
tgtcacggag gctggtgccc tggcgggaca ccaacttgca actccggaac actcgcgcgg     120
ggtgtgaccg cgaattgagg tctatatgaa agtataattg ctccggttga cgagacaccc     180
tgccgcgact gatggagtga tggcgccaaa ttgacgcttt attctgcgat agttgcaatg     240
gcgcagtctc cagcgccata tgttgacatg ctgtattaat tgcgcactag cgctagcgct     300
gcgcggcgcg gcattggggt cacctgcgtg tccggtgtcc catcgaccat cgtgcggaat     360
gagcccgcga cgtgctcata atagtttgtt tcccgcgcat gctctttgtc gcggccttgt     420
gcgtgcagac ctacatcttt gtgacactca acaaccgtca ttaaaccaaa gcccttaag      480

-continued

| | |
|---|---|
| tgctgttgat tagcggaacc atggggtcgg gtcgtgacgg ccggcctgcg agctacacca | 540 |
| agaagaactt ctccctggag aagctcaagc tcagcagcat gaaggatgac ctgaccgttc | 600 |
| tgcgccatat gtggttcggc agcaagaagg gcgatgatca cgctgctcgc ctggagagct | 660 |
| tctacgggcc ccaggccgct gcctgtaagt cgcgattaac tttatgctca tttaagtgtt | 720 |
| tcgagttgct tacgcgctgt ctgcccgcgc agatgatgct ttccggtcgc ggttcctctg | 780 |
| gggtcgcagg cccatgctcg ctgcagttgc tgcccgcctg gccgagcgct cgaacctcat | 840 |
| ctgggttgac ctgggtggtg gcactggggt gagtcgcggt tgtatcgggg aggtgcggga | 900 |
| tagccctggc cgtttggctg cgcctcgcgc gccatttatg ctgatctgcg ctttgtcttt | 960 |
| gtgcgcgcag gagaatgtcg atatgatggc tgattacatc gacctggcga agttcaagtc | 1020 |
| catctacgtg gtcgacctgt gccactcgct gtgcgaggtg gccaagaaga aggcgaaggc | 1080 |
| caagggctgg aagaatgtcc aggtcgtgga ggccgacgct tgccaatttg cgcccccrga | 1140 |
| gggcaccgcg acgctcatca ccttctccta ctcgctcacg agtgagttgc aacgccgtcg | 1200 |
| acttgccatc ggaggatcca tccacccaca acgttcatcc cctctcaccc cgcgcttttt | 1260 |
| gctgttgcag tgattccacc gttccacaac gtcatcgacc aggcttgctc gtacctgtcc | 1320 |
| caagacggcc tggtgggcgt tgccgacttc tacgtgagcg gcaagtacga cctgcccctg | 1380 |
| cgccagatgc cctggtcgcg ccgtttcttc tggcggtgag ttaccaggcc gcggctacac | 1440 |
| atctctcaag caagcgtagc tgagcggggc acagaaggcg cttagggccc ggggtgcgct | 1500 |
| tctgggtagt ggcaaggata tcggcaaggc ccttcagcta cccgaggtac catggtgatc | 1560 |
| tgtcacgcag ctcatcacgg tgctgactga ggcacgtgct cgagtctgcg gtcgtcatag | 1620 |
| ggctttcagc acatcacagc gcagtctccg aatgcgcgtg ctgcagcgtg tatgctccgg | 1680 |
| gacagcacca tgcaccgtgc ggcgttcttg acttgcatcc gctgctctcg ggcctcccct | 1740 |
| gggttcgctc agacacgtct ccgctgcccc tgtgtctgct gcgtcgtcgt gtgcagatcg | 1800 |
| atcttcgaca tcgacaacat tgacatcggc cccgagcgcc gcgcctacct ggagcagaag | 1860 |
| ctggagcgcg tgtgggagca gaacacccag gtgtgtgccg cgttgacacc tggcctgtgc | 1920 |
| aagcccaagt aaggtttgct catcagccct gcagcacccg cggcgtgcgg cggatattca | 1980 |
| tcggcagagc cgtccgcact gttggttaat ccaccagtcc gcctgccttt cctctgcgtg | 2040 |
| tttcagggtt cgatccccta cgtgccgtgg ctgcgcgccc cctactacgt gtggattggc | 2100 |
| cgcctgccca gcgttggccg tgagtcgcgt cgcgcgggac ctcgtccgca tcaggacaca | 2160 |
| tggttacggg ggcctcagtg aagcgtatcg tatcgttgca gtcgtactgt caagcgtacc | 2220 |
| aacaagcgcg tcccttgcgc gttgaaattg ttgggcgcaa gcatgagccg tgccgccgat | 2280 |
| gcccaactcg cgttgaccct gcagacgccc tgcacgagga gcgcgtggag cggccgccca | 2340 |
| tgttcccgcc caccttcctg tacacgcagt cgtgggagga ccccgagccg gatatggagg | 2400 |
| tgagcggctc agcctgaggc agatacgcac gaaggaaacg ctcgtggtac cccgagggcg | 2460 |
| ggatcacgca cgttcggaag cattgtggca cggtcacatc gtcgcaccag caaagcaagc | 2520 |
| actaagcacc agcggttctg tgggcaatgt gccaccgcaa tgcctggcca gtgcgcagct | 2580 |
| tcgcattagt gtatgccagt atcacgccta gctcagcctg caagctgctg tcgtagaaag | 2640 |
| cagccgatgg tggcactgag cgcgaacact cctgctgaaa ctgtgcctgc catcctctcg | 2700 |
| tgcccttccc aggtgatgga gatcaacccc aaggacacgg tgctgaccct gactagcggc | 2760 |
| ggctgcaatg ccctgaacct gctggtgcag ggggccggcc aggtgagatc atagtgcgtg | 2820 |

```
ctgcacccett tctggtgtcc ttacttcatg atggccgctg cacgaatgt taggaagcgg    2880 ttggcataca tgtagctgca gaatgtcgct gacgtcgtct tccgcgctgc tgctgcaggt    2940
ggtgtcggtg gactgcaacc ccgcgcagtc ggcgcttctg gagctgaaga aggtggccat    3000
tcagcagctg gagtttgagg acgtgtggca ggtaaggggc tcctcatctg gcgcctaggg    3060
actgcacacg tctgttccta ctgtgatgca acatgcggga cctggtcagg ccttgcggca    3120
ttcgcactgc gatgctgtcc cccagggctc agcacatcct ctcgccggct gcaacggcac    3180
agcccttttt acactccgca accctgtct tggtaattcc ccttccacag ctgttcggcg    3240
agggcgtgca cccgcgcatt gaggagctgt acgagaagaa gctggcgccc ttcctgtcgc    3300
aaaccagcca caacttctgg tccaagcgcc tctggtactt ccagcacggc ctgtactacc    3360
agggcggcat gggcaagctg tgctgggtgc tgcagtgcct ggccgtggtg ctgggactgg    3420
gcaagaccgt caagcgcctc gccaacgcgc ccacaatgga ggagcagcgc cgtctgtggg    3480
acagcaacat gctcatccac ttcgtgaaga cgggcccaa gccgctggtg tggctgttcg    3540
tcaagttcgt gagcctggtg ctcttcaaca aggccgtgct gtggttcggc ggcggcgtgc    3600
cgggcaagca gtacgcgctg atcaaggcgg acggcatccc cattgagaac tacatcgcgc    3660
gcaccatgga cggcgtggcg gagaactcgc acgtgcgcaa gcagaactac ttctactaca    3720
actgcctcac cggcaagttc ctgcgcgaca ctgccccac ctacctgcgc gaggcggcct    3780
tcgccaccct caagagtggc gtggtggaca acctgaccgt ctccaccaac ttcttcatgg    3840
aggagctcaa agcgcgcacc tacaccaagg tgggagccag agcggagagt gtgaaaagcg    3900
ggagatggcg ggcgttgtag gtgcatggcg aacgcttgtc tgccagggtg aaagggcaga    3960
gcgagggaaa cggaatttca gaattcggat ggctgggaag cggaaacgaa caagaacgga    4020
atagaaggcc gctggcgaga aactggtgcg ttggcgtttg gcatccagtc tgccaggcgc    4080
ccccgtgcct acctgctcag gtccgtctaa ccgttacaac cctcgccctc accgcccccc    4140 ccccgccca ccaggtgatt ctgatggacc acgtggactg gctggatatg cccgtggcca    4200
acgagctggc cgagtgcctg gccaagcagg ttgcgccggg cggcatcgtc atctggcgct    4260
ccgcctccct cagcccgccc tacgccgagc tgatccagaa ggcgggcttc gacgtgcgct    4320
gcatccgccg cgccactcag ggctacatgg accgcgtcaa catgtacagg tgcgtgcttt    4380
gtccgtgcag gtgtgaggat gtaggatgtc agtggtggcg ggagggagca tgcgggtcga    4440
atgggaggag gttgcgttat tgatgcccga tgggacctgg gtgaatgcgg tgagcggcta    4500
ccgtatgtgc caaggacggg gttggcggcg tcgggcggca gcagaaactt gaaaggttgt    4560
tttagaagat caagatatgt tgcgataacg gaagcgacct agcgtcaggg cgcaacagcg    4620
cgtgggcacc gccgaaatct gcgttgtcct tcgatgtata ccctgatcca atcttgtcgg    4680
tttctccaat gcgcagctcc ttctacatgg cccgccggaa gggcgccaag aaggacaact    4740
aagcagctgg cggcgaaggc acggcgggca agtggccggc tagcaacagc caatggcgct    4800
gacatcgcag gagcagtgcg ttggttgcta gccggcggcg tgccgtgcag ggagcaccgc    4860
tgtggtcaag ctgcggggac tgggctggca gcggaagcag tacaggcagc ggcgcaatgg    4920
gcccgttact cgtgcgggcc ctgcagtcca gctcgaatca ttgcagcttg ctagcccggc    4980
tgtcacagca gcgcttcggt aggtgcggcc gtccacgttt agcgtgctgg actccatagt    5040
agtggtgcca gtaggagtta ggacaatgac cagtagcgca gttgaggacg ggcattttcc    5100
cggtagccca ggttccgctg tctgtggttg tgtgtggca atccacgccg gacgcagttg    5160 tagggacac cgggtcgccg cacaggcttc ctggccactg ctgtgtgggg tgtgggggac    5220
```

```
cgatagcgcc cgaggcagca cc                                              5242

<210> SEQ ID NO 44
<211> LENGTH: 1947
<212> TYPE: DNA
<213> ORGANISM: Chlamydomonas reinhardtii

<400> SEQUENCE: 44 atgggtcgg gtcgtgacgg ccggcctgcg agctacacca agaagaactt ctccctggag        60
aagctcaagc tcagcagcat gaaggatgac ctgaccgttc tgcgccatat gtggttcggc      120
agcaagaagg gcgatgatca cgctgctcgc ctggagagct tctacgggcc ccaggccgct      180
gcctttgctg cccgcctggc cgagcgctcg aacctcatct gggttgacct gggtggtggc      240
actggggaga atgtcgatat gatggctgat tacatcgacc tggcgaagtt caagtccatc      300
tacgtggtcg acctgtgcca ctcgctgtgc gaggtggcca agaagaaggc gaaggccaag      360
ggctggaaga atgtccaggt cgtggaggcc gacgcttgcc aatttgcgcc ccctgagggc      420
accgcgacgc tcatcacctt ctcctactcg ctcacgatga ttccaccgtt ccacaacgtc      480
atcgaccagg cttgctcgta cctgtcccaa gacggcctgg tgggcgttgc cgacttctac      540
gtgagcggca gtacgacctg ccctgcgc cagatgccct ggtcgcgcgc tttcttctgg      600
cgatcgatct tcgacatcga caacattgac atcggccccg agccgcgc ctacctggag      660 cagaagctgg agcgcgtgtg ggagcagaac acccagggtt cgatccccta cgtgccgtgg      720
ctgcgcgccc cctactacgt gtggattggc cgcctgccca cgttggcca cgccctgcac      780 gaggagcgcg tggagcggcc gcccatgttc ccgcccacct tcctgtacac gcagtcgtgg      840
gaggaccccg agccggatat ggaggtgatg agatcaacc caaggacac ggtgctgacc      900 ctgactagcg gcggctgcaa tgccctgaac ctgctggtgc aggggccgg ccaggtggtg      960 tcggtggact gcaaccccgc gcagtcggcg cttctggagc tgaagaaggt ggccattcag     1020
cagctggagt ttgaggacgt gtggcagctg ttcggcgagg gcgtgcaccc gcgcattgag     1080
gagctgtacg agaagaagct ggcgcccttc ctgtcgcaaa ccagccacaa cttctggtcc     1140
aagcgcctct ggtacttcca gcacggcctg tactaccagg gcggcatggg caagctgtgc     1200
tgggtgctgc agtgcctggc cgtggtgctg ggactgggca agaccgtcaa gcgcctcgcc     1260
aacgcgccca aatggagga gcagcgccgt ctgtgggaca gcaacatgct catccacttc     1320
gtgaagaacg ggcccaagcc gctggtgtgg ctgttcgtca agttcgtgag cctggtgctc     1380
ttcaacaagg ccgtgctgtg gttcggcggc ggcgtgccgg gcaagcagta cgcgctgatc     1440
aaggcggacg gcatccccat tgagaactac atcgcgcgca ccatggacgg cgtggcggag     1500
aactcgcacg tgcgcaagca gaactacttc tactacaact gcctcaccgg caagttcctg     1560
cgcgacaact gccccaccta cctgcgcgag gcggccttcg ccaccctcaa gagtggcgtg     1620
gtggacaacc tgaccgtctc caccaacttc ttcatggagg agctcaaagc gcgcacctac     1680
accaaggtga ttctgatgga ccacgtggac tggctggata tgcccgtggc caacgagctg     1740
gccgagtgcc tggccaagca ggttgcgccg gcggcatcg tcatctggcg ctccgcctcc     1800
ctcagcccgc cctacgccga gctgatccag aaggcgggct tcgacgtgcg ctgcatccgc     1860
cgcgccactc agggctacat ggaccgcgtc aacatgtaca gctccttcta catggcccgc     1920
cggaagggcg ccaagaagga caactaa                                          1947

<210> SEQ ID NO 45
```

```
<211> LENGTH: 648
<212> TYPE: PRT
<213> ORGANISM: Chlamydomonas reinhardtii

<400> SEQUENCE: 45
```

| | | | | | | | | | | | | | | |
|---|---|---|---|---|---|---|---|---|---|---|---|---|---|---|
| Met | Gly | Ser | Gly | Arg | Asp | Gly | Arg | Pro | Ala | Ser | Tyr | Thr | Lys | Lys | Asn |
| 1 | | | | 5 | | | | | 10 | | | | | 15 | |
| Phe | Ser | Leu | Glu | Lys | Leu | Lys | Leu | Ser | Ser | Met | Lys | Asp | Asp | Leu | Thr |
| | | | 20 | | | | | 25 | | | | | 30 | | |
| Val | Leu | Arg | His | Met | Trp | Phe | Gly | Ser | Lys | Lys | Gly | Asp | Asp | His | Ala |
| | | 35 | | | | | 40 | | | | | 45 | | | |
| Ala | Arg | Leu | Glu | Ser | Phe | Tyr | Gly | Pro | Gln | Ala | Ala | Phe | Ala | Ala |
| | 50 | | | | | 55 | | | | | 60 | | | | |
| Arg | Leu | Ala | Glu | Arg | Ser | Asn | Leu | Ile | Trp | Val | Asp | Leu | Gly | Gly | Gly |
| 65 | | | | | 70 | | | | | 75 | | | | | 80 |
| Thr | Gly | Glu | Asn | Val | Asp | Met | Met | Ala | Asp | Tyr | Ile | Asp | Leu | Ala | Lys |
| | | | | 85 | | | | | 90 | | | | | 95 | |
| Phe | Lys | Ser | Ile | Tyr | Val | Val | Asp | Leu | Cys | His | Ser | Leu | Cys | Glu | Val |
| | | | 100 | | | | | 105 | | | | | 110 | | |
| Ala | Lys | Lys | Lys | Ala | Lys | Ala | Lys | Gly | Trp | Lys | Asn | Val | Gln | Val | Val |
| | | 115 | | | | | 120 | | | | | 125 | | | |
| Glu | Ala | Asp | Ala | Cys | Gln | Phe | Ala | Pro | Pro | Glu | Gly | Thr | Ala | Thr | Leu |
| | 130 | | | | | 135 | | | | | 140 | | | | |
| Ile | Thr | Phe | Ser | Tyr | Ser | Leu | Thr | Met | Ile | Pro | Pro | Phe | His | Asn | Val |
| 145 | | | | | 150 | | | | | 155 | | | | | 160 |
| Ile | Asp | Gln | Ala | Cys | Ser | Tyr | Leu | Ser | Gln | Asp | Gly | Leu | Val | Gly | Val |
| | | | | 165 | | | | | 170 | | | | | 175 | |
| Ala | Asp | Phe | Tyr | Val | Ser | Gly | Lys | Tyr | Asp | Leu | Pro | Leu | Arg | Gln | Met |
| | | | 180 | | | | | 185 | | | | | 190 | | |
| Pro | Trp | Ser | Arg | Arg | Phe | Phe | Trp | Arg | Ser | Ile | Phe | Asp | Ile | Asp | Asn |
| | | 195 | | | | | 200 | | | | | 205 | | | |
| Ile | Asp | Ile | Gly | Pro | Glu | Arg | Arg | Ala | Tyr | Leu | Glu | Gln | Lys | Leu | Glu |
| | 210 | | | | | 215 | | | | | 220 | | | | |
| Arg | Val | Trp | Glu | Gln | Asn | Thr | Gln | Gly | Ser | Ile | Pro | Tyr | Val | Pro | Trp |
| 225 | | | | | 230 | | | | | 235 | | | | | 240 |
| Leu | Arg | Ala | Pro | Tyr | Tyr | Val | Trp | Ile | Gly | Arg | Leu | Pro | Ser | Val | Gly |
| | | | | 245 | | | | | 250 | | | | | 255 | |
| His | Ala | Leu | His | Glu | Glu | Arg | Val | Glu | Arg | Pro | Pro | Met | Phe | Pro | Pro |
| | | | 260 | | | | | 265 | | | | | 270 | | |
| Thr | Phe | Leu | Tyr | Thr | Gln | Ser | Trp | Glu | Asp | Pro | Glu | Pro | Asp | Met | Glu |
| | | 275 | | | | | 280 | | | | | 285 | | | |
| Val | Met | Glu | Ile | Asn | Pro | Lys | Asp | Thr | Val | Leu | Thr | Leu | Thr | Ser | Gly |
| | 290 | | | | | 295 | | | | | 300 | | | | |
| Gly | Cys | Asn | Ala | Leu | Asn | Leu | Leu | Val | Gln | Gly | Ala | Gly | Gln | Val | Val |
| 305 | | | | | 310 | | | | | 315 | | | | | 320 |
| Ser | Val | Asp | Cys | Asn | Pro | Ala | Gln | Ser | Ala | Leu | Leu | Glu | Leu | Lys | Lys |
| | | | | 325 | | | | | 330 | | | | | 335 | |
| Val | Ala | Ile | Gln | Gln | Leu | Glu | Phe | Glu | Asp | Val | Trp | Gln | Leu | Phe | Gly |
| | | | 340 | | | | | 345 | | | | | 350 | | |
| Glu | Gly | Val | His | Pro | Arg | Ile | Glu | Glu | Leu | Tyr | Glu | Lys | Lys | Leu | Ala |
| | | 355 | | | | | 360 | | | | | 365 | | | |
| Pro | Phe | Leu | Ser | Gln | Thr | Ser | His | Asn | Phe | Trp | Ser | Lys | Arg | Leu | Trp |
| | 370 | | | | | 375 | | | | | 380 | | | | |
| Tyr | Phe | Gln | His | Gly | Leu | Tyr | Tyr | Gln | Gly | Gly | Met | Gly | Lys | Leu | Cys |

```
                385                 390                 395                 400
Trp Val Leu Gln Cys Leu Ala Val Val Leu Gly Leu Gly Lys Thr Val
                    405                 410                 415
Lys Arg Leu Ala Asn Ala Pro Thr Met Glu Glu Gln Arg Arg Leu Trp
                420                 425                 430
Asp Ser Asn Met Leu Ile His Phe Val Lys Asn Gly Pro Lys Pro Leu
            435                 440                 445
Val Trp Leu Phe Val Lys Phe Val Ser Leu Val Leu Phe Asn Lys Ala
    450                 455                 460
Val Leu Trp Phe Gly Gly Val Pro Gly Lys Gln Tyr Ala Leu Ile
465                 470                 475                 480
Lys Ala Asp Gly Ile Pro Ile Glu Asn Tyr Ile Ala Arg Thr Met Asp
                485                 490                 495
Gly Val Ala Glu Asn Ser His Val Arg Lys Gln Asn Tyr Phe Tyr Tyr
                500                 505                 510
Asn Cys Leu Thr Gly Lys Phe Leu Arg Asp Asn Cys Pro Thr Tyr Leu
            515                 520                 525
Arg Glu Ala Ala Phe Ala Thr Leu Lys Ser Gly Val Val Asp Asn Leu
    530                 535                 540
Thr Val Ser Thr Asn Phe Phe Met Glu Glu Leu Lys Ala Arg Thr Tyr
545                 550                 555                 560
Thr Lys Val Ile Leu Met Asp His Val Asp Trp Leu Asp Met Pro Val
                565                 570                 575
Ala Asn Glu Leu Ala Glu Cys Leu Ala Lys Gln Val Ala Pro Gly Gly
                580                 585                 590
Ile Val Ile Trp Arg Ser Ala Ser Leu Ser Pro Pro Tyr Ala Glu Leu
                595                 600                 605
Ile Gln Lys Ala Gly Phe Asp Val Arg Cys Ile Arg Arg Ala Thr Gln
            610                 615                 620
Gly Tyr Met Asp Arg Val Asn Met Tyr Ser Ser Phe Tyr Met Ala Arg
625                 630                 635                 640
Arg Lys Gly Ala Lys Lys Asp Asn
                645

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
caggatccaa tggggtcggg tcgt                                             24

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
caggtaccgc cgccagctgc tta                                              23

<210> SEQ ID NO 48
<211> LENGTH: 3427
<212> TYPE: DNA
<213> ORGANISM: Neurospora crassa
```

<400> SEQUENCE: 48

```
crassagacc acgacgcaga atgacgaaca gagaaccaga catgtggatc acagaaccct      60
gtctccctat gttactgggg gccgagcgct ggccacccat tccgttcgga tctcacgcaa     120
aagcggagtg tggaggtggg gaacttcttt tacaacgctc gctattgaag cttctgaaga     180
tgtacatacg ggtttatatg agagagaaaa gatataacta tcggtcttaa aggctaacct     240
caatccaact tctttctctc ttccttcggt tcttgaacag accgtcggat cctctcttct     300
cttacttgac accaacacct tatagcaatg ggagacaaca gtgccatggc ttctcatggt     360
ggtcacatgg gtaacatttc gctaccatca ctttcagtaa cccgaacact agcagacctc     420
aacttcaaca ccaccactac caaatccatc ttcttcaccg gtgtggccgt cttggtattt     480
ctcgtcacca ccagcaacta ttcgcggaag acaaccaaaa acgaggacga caatgaggat     540
gaaggcaacc caagctccct caaatccctc ctcctcttct gctactcctg cttcatcaaa     600
cctcacgcca ccgccggcac cacaggaaca cagcaagatg ccctggagtc gttttaccga     660
agtcaggcag acatttatga tgcgacaagg ggtacgctac tgaaggggag ggaggatatg     720
ttggctcttg cagcttcgca gttgaggtac aaggttgagg ctggacttgg cggacttgga     780
ggagctggag atgggcttga aaaaagacaa aggaatggga agacatgtgt aaccgtggcc     840
gggacaggga ccgggacaag gaggaaaccg atatgggtag atgtacgcct cctcatcaga     900
acccttgcca atgttgaaat cccacacacg gctgaccatc gctacaaaac aggtcggtgg     960
gggcacaggc tggaatatcg aagccatggc caagtttgtc aacgtctctg aattcttcaa    1020
gactgtttac ctagtggact tttcgccgtc actttgtgaa gtggctagga agcggtttgc    1080
caggctgggg tgggagaatg tgagagttat ctgcacggat gctcgcaagt ttaggcttga    1140
ggattatgag gatgttgacg aaggagagtc tggctctgga gattcttcgc cttctttgtc    1200
gggttggtgg ggggagacga agccgggacg acatgcggga gctgagttga tcaccatgtc    1260
ttatagcctt tcgatgatgg tatgtttctt gattaaggac gtcttggggt ggtgtgtgct    1320
gacatatcat gacgatgtag ccggattatt tctcgattat cgattcgctc gagtctctgt    1380
tagcacctca cggcttgatt gccgtcgtgg acttttacgc ccagtcgaaa gtcgacttca    1440
cattccgcaa ctacacgggt ggtcttatga accgacacgt tggctatttc gcgcggaact    1500
tctggcgctc gtggttcgat gctgacaggg tgtctcttga gccagctcgt cgagattatc    1560
tcgagtacag gttcgggact gtcctgaccg tcaacgcccg caacaacact ttgggagcaa    1620
ttccttacta catctggttg ggatgcctca agaagccctt ttctacgtcg agtctaccac    1680
acgaaattgt ggaacacatc gatgctattg cgacagagtc cccaagatca tcaccccgtc    1740
tagtgggcaa acattcttcc tcagcaacaa atgcgctagc ctttgcagtc ggccgcacag    1800
cgccggagat gcgctcaaag gccttcaata cggccatcga gaacatctcg gccaacctac    1860
ctctcccgtc cttcttctac caaaatcacc actggaggat ctactacgac gatcaactcc    1920
cgaagcacac ccagttcaat gacgagtaca tctacgcctt tacctgggaa gactcgcgcg    1980
tcgacagaga actccttaac ctcgggcccg acgacgtcgt cctagccatc accagcgccg    2040
gcgacaacat tctttcctac ctgatgcaga gtcccgctcg cgtgcacgcc atcgacctaa    2100
acccagccca aaaccacctg cttgaactca agtcgcctc ttttacgact ctggattacc     2160
ccgacgtctg gaagatcttc ggtgagggca acaccccga ctttcgctca ctgctcatct     2220
ccaaactctc ccctcacctc tccggccgcg cgtttcaata ctggctatcc aatgcgcaca    2280
```

-continued

```
tatttaccga ccctgcgggg cgcggtctct atgataccgg cggctcccga tacgctatcc    2340
gtttcttccg ctggatttcc acactcttct tctgccgctc cgcggtccgt cgacttctct    2400
ctactcccac cctcgaaggg caacgttcca tctaccacac caagattcgt ccctgtctgc    2460
tcaaccgctt cgtcaacggc ctggtcctca gctccgacgc cttcctctgg tcggctttgg    2520
gcgtgcccaa gaatcaagtg gctatgatcg aagccgacta ccaccgccgt tctatctcct    2580
cctccaccac ccccagcagc aaagaaaaac caagccgcgc cgaagcaatc ctccactaca    2640
caacctccac ccttgatccc gttctctcca cctcccacct tgcctcggac aacccttact    2700
acctcgtctg tgtcctggga caatacacac gccagtgcca tcccgattac ctttcccctg    2760
ccgcccactc tatactcagc gctcctggag cctttgacgg cttacgcatc cacacggatg    2820
aaatacagga ggtgttggct aggtttcagc cgggtacttt gacagtagcg gtggtgatgg    2880
atagtatgga ttggttcgat ccgccttcgc ctgaggagga aaaggaagga aggggcaagg    2940
cgagggagca agtgaggagg ttgaatcggg cgttgaaggt gggtggaaag gtgttgttga    3000
ggagcgcggg agtggagccg tggtatgtga gggttttttgt ggaggaaggg tttggagcaa    3060
ggagggtggg ttgtcgtgaa tccggaaggg gggaccagga gtgtattgac agggtgaata    3120
tgtatgctag ttgttggatc ttggaaaaga tggaggatct tgaggagttg gttgactcag    3180
cttaagtaga tattttggtc ctaggtgata agttggataa ccctatttag cgcaagacta    3240
cctctactgg ccagaacacg gcatctgata ttctttatct gccactcaac cattcagccg    3300
gctttttgat tcaagcatgg taaaacgagg accgtgggag aaatcgcaac ctctttactg    3360
gcctgacatg acaaggcggg tcagataagt atttgttata agagcttcca cagcaaaaag    3420
atgtccc                                                              3427
```

<210> SEQ ID NO 49
<211> LENGTH: 2727
<212> TYPE: DNA
<213> ORGANISM: Neurospora crassa

<400> SEQUENCE: 49

```
atgggagaca acagtgccat ggcttctcat ggtggtcaca tgggtaacat ttcgctacca      60
tcactttcag taacccgaac actagcagac ctcaacttca acaccaccac taccaaatcc     120
atcttcttca ccggtgtggc cgtcttggta tttctcgtca ccaccagcaa ctattcgcgg     180
aagacaacca aaaacgagga cgacaatgag gatgaaggca acccaagctc cctcaaatcc     240
ctcctcctct tctgctactc ctgcttcatc aaacctcacg ccaccgccgg caccacagga     300
acacagcaag atgccctgga gtcgttttac cgaagtcagg cagacattta tgatgcgaca     360
aggggtacgc tactgaaggg gagggaggat atgttggctc ttgcagcttc gcagttgagg     420
tacaaggttg aggctggact tggcggactt ggaggagctg agatgggct tgaaaaaaga      480 caaaggaatg ggaagacatg tgtaaccgtg gccgggacag ggaccgggac aaggaggaaa     540
ccgatatggg tagatgtcgg tgggggcaca ggctggaata tcgaagccat ggccaagttt     600
gtcaacgtct ctgaattctt caagactgtt tacctagtgg actttcgcc gtcactttgt      660 gaagtggcta ggaagcggtt tgccaggctg gggtgggaga atgtgagagt tatctgcacg     720
gatgctcgca agtttaggct tgaggattat gaggatgttg acgaaggaga gtctggctct     780
ggagattctt cgccttcttt gtcgggttgg tgggggaga cgaagccggg acgacatgcg      840
ggagctgagt tgatcaccat gtcttatagc ctttcgatga tgccggatta tttctcgatt     900
atcgattcgc tcgagtctct gttagcacct cacggcttga ttgccgtcgt ggacttttac     960
```

-continued

```
gcccagtcga aagtcgactt cacattccgc aactacacgg gtggtcttat gaaccgacac      1020
gttggctatt tcgcgcggaa cttctggcgc tcgtggttcg atgctgacag ggtgtctctt      1080
gagccagctc gtcgagatta tctcgagtac aggttcggga ctgtcctgac cgtcaacgcc      1140
cgcaacaaca ctttgggagc aattccttac tacatctggt tgggatgcct caagaagccc      1200 tttctacgt cgagtctacc acacgaaatt gtggaacaca tcgatgctat tgcgacagag       1260
tccccaagat catcaccccg tctagtgggc aaacattctt cctcagcaac aaatgcgcta      1320
gcctttgcag tcggccgcac agcgccgag atgcgctcaa aggccttcaa tacgccatc        1380 gagaacatct cggccaacct acctctcccg tccttcttct accaaaatca ccactggagg      1440
atctactacg acgatcaact cccgaagcac acccagttca atgacgagta catctacgcc      1500
tttacctggg aagactcgcg cgtcgacaga gaactcctta acctcgggcc cgacgacgtc      1560
gtcctagcca tcaccagcgc cggcgacaac attctttcct acctgatgca gagtcccgct      1620
cgcgtgcacg ccatcgacct aaacccagcc caaaaccacc tgcttgaact caaagtcgcc      1680
tcttttacga ctctggatta ccccgacgtc tggaagatct tcggtgaggg caaacacccc      1740
gactttcgct cactgctcat ctccaaactc tcccctcacc tctccggccg cgcgtttcaa      1800
tactggctat ccaatgcgca catatttacc gaccctgcgg ggcgcggtct ctatgatacc      1860
ggcggctccc gatacgctat ccgtttcttc cgctggattt ccacactctt cttctgccgc      1920
tccgcggtcc gtcgacttct ctctactccc acccctcgaag ggcaacgttc catctaccac     1980
accaagattc gtccctgtct gctcaaccgc ttcgtcaacg gcctggtcct cagctccgac      2040
gccttcctct ggtcggcttt gggcgtgccc aagaatcaag tggctatgat cgaagccgac      2100
taccaccgcc gttctatctc ctcctccacc acccccagca gcaaagaaaa accaagccgc      2160
gccgaagcaa tcctccacta cacaaccctcc acccttgatc ccgttctctc cacctcccac     2220
cttgcctcgg acaaccctta ctacctcgtc tgtgtcctgg acaatacac acgccagtgc       2280 catcccgatt accttttcccc tgccgcccac tctatactca gcgctcctgg agcctttgac     2340
ggcttacgca tccacacgga tgaaatacag gaggtgttgg ctaggtttca gccgggtact     2400
ttgacagtag cggtggtgat ggatagtatg gattggttcg atccgccttc gcctgaggag     2460
gaaaaggaag gaaggggcaa ggcgagggag caagtgagga ggttgaatcg ggcgttgaag     2520
gtgggtggaa aggtgttgtt gaggagcgcg ggagtggagc cgtggtatgt gagggttttt     2580
gtggaggaag ggtttggagc aaggagggtg ggttgtcgtg aatccggaag gggggaccag     2640
gagtgtattg acagggtgaa tatgtatgct agttgttgga tcttggaaaa gatggaggat     2700
cttgaggagt tggttgactc agcttaa                                         2727
```

<210> SEQ ID NO 50
<211> LENGTH: 908
<212> TYPE: PRT
<213> ORGANISM: Neurospora crassa

<400> SEQUENCE: 50

```
Met Gly Asp Asn Ser Ala Met Ala Ser His Gly His Met Gly Asn
1               5                   10                  15

Ile Ser Leu Pro Ser Leu Ser Val Thr Arg Thr Leu Ala Asp Leu Asn
            20                  25                  30

Phe Asn Thr Thr Thr Thr Lys Ser Ile Phe Phe Thr Gly Val Ala Val
        35                  40                  45

Leu Val Phe Leu Val Thr Thr Ser Asn Tyr Ser Arg Lys Thr Thr Lys
```

-continued

```
                50                  55                  60
Asn Glu Asp Asp Asn Glu Asp Glu Gly Asn Pro Ser Ser Leu Lys Ser
 65                  70                  75                  80

Leu Leu Leu Phe Cys Tyr Ser Cys Phe Ile Lys Pro His Ala Thr Ala
                    85                  90                  95

Gly Thr Thr Gly Thr Gln Gln Asp Ala Leu Glu Ser Phe Tyr Arg Ser
                100                 105                 110

Gln Ala Asp Ile Tyr Asp Ala Thr Arg Gly Thr Leu Leu Lys Gly Arg
                115                 120                 125

Glu Asp Met Leu Ala Leu Ala Ala Ser Gln Leu Arg Tyr Lys Val Glu
                130                 135                 140

Ala Gly Leu Gly Gly Leu Gly Gly Ala Gly Asp Gly Leu Glu Lys Arg
145                 150                 155                 160

Gln Arg Asn Gly Lys Thr Cys Val Thr Val Ala Gly Thr Gly Thr Gly
                165                 170                 175

Thr Arg Arg Lys Pro Ile Trp Val Asp Val Gly Gly Thr Gly Trp
                180                 185                 190

Asn Ile Glu Ala Met Ala Lys Phe Val Asn Val Ser Glu Phe Phe Lys
                195                 200                 205

Thr Val Tyr Leu Val Asp Phe Ser Pro Ser Leu Cys Glu Val Ala Arg
                210                 215                 220

Lys Arg Phe Ala Arg Leu Gly Trp Glu Asn Val Arg Val Ile Cys Thr
225                 230                 235                 240

Asp Ala Arg Lys Phe Arg Leu Glu Asp Tyr Glu Asp Val Asp Glu Gly
                245                 250                 255

Glu Ser Gly Ser Gly Asp Ser Ser Pro Ser Leu Ser Gly Trp Trp Gly
                260                 265                 270

Glu Thr Lys Pro Gly Arg His Ala Gly Ala Glu Leu Ile Thr Met Ser
                275                 280                 285

Tyr Ser Leu Ser Met Met Pro Asp Tyr Phe Ser Ile Ile Asp Ser Leu
                290                 295                 300

Glu Ser Leu Leu Ala Pro His Gly Leu Ile Ala Val Val Asp Phe Tyr
305                 310                 315                 320

Ala Gln Ser Lys Val Asp Phe Thr Phe Arg Asn Tyr Thr Gly Gly Leu
                325                 330                 335

Met Asn Arg His Val Gly Tyr Phe Ala Arg Asn Phe Trp Arg Ser Trp
                340                 345                 350

Phe Asp Ala Asp Arg Val Ser Leu Glu Pro Ala Arg Arg Asp Tyr Leu
                355                 360                 365

Glu Tyr Arg Phe Gly Thr Val Leu Thr Val Asn Ala Arg Asn Asn Thr
                370                 375                 380

Leu Gly Ala Ile Pro Tyr Tyr Ile Trp Leu Gly Cys Leu Lys Lys Pro
385                 390                 395                 400

Phe Ser Thr Ser Ser Leu Pro His Glu Ile Val Glu His Ile Asp Ala
                405                 410                 415

Ile Ala Thr Glu Ser Pro Arg Ser Ser Pro Arg Leu Val Gly Lys His
                420                 425                 430

Ser Ser Ser Ala Thr Asn Ala Leu Ala Phe Ala Val Gly Arg Thr Ala
                435                 440                 445

Pro Glu Met Arg Ser Lys Ala Phe Asn Thr Ala Ile Glu Asn Ile Ser
                450                 455                 460

Ala Asn Leu Pro Leu Pro Ser Phe Phe Tyr Gln Asn His His Trp Arg
465                 470                 475                 480
```

```
Ile Tyr Tyr Asp Asp Gln Leu Pro Lys His Thr Gln Phe Asn Asp Glu
            485                 490                 495

Tyr Ile Tyr Ala Phe Thr Trp Glu Asp Ser Arg Val Asp Arg Glu Leu
            500                 505                 510

Leu Asn Leu Gly Pro Asp Asp Val Leu Ala Ile Thr Ser Ala Gly
            515                 520                 525

Asp Asn Ile Leu Ser Tyr Leu Met Gln Ser Pro Ala Arg Val His Ala
            530                 535                 540

Ile Asp Leu Asn Pro Ala Gln Asn His Leu Leu Glu Leu Lys Val Ala
545                 550                 555                 560

Ser Phe Thr Thr Leu Asp Tyr Pro Asp Val Trp Lys Ile Phe Gly Glu
            565                 570                 575

Gly Lys His Pro Asp Phe Arg Ser Leu Ile Ser Lys Leu Ser Pro
            580                 585                 590

His Leu Ser Gly Arg Ala Phe Gln Tyr Trp Leu Ser Asn Ala His Ile
            595                 600                 605

Phe Thr Asp Pro Ala Gly Arg Gly Leu Tyr Asp Thr Gly Gly Ser Arg
            610                 615                 620

Tyr Ala Ile Arg Phe Phe Arg Trp Ile Ser Thr Leu Phe Phe Cys Arg
625                 630                 635                 640

Ser Ala Val Arg Arg Leu Leu Ser Thr Pro Thr Leu Glu Gly Gln Arg
            645                 650                 655

Ser Ile Tyr His Thr Lys Ile Arg Pro Cys Leu Leu Asn Arg Phe Val
            660                 665                 670

Asn Gly Leu Val Leu Ser Ser Asp Ala Phe Leu Trp Ser Ala Leu Gly
            675                 680                 685

Val Pro Lys Asn Gln Val Ala Met Ile Glu Ala Asp Tyr His Arg Arg
            690                 695                 700

Ser Ile Ser Ser Ser Thr Thr Pro Ser Ser Lys Glu Lys Pro Ser Arg
705                 710                 715                 720

Ala Glu Ala Ile Leu His Tyr Thr Thr Ser Thr Leu Asp Pro Val Leu
            725                 730                 735

Ser Thr Ser His Leu Ala Ser Asp Asn Pro Tyr Tyr Leu Val Cys Val
            740                 745                 750

Leu Gly Gln Tyr Thr Arg Gln Cys His Pro Asp Tyr Leu Ser Pro Ala
            755                 760                 765

Ala His Ser Ile Leu Ser Ala Pro Gly Ala Phe Asp Gly Leu Arg Ile
            770                 775                 780

His Thr Asp Glu Ile Gln Glu Val Leu Ala Arg Phe Gln Pro Gly Thr
785                 790                 795                 800

Leu Thr Val Ala Val Met Asp Ser Met Asp Trp Phe Asp Pro Pro
            805                 810                 815

Ser Pro Glu Glu Lys Glu Gly Arg Gly Lys Ala Arg Glu Gln Val
            820                 825                 830

Arg Arg Leu Asn Arg Ala Leu Lys Val Gly Lys Val Leu Leu Arg
835                 840                 845

Ser Ala Gly Val Glu Pro Trp Tyr Val Arg Val Phe Val Glu Glu Gly
850                 855                 860

Phe Gly Ala Arg Arg Val Gly Cys Arg Glu Ser Gly Arg Gly Asp Gln
865                 870                 875                 880

Glu Cys Ile Asp Arg Val Asn Met Tyr Ala Ser Cys Trp Ile Leu Glu
            885                 890                 895
```

```
Lys Met Glu Asp Leu Glu Glu Leu Val Asp Ser Ala
            900                 905
```

<210> SEQ ID NO 51
<211> LENGTH: 33
<212> TYPE: DNA
<213> ORGANISM: Artificial Sequence
<220> FEATURE:
<223> OTHER INFORMATION: Synthetic

<400> SEQUENCE: 51
caggtaccgg atccaatagc aatgggagac aac                33

<210> SEQ ID NO 52
<211> LENGTH: 34
<212> TYPE: DNA
<213> ORGANISM: Artificial Sequence
<220> FEATURE:
<223> OTHER INFORMATION: Synthetic

<400> SEQUENCE: 52
caaagctttc tagactactt aagctgagtc aacc               34